(12) United States Patent
Chisholm et al.

(10) Patent No.: US 9,834,626 B2
(45) Date of Patent: Dec. 5, 2017

(54) PLANT OIL-BASED MATERIALS

(71) Applicants: Bret Ja Chisholm, West Fargo, ND (US); Harjyoti Kalita, Hilmarcheese, CA (US); Samim Alam, Tarrytown, NY (US); Andrey Chernykh, Fargo, ND (US)

(72) Inventors: Bret Ja Chisholm, West Fargo, ND (US); Harjyoti Kalita, Hilmarcheese, CA (US); Samim Alam, Tarrytown, NY (US); Andrey Chernykh, Fargo, ND (US)

(73) Assignee: NDSU RESEARCH FOUNDATION, Fargo, ND (US)

( * ) Notice: Subject to any disclaimer, the term of this patent is extended or adjusted under 35 U.S.C. 154(b) by 202 days.

(21) Appl. No.: 14/761,082

(22) PCT Filed: Jan. 13, 2014

(86) PCT No.: PCT/US2014/011317
§ 371 (c)(1),
(2) Date: Jul. 15, 2015

(87) PCT Pub. No.: WO2014/113326
PCT Pub. Date: Jul. 24, 2014

(65) Prior Publication Data
US 2015/0368378 A1 Dec. 24, 2015

Related U.S. Application Data

(60) Provisional application No. 61/752,745, filed on Jan. 15, 2013.

(51) Int. Cl.
| | | |
|---|---|---|
| C08F 16/26 | (2006.01) |
| C07C 69/533 | (2006.01) |
| C07D 303/42 | (2006.01) |
| C09D 133/14 | (2006.01) |
| C07C 69/604 | (2006.01) |
| C08G 77/38 | (2006.01) |
| C08F 20/68 | (2006.01) |
| C09D 129/10 | (2006.01) |
| C07C 69/587 | (2006.01) |
| C07D 301/00 | (2006.01) |
| C08L 75/04 | (2006.01) |

(52) U.S. Cl.
CPC ............ *C08F 16/26* (2013.01); *C07C 69/533* (2013.01); *C07C 69/587* (2013.01); *C07C 69/604* (2013.01); *C07D 301/00* (2013.01); *C07D 303/42* (2013.01); *C08F 20/68* (2013.01); *C08G 77/38* (2013.01); *C08L 75/04* (2013.01); *C09D 129/10* (2013.01); *C09D 133/14* (2013.01)

(58) Field of Classification Search
CPC ... C07C 69/533; C07C 69/587; C07C 69/604; C07D 301/00; C07D 303/42; C08F 16/26; C08F 20/68; C08G 77/38; C08L 75/04; C09D 129/10; C09D 133/14
USPC ........................................................ 526/286
See application file for complete search history.

(56) References Cited

U.S. PATENT DOCUMENTS

| | | | |
|---|---|---|---|
| 2,335,651 | A | 11/1943 | D'Alelio |
| 2,692,256 | A | 10/1954 | Bauer et al. |
| 4,006,270 | A | 2/1977 | Morgan |
| 4,010,126 | A | 3/1977 | Kuzma |
| 4,215,024 | A | 7/1980 | Gomez et al. |
| 4,367,311 | A | 1/1983 | Brandstetter et al. |
| 4,436,773 | A | 3/1984 | Yamabe et al. |
| 4,616,685 | A | 10/1986 | Harakon et al. |
| 4,617,238 | A | 10/1986 | Crivello et al. |
| 4,975,488 | A | 12/1990 | Furukawa et al. |
| 5,070,140 | A | 12/1991 | Lind et al. |
| 5,196,491 | A | 3/1993 | Cho et al. |
| 5,556,930 | A | 9/1996 | Brehm et al. |
| 5,576,407 | A | 11/1996 | Kroner et al. |
| 5,605,941 | A | 2/1997 | Steinmann et al. |
| 5,731,450 | A | 3/1998 | Alexander et al. |
| 7,674,925 | B2 | 3/2010 | Garrett et al. |
| 8,785,582 | B2 | 7/2014 | Hojo et al. |
| 9,382,352 | B2 | 7/2016 | Chisholm et al. |
| 9,487,420 | B2 | 11/2016 | Chisholm et al. |
| 9,546,122 | B2 | 1/2017 | Chisholm et al. |
| 9,630,897 | B2 | 4/2017 | Chisholm et al. |

(Continued)

FOREIGN PATENT DOCUMENTS

| | | |
|---|---|---|
| DE | 102008031828 A1 | 7/2010 |
| EP | 0 406 977 A1 | 1/1991 |

(Continued)

OTHER PUBLICATIONS

List et al. (Hydrogenation of Soybean Oil Triglycerides: Effect of Pressure on Selectivity, JAOCS 77, 311- 314, Mar. 2000).*
Aakesson et al., "Preparation of thermoset composites from natural fibres and acrylate modified soybean oil resins," *J Appl Polym Sci*, Nov. 15, 2009; 114(4):2502-2508.
Alam, "Synthesis and Characterization of Novel Polyvinylether Polymers Produced Using Carbocationic Polymerization," Doctoral Dissertation; cover date—Oct. 2011. North Dakota State University. 370 pages. Available Jun. 1, 2012.
Alam et al., "2-(Vinyloxy)ethyl soyate as a versatile platform chemical for coatings: An overview," *Eur. J. Lipid Sci. Technol.* 2014; 116(1): 2-15 (epub Sep. 19, 2013).

(Continued)

*Primary Examiner* — Ling Choi
*Assistant Examiner* — Chun-Cheng Wang
(74) *Attorney, Agent, or Firm* — Mueting, Raasch & Gebhardt, P.A.

(57) ABSTRACT

Plant oil-based compounds are provided which possess both low viscosity and high reactive functionality. These compounds are useful in coating and composite applications, as well as related methods. Exemplary compounds can be produced by transesterification of a plant oil triglyceride with a nucleophile reactant, such as a vinyl-functional alcohol, to yield reactive fatty acid-containing monomers.

13 Claims, 5 Drawing Sheets

(56) References Cited

U.S. PATENT DOCUMENTS

| | | | |
|---|---|---|---|
| 9,631,040 B2 | 4/2017 | Chisholm et al. | |
| 2005/0187414 A1 | 8/2005 | Faust et al. | |
| 2005/0250923 A1* | 11/2005 | Palmese | C08F 220/26 526/317.1 |
| 2006/0020062 A1 | 1/2006 | Bloom | |
| 2007/0259166 A1 | 11/2007 | Killiliea et al. | |
| 2007/0293652 A1 | 12/2007 | Schwendeman et al. | |
| 2008/0058448 A1* | 3/2008 | Flanigan | C08G 59/027 524/114 |
| 2008/0146738 A1 | 6/2008 | Dershem | |
| 2008/0234447 A1 | 9/2008 | Shaffer et al. | |
| 2009/0018287 A1 | 1/2009 | Palmese et al. | |
| 2009/0029162 A1 | 1/2009 | Ukei et al. | |
| 2009/0208872 A1 | 8/2009 | Wolf et al. | |
| 2011/0057340 A1 | 3/2011 | Perichaud et al. | |
| 2012/0316309 A1 | 12/2012 | Chisholm et al. | |
| 2013/0245189 A1 | 9/2013 | Hojo et al. | |
| 2013/0320255 A1 | 12/2013 | Chisholm et al. | |
| 2014/0296444 A1 | 10/2014 | Chisholm et al. | |
| 2015/0166701 A1 | 6/2015 | Chisholm et al. | |
| 2016/0023980 A1 | 1/2016 | Chisholm et al. | |

FOREIGN PATENT DOCUMENTS

| | | |
|---|---|---|
| GB | 2 239 248 A | 6/1991 |
| JP | 2002-155114 A | 5/2002 |
| WO | WO 2009/014684 A2 | 1/2009 |
| WO | WO 2009/014684 A3 | 3/2009 |
| WO | WO 2009/111722 A2 | 9/2009 |
| WO | WO 2009/111722 A3 | 12/2009 |
| WO | WO 2010/035903 A1 | 4/2010 |
| WO | WO 2011/060293 A1 | 5/2011 |
| WO | WO 2013/173734 A1 | 11/2013 |
| WO | WO 2014/197041 A2 | 12/2014 |
| WO | WO 2015/134080 A2 | 9/2015 |

OTHER PUBLICATIONS

Alam et al., "Coatings derived from novel, soybean oil-based polymers produced using carbocationic polymerization," *J Coat Technol Res*, Nov. 2011;8(6):671-683.

Alam, et al., "Synthesis and characterization of a novel epoxy-functional polymer from soybean oil," Oral Presentation on Mar. 28, 2011 at the 241st American Chemical Society National Meeting and Exposition Mar. 27-31, 2011 held in Anaheim, CA. Retrieved from the Internet on Apr. 30, 2013: abstracts.acs.org/chem/214nm/program/view.php/obj_id=68555&terms=.

Alam et al., "Synthesis and Characterization of a Novel Epoxy-Functional Polymer from Soybean Oil," *Polymer Preprints*, 2011; (52)1:57-58 (available Feb. 11, 2011).

Aocs, 104th AOCS Annual Meeting & Expo, Apr. 28-May 1, 2013, Montreal, Quebec, Canada; 7 pgs.

Aoshima et al., "Living Cationic Polymerization of Vinyl Monomers by Organoaluminum Halides. 3. Living Polymerization of Isobutyl Vinyl Ether by Ethyldichloroaluminum in the Presence of Ester Additives," *Macromolecules*, 1989; 22(3): 1009-1013.

Aoshima et al., "A Renaissance in Living Cationic Polymerization," *Chem. Rev.*, 2009; 109: 5245-5287.

ASTM D 5402-93, "Standard Practice for Assessing the Solvent Resistance of Organic Coatings Using Solvent Rubs," West Conshohocken, PA, 1999: 2 pgs.

ASTM D 4366-95, "Standard Test Methods for Hardness of Organic Coatings by Pendulum Damping Tests (Withdrawn 2003)," West Conshohocken, PA, 1995: 2 pgs.

ASTM D 2794-93, "Standard Test Method for Resistance of Organic Coatings fto the Effects of Rapid Deformation (Impact)," West Conshohocken, PA, 2010: 3 pgs.

ASTM D 638-5, "Standard Test Method for Tensile Properties of Plastics," West Conshohocken, PA, 2014: 17 pgs.

Bajpai et al., "A Study of the Film Properties of Pigmented UV-Cureable Epoxidised Soybean Oil," *Pigm Resin Technol*, 2004;33:160-164.

Biopreferred—www.biopreferred.gov/Default.aspx.

Brekke et al., "Nonconjugated Linseed Vinyl Ether by Vinyl Transetherification Preparation Procedure," *J. Am. Oil Chemists' Soc.*, 1960; 37(11): 568-570.

Brentin et al., "Rubber Compounds: A Market Opportunity Study." Omni Tech International, Ltd., Midland, MI, Sep. 2011; pp. 1-92.

Challener, "Bio-based resins for paints and coatings: moving beyond basic vegitbal oils," *JCT Coatings Tech*, Jul. 1, 2013; 1-10.

Chisholm, "An investigation of the utility of novel soybean oil-based copolymers in rubber compounds," Grant Abstract, United Soybean Board 2013, Retrieved from the Internet on Apr. 30, 2013 : www.soyb eancheckoffresearch.org/DetailsbyPaperid.php/id_Paper=3189.

Chisholm, "Novel polymers based on soybean oil," Grant Abstract, North Dakota Soybean Council 2013. Retrieved from the Internet on Apr. 30, 2013: www.soybeancheckoffresearch.org/DetailsbyPaperid.php/id_Paper=3090.

Chisholm, "Novel soybean oil-based polymers," Grant Abstract, North Dakota Soybean Council 2011. Retrieved from the Internet on Apr. 30, 2013: www.soybeancheckoffresearch.org/DetailsbyPaperid.php/id_Paper=1569.

Clarient "Your universally applicable Polymer—Polyalkylen-/Polyethylenglykole". Edition 2007. Brochure. 48 pages.

Deng et al., "Metabolic engineering of *Thermobifida fusca* for direct aerobic bioconversion of untreated lignocellulosic biomass to 1-propanol," *Metabolic Eng.*, Sep. 2011;13(5):570-577.

Dufek et al., "Reactions of Unsaturated Fatty Alcohols. VII. Polymerization of Vinyl Ethers Catalyzed by Stannic and Ferric Chlorides," *J. Am. Oil Chemists' Soc.*, Jan. 1960; 37:37-40.

Dufek et al., "Reactions of Unsaturated Fatty Alcohols. XIII. Copolymers of Unsaturated Fatty Vinyl Ethers and Cyclic Monomers," *J. Am. Oil Chemists' Soc.*, May 1962; 39: 238-241.

Eckey et al., "Production of Polyvinyl Esters by Ester Interchange," *J. Am. Oil Chemists' Soc.*, Apr. 1955; 32(4): 185-191.

Flory, *Principles of Polymer Chemistry*, Cornell University Press, Ithaca, NY, 1953. Cover page, title page and table of contents.

Fu et al., "Thermal and mechanical properties of acrylated expoxidized-soybean oil-based thermosets," *J Appl Polym Sci*, Aug. 15, 2010;117(4):2220-2225.

Gast et al., "Reactions of Unsaturated Fatty Alcohols. IV. Oxidative Degradation of Lauryl Isopropyl Ether," *J. Org. Chem.*, Feb. 1959; 24:160-165.

Gast et al., "Reactions of Unsaturated Fatty Alcohols. VIII. Preparation and Properties of Some Copolymers of Nonconjugated Linseed Vinyl Ether and Lower Alkyl Vinyl Ethers," *J. Am. Oil Chemists' Soc.*, Feb. 1960; 37:78-80.

Hill, "Structure/Property Relationships of Thermoset Coatings," *J Coat Technol.*, 1992;64(808):29-42.

Khot et al., "Development and application of triglyceride-based polymers and composites," *J. Polym. Sci., Part A: Polym. Chem.*, Oct. 17, 2001; 82(3):703-723.

Kim et al., "Soybean Oil-Based Photo-Crosslinked Polymer Networks," *J Polym Environ*, Sep. 2010;18(3):291-297.

Klebaur, "CoatingsTech 2013 Focuses on Innovation," http://www.coatingsworld.com/issues/2013-04/view_features/coatingstech-2013-focuses-on-innovation; Apr. 1, 2013.

Kouroosh et al., "Epoxidation of Soybean Oil," *Ann Biol Res*, 2012;3(9):4254-4258.

Lane et al., "Metal-Catalyzed Epoxidations of Alkenes with Hydrogen Peroxide," *Chem Rev*, 2003;103(7):2457-2473.

Mallegol et al., "Drier influence on the curing of linseed oil," *Prog Org Coat*, Nov. 2000;39(2-4):107-113.

Mallegol et al., "Long-term behavior of oil-based varnishes and paints I. Spectroscopic analysis of curing drying oils," *J Am Oil Chem Soc*, Aug. 1999;76(8):967-976.

Mallegol et al., "Long-Term Behavior of Oil-Based Varnishes and Paints. Fate of Hydroperoxides in Drying Oils," *J. Am. Oil Chem. Soc.*, 2000;77(3):249-255.

Mallegol et al., "Long-Term Behavior of Oil-Based Varnishes and Paints. Photo- and Thermooxidation of Cured Linseed Oil," *J. Am. Oil Chem. Soc.*, 2000;77(3):257-263.

Meier et al., "Plant Oil Renewable Resources as Green Alternatives in Polymer Science," *Chem. Soc. Rev.*, 2007; 36: 1788-1802. Available online on Jul. 23, 2007.

(56) References Cited

OTHER PUBLICATIONS

Murayama, *Dynamic Mechanical Analysis of Polymeric Materials,* Elsevier, Amsterdam, 1978. Cover page, title page and table of contents.
National Renewable Energy Laboratory—www.nrel.gov/docs/legosti/fy98/24216.pdf.
NDSU News, "NDSU researchers receive competitive coatings award," Apr. 1, 2011, available online: www.ndsu.edu/news/view/article/10889/. Retrieved on Apr. 30, 2013; 1 page.
O'Hara, "Resins and Monomers for Today's Radiation Curable Coatings," *Radiation Curing of Polymers,* Randel (ed.), The Royal Society of Chemistry, London, 1987:116-127.
Ohta, "Emission of hexenol from higher plants," *Geochem J,* 1984;18:135-141.
Paul et al., *Polymer Chemistry,* Second ed. Boca Raton, CRC, P, 2007:381-389.
Petrovic, "Polyurethanes from Vegetable Oils," *Polym Rev,* 2008;48(1):109-155.
Pinner, "Functionality of non-equivalent mixtures," *J Polym Sci,* Jul. 1956;21(97):153-157.
"Plenish Oil Profile," https://www.plenish.com/food/oil-profile/.
Samper et al., "Thermal and Mechanical Characterization of Epoxy Resins (ELO and ESO) Cured with Anhydrides," *J Am Oil Chem Soc.,* Aug. 2012;89(8):1521-1528.
Schneider et al., "Reactions of Unsaturated Fatty Alcohols. II. Polymerization of Vinyl Ethers and Film Properties of Polymers," *J. Am. Oil Chemists' Soc.,* 1957; 34(5): 244-247.
Schneider et al., "Reactions of Unsaturated Fatty Alcohols. XIV. Preparation and Properties of Styrenated Fatty Vinyl Ether Polymers," *J. Am. Oil Chemists' Soc.,* May 1962; 39: 241-244.
Sperling et al., "Interpenetrating Polymer Networks," in *Polymer Blends Handbook.* Utracki (Ed.) Kluwer Academic Publishers, Dorderecht, The Netherlands: 2002. Cover page, publisher's page, and pp. 417-447.
Tan et al., "Relationships of cure kinetics and processing for epoxidized soybean oil bio-thermoset," *Ind Crop Prod,* May 2013;43:378-385.
Teeter et al., "Reactions of Unsaturated Fatty Alcohols. I. Preparation and Properties of Some Vinyl Ethers," *J. Am. Oil Chemists' Soc.,* Sep. 1956; 33: 399-404.
Teeter et al., "Promising Materials for Protective Coatings. Vinyl Ethers of Polyunsaturated Fatty Alcohols," *Ind. Eng. Chem.,* Nov. 1958; 50(11): 1703-1704.
Teeter, "Vinyl Monomers Derived from Fats and Oils," Paper presented at the 53$^{rd}$ Annual Meeting of The American Oil Chemists' Society on May 7, 1963 in New Orleans, LA. Published in the *J. Am. Oil Chemists' Soc.,* Apr. 1963; 40(4): 143-156.
Thames et al., "Cationic UV-cured coatings of epoxide-containing vegetable oils," *Surf Coat Technol,* Jul. 18, 1999;115(2-3):208-214.
Wan Rosli et al., "UV Radiation Curing of Epoxidized Palm Oil-Cycloaliphatic Diepoxide System Induced by Cationic Photoinitiators for Surface Coatings," *Eur. Polym. J.,* 2003; 39(3): 593-600.

Wang et al., "Polyurethane networks from different soy-based polyols by the ring opening of epoxidized soybean oil with methanol, glycol, and 1,2-propanediol," *J Appl Poly Sci,* Oct. 5, 2009; 114(1): 125-131.
Wicks et al., "Organic Coatings: Science and Technology," in *Book Title.* 3$^{rd}$ edition. John Wiley & Sons (Ed.) Hoboken, NJ: 2007. Cover page, publisher's page, and page 295.
Xu et al., "Advances in the Research and Development of Acrylic Acid Production from Biomass," *Chin J Chem Eng.,* Aug. 2006;14(4):419-427.
Yagci et al., "A Novel Visible Light Initiating System for Cationic Polymerization," *Macromolecules,* 1999; 32:6367-6370.
Zlatanic et al., "Effect of Structure on Properties of Polyols and Polyurethanes Based on Different Vegetable Oils," *J. Polym. Sci., Part B: Polym. Phys.,* 2004; 42: 809-819.
Zou et al., "UV-Curable Cycloaliphatic Epoxide Based on Modified Linseed Oil: Synthesis, Characterization and Kinetics," *Macromol. Chem. Phys.,* 2005; 206(9): 967-975.
Extended European Search Report, dated May 16, 2014, in connection with related European Patent Application No. EP 10830812.3, filed Nov. 12, 2010; 6 pages.
International Search Report and Written Opinion for PCT/US2010/056580, issued by the U.S. Patent and Trademark Office as the International Search Authority dated Jan. 24, 2011; 11 pgs.
International Preliminary Report on Patentability for PCT/US2010/056580, issued by the International Bureau of WIPO dated May 15, 2012; 8 pgs.
International Search Report and Written Opinion for PCT/US2013/041621, issued by the U.S. Patent and Trademark Office as the International Search Authority dated Oct. 21, 2013; 8 pgs.
International Preliminary Report on Patentability for PCT/US2013/041621, issued by the International Bureau of WIPO dated Nov. 18, 2014; 6 pgs.
International Search Report and Written Opinion for PCT/US2014/011317, issued by the U.S. Patent and Trademark Office as the International Search Authority, dated Nov. 19, 2014; 11 pgs.
International Preliminary Report on Patentability for PCT/US2014/011317, issued by the International Bureau of WIPO dated Jul. 30, 2015; 6 pgs.
International Search Report and Written Opinion for PCT/US2014/069993, issued by the U.S. Patent and Trademark Office as the International Search Authority dated Aug. 11, 2015; 9 pgs.
International Preliminary Report on Patentability for PCT/US2014/023181, issued by the International Bureau of WIPO dated Sep. 15, 2015; 6 pgs.
International Preliminary Report on Patentability for PCT/US2014/069993, issued by the International Bureau of WIPO dated Jun. 14, 2016; 6 pgs.
International Search Report and Written Opinion for No. PCT/US2014/23181, issued by the U.S. Patent and Trademark Office as the International Search Authority dated Nov. 28, 2014; 9 pgs.

* cited by examiner

PLANT OIL-BASED MATERIALS

CONTINUING APPLICATION DATA

This application is the §371 U.S. National Stage of International Application No. PCT/US2014/011317, filed 13 Jan. 2014, which claims the benefit of U.S. Provisional Application Ser. No. 61/752,745, filed Jan. 15, 2013, each of which are incorporated by reference herein.

BACKGROUND

Plant oils are used as building blocks for coatings and composites. Relative to many petrochemical building blocks, plant oils often exhibit poor thermomechanical properties, chemical resistance, and scratch resistance due to the inherent molecular flexibility associated with their chemical structure and the relatively high equivalent weight of the reactive functional groups. In addition, plant oil building blocks are much higher in viscosity than many petrochemicals, which limits processability. In order to obtain adequate processability for applications such as radiation-curable coatings or thermoset composites, petrochemicals must be blended with the plant oil material to reduce viscosity. Blending with petrochemicals reduces the bio-based content of the product which is undesirable from an environmental perspective.

SUMMARY OF THE INVENTION

The invention provides compounds, particularly plant oil-based compounds, that possess both low viscosity and high reactive functionality, and that are useful in coating and composite applications. Exemplary compounds can be produced by transesterification of a plant oil triglyceride with a nucleophile reactant, such as an alcohol, to yield a reactive fatty acid-containing monomers. Preferably, the nucleophile reactant contains at least one double or triple bond, thereby providing crosslinking functionality to the resulting compound even if the plant oil fatty acid is saturated. An exemplary nucleophile reactant is a vinyl-functional alcohol.

In one aspect, the invention provides a compound having formula I:

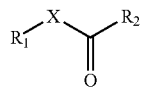

(I)

wherein $R_1$ is an organic group comprising at least one double or triple carbon-carbon bond; X is O, $NR_3$, N, or S; $R_2$ is a fatty acid residue; and $R_3$ is H or alkyl. In a preferred embodiment, the fatty acid residue is from a plant oil triglyceride. Exemplary plant oils include soybean oil, linseed oil, sunflower oil, safflower oil, canola oil, corn oil, cashew nut oil, olive oil, peanut oil, palm oil, sesame oil, cottonseed oil, rapeseed oil, walnut oil, almond oil and coconut oil. Preferably, the plant oil is soybean oil. In an exemplary embodiment, $R_1$ in the compound having formula I is allyl. At least one of $R_1$ and $R_2$ can contain at least one functionality selected from the group consisting of epoxide, acrylate, methacrylate, hydroxyl, and cyclic carbonate.

The invention further provides a composition containing a plurality of compounds having formula I. For example, where the plant oil from which the plant oil triglyceride is obtained is soybean oil, for each of the plurality of compounds, $R_2$ can be a fatty acid residue independently selected from a linolenic acid, a linoleic acid, an oleic acid, a stearic acid, and a palmitic acid.

The invention further provides a curable composition comprising at least one compound having formula I. The compound having formula I may be included in the composition as a reactive diluent.

The invention further provides a method for making a compound having formula I, that includes reacting an unsaturated, nucleophilic reactant with a plant oil triglyceride to yield the compound, wherein the compound of formula I is as follows:

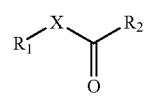

(I)

wherein $R_1$ is an organic group comprising at least one double or triple carbon-carbon bond; X is O, $NR_3$, N, or S; $R_2$ is a fatty acid residue from a plant oil triglyceride; and $R_3$ is H or alkyl. Optionally, the nucleophilic reactant is monovalent. Exemplary nucleophilic reactants include an alcohol, a thiol, or an amine.

The invention further provides a polymer or copolymer that contains the compound of the invention, or a derivative thereof, such as a functionalized polysiloxane that includes a compound of the invention, or derivative thereof. Also provided is a urethane or polyurethane that includes the functionalized polysiloxane of the invention, or derivative thereof.

The invention further provides a method for making a functionalized polysiloxane. A compound of the invention is contacted with a polysiloxane to yield a functionalized polysiloxane.

Also provided by the invention is a coating, film, fiber, foam, adhesive, ink, plastic, elastomer, paint, molding compound, thermoplastic, resin, sealant, lubricant or composite that includes a compound of the invention or a derivative thereof.

More generally, it should be understood that the invention encompasses an article, material, compound, composition, or method including one or more of the features described herein.

DETAILED DESCRIPTION OF ILLUSTRATIVE EMBODIMENTS

Figure 1A:
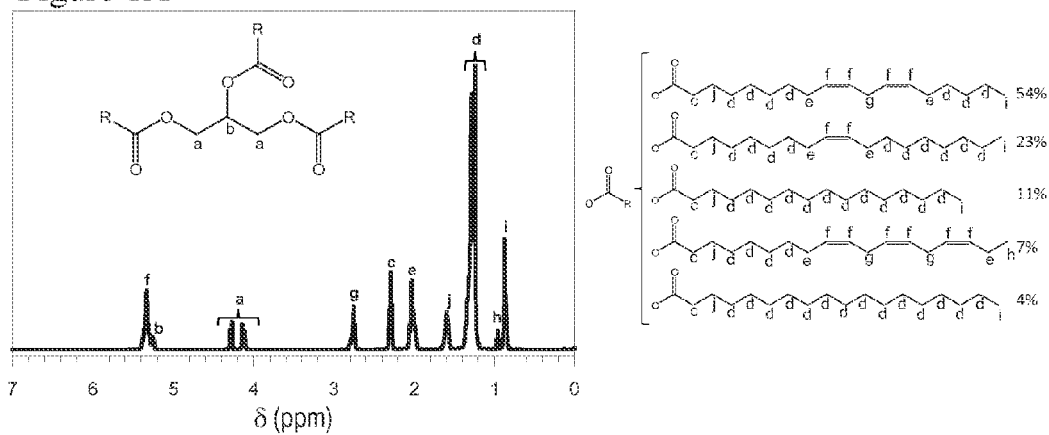
FIG. 1A shows $^1$H NMR spectra obtained for soybean oil (SBO).

The materials of the invention are plant oil based, but have both dramatically lower viscosities and lower reactive group equivalent weight. The fundamental aspect of the invention is exemplified by transesterification of a plant oil triglyceride with an alcohol reactant that also contains at least one double bond (i.e., is unsaturated). By completely replacing the glycerol component of the plant oil triglyceride with three equivalents of the unsaturated alcohol, fatty acid esters are produced that contain at least one double bond that is not derived from the parent plant oil. While transesterification with an unsaturated alcohol is a preferred embodiment, the unsaturated reactant can take the form of an alcohol, thiol or amine (more generally, any nucleophile) that reacts with the plant oil triglyceride to yield the fatty acyl-containing products. Of particular utility as reactants are unsaturated alcohols that are bio-based and/or readily available at a low cost. The materials of the invention provide improved properties over conventional plant oil-based materials while still maintaining high renewable contents.

Compounds and Compositions

The invention provides a compound having formula I:

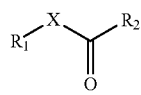

(I)

wherein $R_1$ is an organic group containing at least one double or triple carbon-carbon bond; X is O, N, NR; or S; $R_2$ is a fatty acid residue; and $R_3$ is H or alkyl, for example methyl, ethyl, propyl or isopropyl.

$R_1$ can contain one or more aliphatic groups, aromatic groups, or both; it can be linear or cyclic; it can derivatized or not derivatized; it can be substituted or unsubstituted; it can contain 2, 3, 4, 5, 6, 7, 8, 9, 10, 11, 12, 13, 14, 15, 16, 17, 18, 19, 20 or more carbon atoms. $R_1$ contains at least one site of unsaturation (i.e., a double or triple carbon-carbon bond); optionally, $R_1$ may contain 2, 3, 4 or more sites of unsaturation. In some embodiments, $R_1$ is a hydrocarbon; in other embodiments, $R_1$ contains one or more heteroatoms (e.g., O, N, and/or S). It should be understood that $R_1$ can be selected with reference to the intended use of the compound of formula I and/or with reference to commercial availability of the nucleophilic reactant used to make the compound of formula I, and that selection and incorporation of any $R_1$ can be readily accomplished by the a person skilled in the art of organic or polymer chemistry. The compound of formula I can be prepared using any unsaturated nucleophilic reactant of interest.

The following are exemplary compounds illustrating $R_1$:

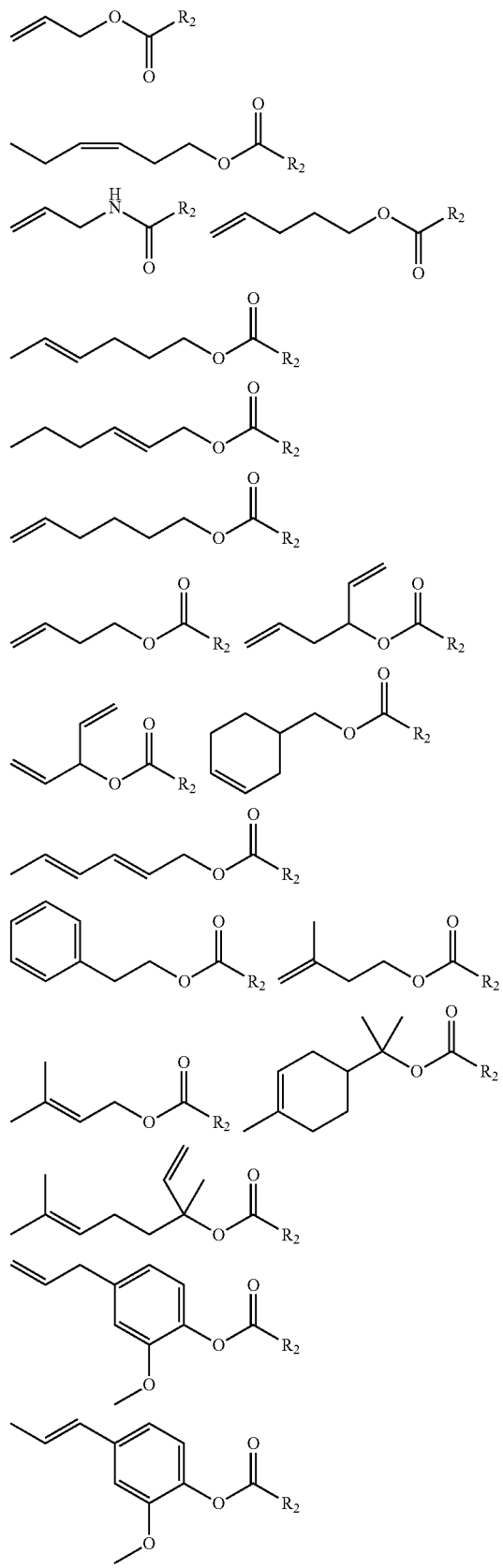

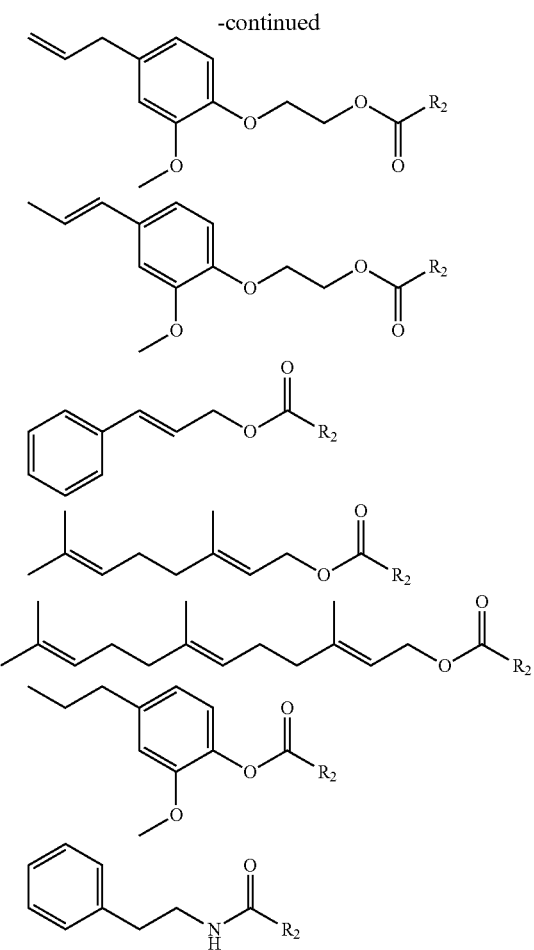

R$_2$, the fatty acid residue, is advantageously, and preferably, obtained from or derived from a plant oil. The plant oil can be a vegetable oil or a nut oil. Exemplary plant oils include, but are not limited to, vegetable oils such as soybean oil, linseed oil, sunflower oil, safflower oil, canola oil, corn oil, and nut oils such as cashew nut oil. Other suitable oils include olive oil, peanut oil, palm oil, sesame oil, cottonseed oil, rapeseed oil, walnut oil, almond oil and coconut oil. Soybean oil is preferred. Triglycerides found in plant oils may contain both saturated and unsaturated fatty acyl groups, i.e., fatty acid residues having one or more double bonds. R$_2$ is preferably a monounsaturated or polyunsaturated fatty acid residue, but may be a saturated fatty acid residue. The fatty acid residue R$_2$ can be underivatized, or it can be functionalized; for example, it can be epoxidized or acrylated. Acrylated plant oils, also known as acrylated epoxidized plant oils, are typically epoxy acrylates prepared from epoxidized plant oils by reacting the epoxide with acrylic acid to produce hydroxyacrylates. For example soybean oil (SBO), when epoxidized, becomes epoxidized soybean oil (ESO). When treated with acrylic acid, ESO becomes acrylated soybean oil (ASBO).

Compositions containing one or a plurality of compounds having Formula I are also encompassed by the invention. In a preferred embodiment, compositions of the invention contain a plurality of compounds having Formula I, said plurality characterized by (and distinguishable by) the different fatty acid residues R$_2$ they contain, which are derived from the plant oil triglyceride. For example, transesterification of soybean oil triglycerides in accordance with the method of the invention can yield multiple alkenyl soyates having Formula I wherein R$_2$ differs, due to the heterogeneity of the fatty acid residues naturally present in plant oil (see, e.g., Example I, relating to soybean oil). Compositions including the compounds of Formula I optionally further include one or more diluent, reactive diluent, filler, thinner, buffer, catalyst, initiator, polymer or copolymer, and the like. Advantageously, in some embodiments of the composition of the invention, the compound of Formula I functions as a reactive diluent. Compositions containing the compounds of Formula I are optionally curable as described elsewhere herein.

Derivatized Compounds

The double bonds both in R$_1$ and R$_2$ can be optionally derivatized using conventional methods to provide other functional groups.

A derivatization reaction can be performed on the compound of formula I, in which case the double bonds present in both R$_1$ and R$_2$ may be functionalized. In some embodiments, however, such as the allyl-containing compound

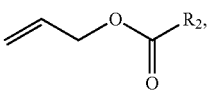

wherein R$_1$ is CH$_2$=CH—CH$_2$—, the monosubstituted double bond may evade derivatization and, advantageously, be available for cross-linking in later reactions. For example, epoxidation of the allyl-containing compound shown above may not derivatize the double bond, which keeps viscosity to a minimum and allows the double bond to participate in cross-linking reactions at a later point, for example during UV-curing. In embodiments wherein R1 contains a disubstituted double bond, typically the double bond will participate in the derivatization reaction (such as epoxidation, etc.).

Alternatively, a derivatization reaction can be performed on the plant oil, more particularly on the plant oil triglyceride, prior to reacting it with the unsaturated nucleophilic reactant to form the compound of formula I. Derivatization reaction can be used to produce epoxidized or acrylated products, for further use in polymer chemistries. Scheme I, below, shows exemplary reactions that can be employed to derivatize the compound of Formula I or its constituents. For example, the compound of formula I (or the plant triglyceride, prior to reaction with the unsaturated nucleophilic reactant), can be epoxidized. The epoxidized compound can be employed in a ring opening reaction using a carboxylic acid (e.g., acrylic acid, methylacrylic acid) or an anhydride (e.g., e.g., methylacrylic anhydride, wherein R$^5$ is methyl in Scheme I, below), to yield the acrylate. Ring-opening can alternatively be achieved with an alcohol, yielding a hydroxylated compound. In another alternative, the epoxidized compound can be reacted with CO$_2$ to form a cyclic carbonate intermediate. The cyclic carbonate intermediate can, for example, be reacted with an amine to form a urethane, which in turn can be used to form polyurethane without the need for an isocyanate cross-linker. Other derivatization chemistries that can be performed on the compound of Formula I (or its constituents) include a thiolene reaction to yield a thioether or thioester, or hydroformylation to yield a hydroxylated compound. The compound of Formula I can be subject to any conventional chemistry useful for derivatizing/functionalizing a double or triple bond to yield a derivatized or functionalized product.

Examples of derivatization chemistries are shown in Scheme I below:

produced by reacting with an appropriate crosslinking agent such as a di- or multi-functional isocyanate compound.

Scheme 1.

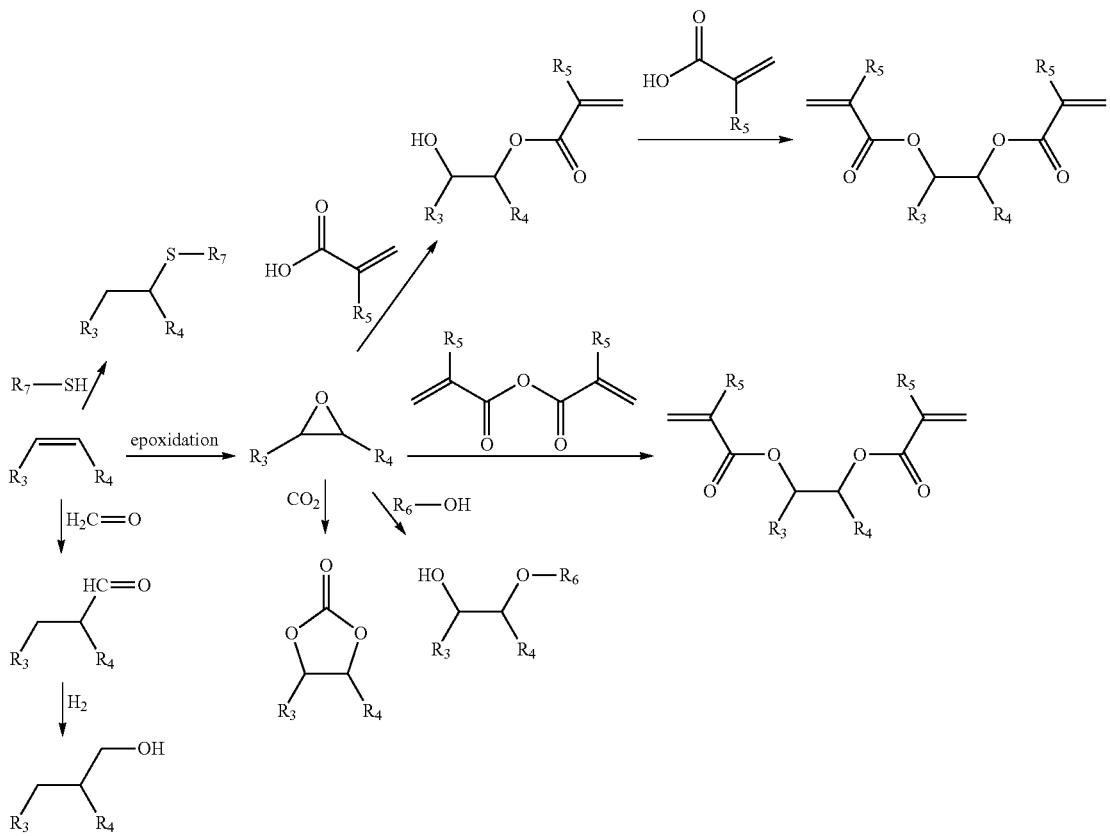

Utility of the Compounds and Compositions

Due to the unsaturation present in plant oil triglycerides, they have been used to produce thermoset polymeric materials. For example, linseed oil and soybean oil have been used for the production of surface coatings that crosslink (i.e. cure) through an oxidative process referred to as autooxidation. In addition, plant oil triglycerides possessing unsaturation have been used to produce epoxy-functional materials by epoxidizing the double bonds. These epoxy-functional derivatives can be cured to produce thermoset networks for coating and composite applications by either polymerizing the epoxy groups or reacting with an appropriate crosslinking agent such as an anhydride-functional compound. Epoxy-functional soybean oil is a commercially available material used for polymeric material applications. The epoxy-functional plant oil triglyceride can be derivatized further to produce acrylate or methacrylate-functional triglycerides that can be used to produce thermoset networks by polymerizing the acrylate or methacrylate groups. Acrylate-functional soybean oil is likewise a commercially available material used for coating and composite applications. Epoxy-functional groups can also be converted to hydroxy groups by ring-opening the epoxy groups with a nucleophilic compound such as an alcohol or water. With the hydroxy-functional material, thermoset networks can be Hydroxy-functional soybean oil is also commercially available and has been used for the production of coatings and composites.

Due to the relatively low cost, ready availability, and multifunctionality (approximately 4.5 double bonds per triglyceride) of soybean oil, it is the most extensively used plant oil for polymer material applications. Compared to petrochemical-based compounds used for coating and composite applications, soybean oil triglyceride-based materials possess some significant limitations. For example, soybean oil has a significantly higher viscosity than many petrochemicals. Also, the equivalent weight associated with the functional groups is significantly higher than that of many petrochemicals. For many coating and composite applications, a low viscosity and low functional group equivalent weight is needed to meet product requirements.

A primary utility of the compounds and compositions of the invention is that, compared to the parent plant oil, they possess both lower viscosity and lower functional group equivalent weight. To illustrate these advantages, radiation-curable surface coatings can be considered. One of the primary advantages of radiation-curable coatings over other coating technologies is the ability to produce coatings without the need for solvent which provides coatings with little or no volatile organic compound (VOC) content. Another major advantage is the relatively low cost of curing compared to conventional thermally-cured coatings. The cure chemistry for radiation-curable coatings typically involves the production and propagation of free radical species or cationic species. Thus, radiation-curable coatings can be classified as either free radical radiation-curable coating or cationic radiation-curable coatings. The functional groups involved in free radical radiation-curable coatings typically involve the acrylate or methacrylate functionality. In contrast, the functional groups typically involved in cationic radiation-curable coatings include epoxy, hydroxy, vinyl ether, and/or oxetane groups.

Besides the initiator that generates free radicals or cationic species upon radiation exposure, a radiation-curable coating typically includes a relatively low viscosity reactive component and a higher viscosity, multi-functional oligomeric reactive component. The low viscosity reactive component, typically referred to as the diluent, functions as a solvent to provide low enough viscosity of the composition to enable effective application. Since the diluent also becomes part of the thermoset matrix, it contributes to the physical and mechanical properties of the coating. The higher viscosity, multi-functional oligomeric component is typically required to provide the balance of physical, mechanical, and chemical properties needed meet the requirements of a given application. Without the oligomeric component, cured coatings tend to be brittle and poorly adhered to the substrate due in large part to the high amount of shrinkage that occurs when just a diluent-type component is cured.

With regard to plant oil-based materials for radiation-curable coatings, their relatively high viscosity and high functional group equivalent weight necessitates the use of a reactive diluent. Since most diluent candidates are petroleum-based, the overall bio-content or renewable content of the coating must be reduced. Since the compounds and compositions of the invention possess significantly lower viscosity and lower functional group equivalent weight, they can be used to provide coatings with higher renewable content by either serving as a diluent or reducing the amount of diluent required to achieve adequate application viscosity and coating mechanical and physical properties.

In general, the materials of the invention are useful in a wide variety of cure chemistries. Thus, there is potential wide spread utility within the coatings and composites industries. They are useful in applications that make use of radiation curing (including photocuring, UV curing and the like), thermal curing, and air curing/autooxidation, for example. They are useful in a variety of medical, scientific, and industrial applications as coatings, films, fibers, foams, adhesives, inks, plastics, elastomers, paints, molding compounds, thermoplastics, resins, sealants, lubricants, composites, and the like. Materials of the invention find application in the electronics, semiconductor, medical device, chemical and coatings industries, and the like.

The materials of the invention, including the compounds of Formula I, can be incorporated into a polymer or copolymer, including a block copolymer. For example, the compounds of Formula I can be incorporated into a polymer or copolymer during a polymerization reaction as a constituent of a polymer backbone, or by grafting onto an existing polymer or copolymer chain, or by reactions that incorporate the inventive compounds at the ends of a polymer or specified points along a polymer backbone. It should be understood that when a monomeric compound of Formula I is covalently incorporated into a polymer, the compound will be chemically altered at the linkage site in order to participate in the covalent linkage.

Functionalized Polysiloxanes

Most polysiloxanes are cured by moisture curing, which can be time-consuming are requires special precautions. The present invention provides a mechanism for curing polysiloxanes using UV-curing or autooxidation.

Polysiloxanes can be functionalized by reaction with a compound of Formula I, such as Formula I wherein $R_1$ is allyl and $R_2$ is a fatty acid residue from soybean oil, to add pendant side chains as shown in Scheme 2, below:

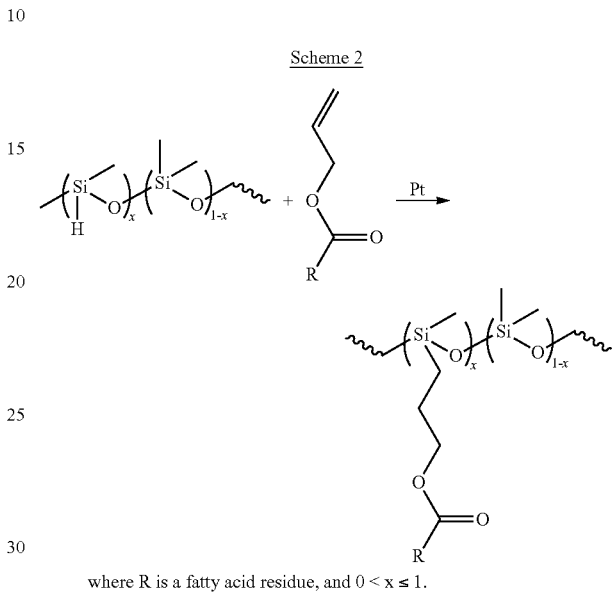

where R is a fatty acid residue, and $0 < x \leq 1$.

In Scheme 2, x is a fraction between 0 and 1. X can be equal to 1, but not 0 (i.e., the polysiloxane reactant must contain a hydride). The hydride can be distributed throughout the polysiloxane reactant, or it can be positioned as an end-functional hydride (i.e., present only at the ends of the polymer chain). The fatty acid residue R, derived from a plant oil, will in many instances contain one or more sites of unsaturation. R can be underivatized (i.e., it can contain one or more double bonds) or it can be functionalized (e.g., with epoxide, acrylate, methacrylate, etc.). The hydride functionality on the polysiloxane backbone is important because the compound of formula I adds to the polysiloxane at that site. The result is a UV-curable siloxane system, because the side chains contain double bonds or other cross-linkable functionalities (epoxide, acrylate, etc.). The resultant functionalized polysiloxane is alternatively curable by autooxidation (optionally catalyzed by a cobalt catalyst). Incorporation of fatty side chains into the polysiloxane in accordance with the method of the invention permits oxidative curing (autooxidation) or photocuring of the resultant functionalized polysiloxane.

Example XVI shows an exemplary synthesis of soyate functionalized polysiloxane.

Methods of Making

Compounds of the invention contain a first, plant oil derived substituent (e.g., $R_2$ of Formula I, a plant oil fatty acid residue) and a second substituent, $R_1$, that contains at least one double or triple carbon-carbon bond. Compounds of the invention are made by reacting an unsaturated, nucleophilic reactant with a plant oil or plant oil reactant.

The plant oil reactant can be, for example, a plant oil triglyceride. Plant oils can be obtained commercially or extracted from plants. They can be used raw, partially purified, or purified. They can be derivatized/functionalized, or not derivatized or functionalized. Commercially available functionalized plant oils suitable for use as the plant oil reactant in the method of making the compounds and compositions of the invention include, for example, epoxy-functional soybean oil, acrylate-functional soybean oil, and hydroxy-functional soybean oil.

The unsaturated, nucleophilic reactant is preferably monovalent, thereby yielding a product, such as the compound of Formula I, which is composed of a single plant oil derived substituent and a single substituent derived from the nucleophilic reactant. Preferred nucleophiles are alcohols, thiols and amines. Using a monovalent reactant allows the molecular weight of the resulting product to remain relatively low. The resulting product, e.g., the compound of Formula I, contains one fatty acid residue per monomer, compared to the three fatty acid residues present in the plant triglyceride. Cleavage of the triglycerides via, e.g., the transesterification reaction, yields three product monomers from each triglyceride. It is important that the nucleophile reactant contains at least one double or triple bond, because a percentage of the fatty acid residues in many plant oils is saturated, and the site of unsaturation in the nucleophilic reactant may provide the only cross-linking functionality in the product that includes a saturated fatty acid residue. For example, about 15% of the fatty acids in soybean oil are saturated, and the nucleophile reactant therefore imparts the crosslinking functionality to the resulting compound of Formula I wherein $R_2$ is saturated.

The unsaturated, nucleophile reactant may contain 1, 2, 3, 4 or more sites of unsaturation. More than one site of unsaturation increases the amount of crosslinking that the substituent can participate in.

The unsaturated, nucleophile reactant can be synthetic, or it can be bio-based or bio-derived, thereby imparting a higher green content to the resulting product. Examples of bio-based or bio-derived monovalent, unsaturated nucleophile reactants include allyl alcohol, cis-3-hexen-1-ol, eugenol, iso-eugenol, sorbic alcohol, vanillin, terpineol, cinnamyl alcohol, farnesol, and geraniol.

Unless otherwise specified, "a," "an," "the," and "at least one" are used interchangeably and mean one or more than one.

The complete disclosures of all patents, patent applications including provisional patent applications, publications including patent publications and nonpatent publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

EXAMPLES

The present invention is illustrated by the following examples. It is to be understood that the particular examples, materials, amounts, and procedures are to be interpreted broadly in accordance with the scope and spirit of the invention as set forth herein.

Example I

Synthesis of Allyl Soyate (AS)

As shown below, AS was synthesized by transesterification of soybean oil with allyl alcohol using KOH as a catalyst. KOH (7 g) was first heated at 140° C. for 30 minutes inside an oven to remove absorbed moisture and then cooled down to room temp by purging with $N_2$. In another flask, soybean oil (250 g) was also bubbled with $N_2$ for 30 minutes. The dried KOH and soybean oil were then charged to a 1 L round bottom flask (rbf) and then ally alcohol (165 g) was added. A condenser was attached to the rbf. The reaction was carried out at 70° C. in a $N_2$ atmosphere for 3 hours. The reaction mixture was cooled down and transferred to a 2 L separating funnel. To this mixture, 1 L of n-Hexane and the solution washed three times with 300 mL of acidic water (pH 3.5-4). Next, it was then washed with deionized (DI) water (300 mL) and then with brine solution (300 mL). The n-hexane layer was dried with $MgSO_4$ and solvent removed under vacuum at 35° C. and 100 bar pressure. The chemical composition of the product was confirmed using proton nuclear magnetic resonance spectroscopy (1H NMR). 1H NMR (400 MHz, $CDCl_3$, TMS): δ (ppm) 5.85-5.97 (m, 1H, —$OCH_2CH$═$CH_2$), 5.15-5.45 (m, 2.5H, $CH_2CH$═$CH$—$CH_2$—; —$OCH_2CH$═$CH_2$), 4.54-4.58 (dt, 2H, —$OCH_2CH$═$CH$—) 2.76 (m, 1.3H, ═$CHCH_2CH$═), 2.32 (t, 2H, —C═$OCH_2$—). 2.03 (m, 3.4H, —$CH_2CH_2CH$═), 1.57 (m, 2H, —C═$OCH_2CH_2$—), 1.29 (m, 16H, —$CH_2CH_2CH_2$—), 0.96-0.87 (m, 3H, —$CHCH_3$).

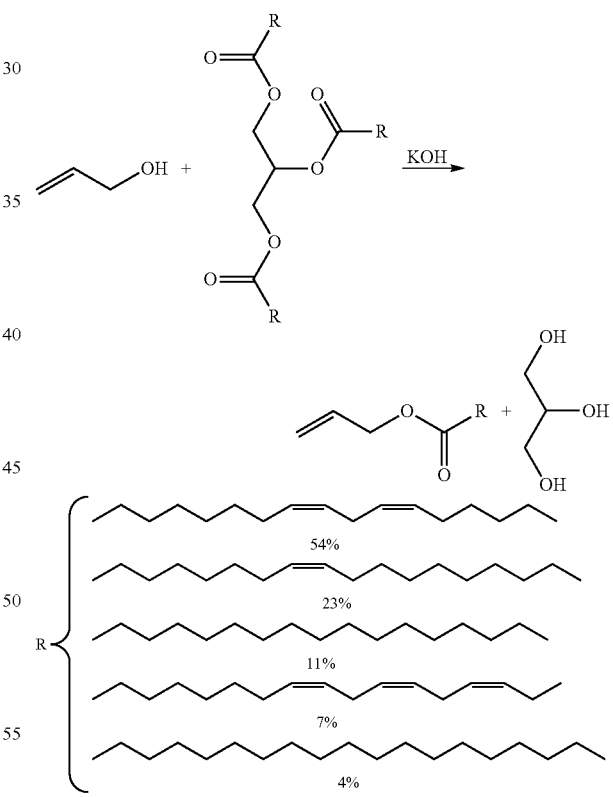

Example II

Synthesis of Epoxidized Allyl Soyate (EAS)

As shown below, an epoxidized derivative of AS was produced using hydrogen peroxide as the oxidation reagent.

With the process utilized, only the internal double bonds derived from the soybean oil were epoxidized. The procedure used was a follows: To a 1 L, two-neck rbf allyl soyate (180 g), acetic acid (31.8 g), and amberlite (25.6 g) were added and mixed well. The rbf was equipped with a condenser and an addition funnel. $H_2O_2$ (145 mL, 50%) was added dropwise via the addition funnel, and the reaction temperature was maintained at 60° C. The reaction was stopped after 5 hours. Once the reaction mixture reached room temperature, it was transferred to a 2 L separating funnel and then bottom layer discarded. Next, 800 mL of ethyl acetate was added to the separating funnel and the resulting solution washed three times with saturated $NaHCO_3$ solution (250 mL), followed by brine wash (300 mL), and a final wash with DI water (300 mL). The ethyl acetate layer was dried with $MgSO_4$ and then solvent was removed using vacuum at 35° C. and 100 bar pressure. Yield: 95%. 1H NMR (400 MHz, $CDCl_1$, TMS): δ (ppm) 5.85-5.97 (m, 1H, —$OCH_2CH$=$CH_2$), 5.15-5.45 (m, 2.5H, $CH_2CH$=$CH$—$CH_2$—; —$OCH_2CH$=$CH_2$), 4.54-4.58 (dt, 2H, —$OCH_2CH$=$CH$—) 2.76-3.22 (m, 3H, —CH(O)CH—), 2.32 (t, 2H, —C=$0CH_2$—), 1.16-1.88 (m, 23H, —C=$0CH_2CH_2$—; —$CH_2CH_2CH_2$—; —CH(O)$CH_2CH_2$—; —CH(O)$CH_2$CH(O)—), 0.96-0.87 (m, 3H, —$CHCH_3$).

Example III

Synthesis of Acrylated Allyl Soyate (AAS)

As shown below, an acrylated derivative of allyl soyate was produced by reacting EAS with acrylic acid. To a 1 L rbf, 100 g of EAS, 3 g potassium acetate, and 0.65 g of hydroquinone were combined. The rbf was equipped with a condenser and an addition funnel. Once the temperature of the reaction mixture reached 100° C., 25.7 g of acrylic acid was added dropwise via the addition funnel. The reaction was carried out over a 7 hour period. Once at room temperature, the reaction mixture was transferred to a 2 L separating funnel and 500 mL of n-hexane. The reaction mixture was washed three times with DI water (150 mL), twice with brine (200 mL), and a final wash with DI water. The hexane layer was dried with $MgSO_4$ and solvent removed by vacuum stripping at 30° C. 1H NMR (400 MHz, $CDCl_3$, TMS): δ (ppm) −6.3-6.5 (m, 1.5H, C=OCH=$CH_2$); 6.1-6.2 (dd, 1.5H, —C=OCH=$CH_2$), 5.85-5.97 (m, 2.5H, —$OCH_2CH$=$CH_2$; —C=OCH=$CH_2$); 5.15-5.45 (m, 2H, —$OCH_2CH$=$CH_2$), 4.85 (1.5H—$CH_2$CHOC=O—), 4.54-4.58 (dt, 1.5H, —$OCH_2CH$=$CH$—), 3.7-4.0 (1.5H, —CHOH), 3.4-3.6 (1.5H, —CHOH), 2.32 (t, 2H, —C=$0CH_2$—), 1.16-1.88 (m, 23H, —C=$0CH_2CH_2$—; —$CH_2CH_2CH_2$—; —CH(O)$CH_2CH_2$—; —CH(O)CHHCH(O)—), 0.96-0.87 (m, 3H, —CHCH). The viscosity of the AAS was found to be 40 cP at a shear rate of 10 $sec^{-1}$ and temperature of 25° C.

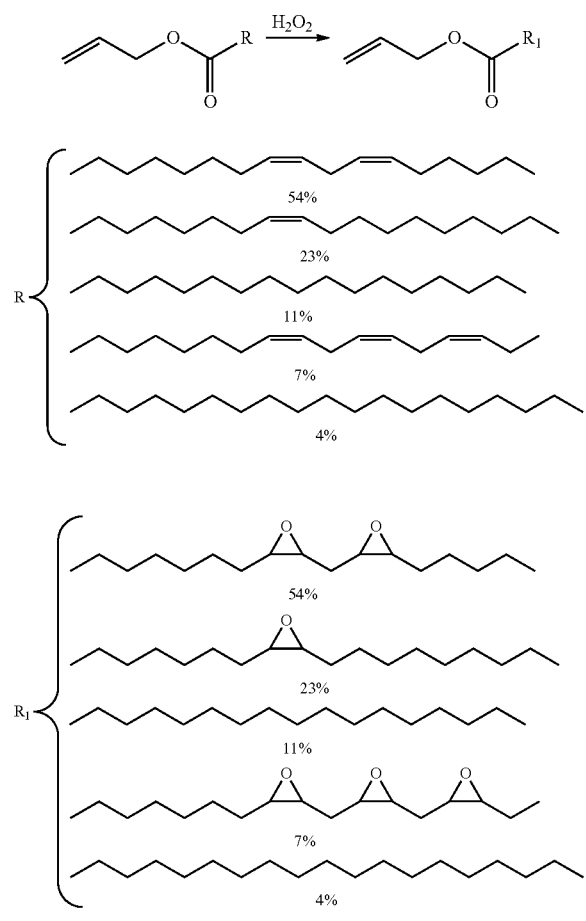

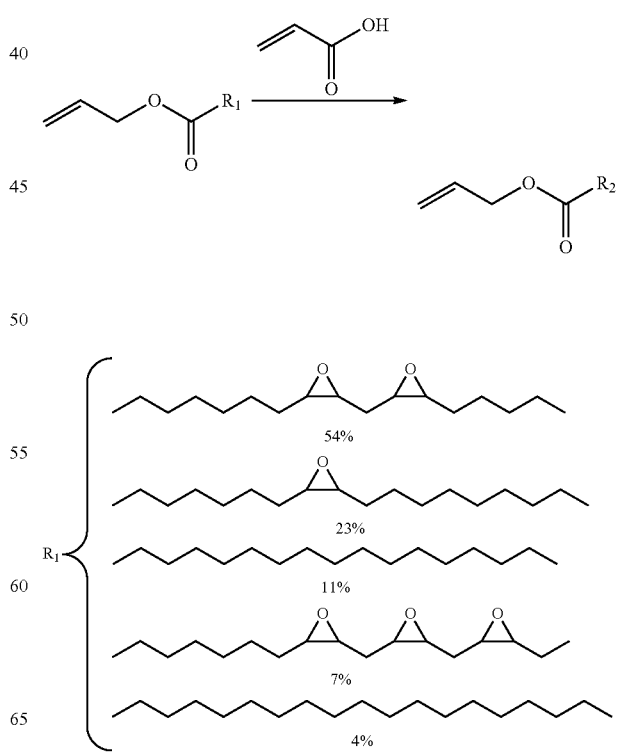

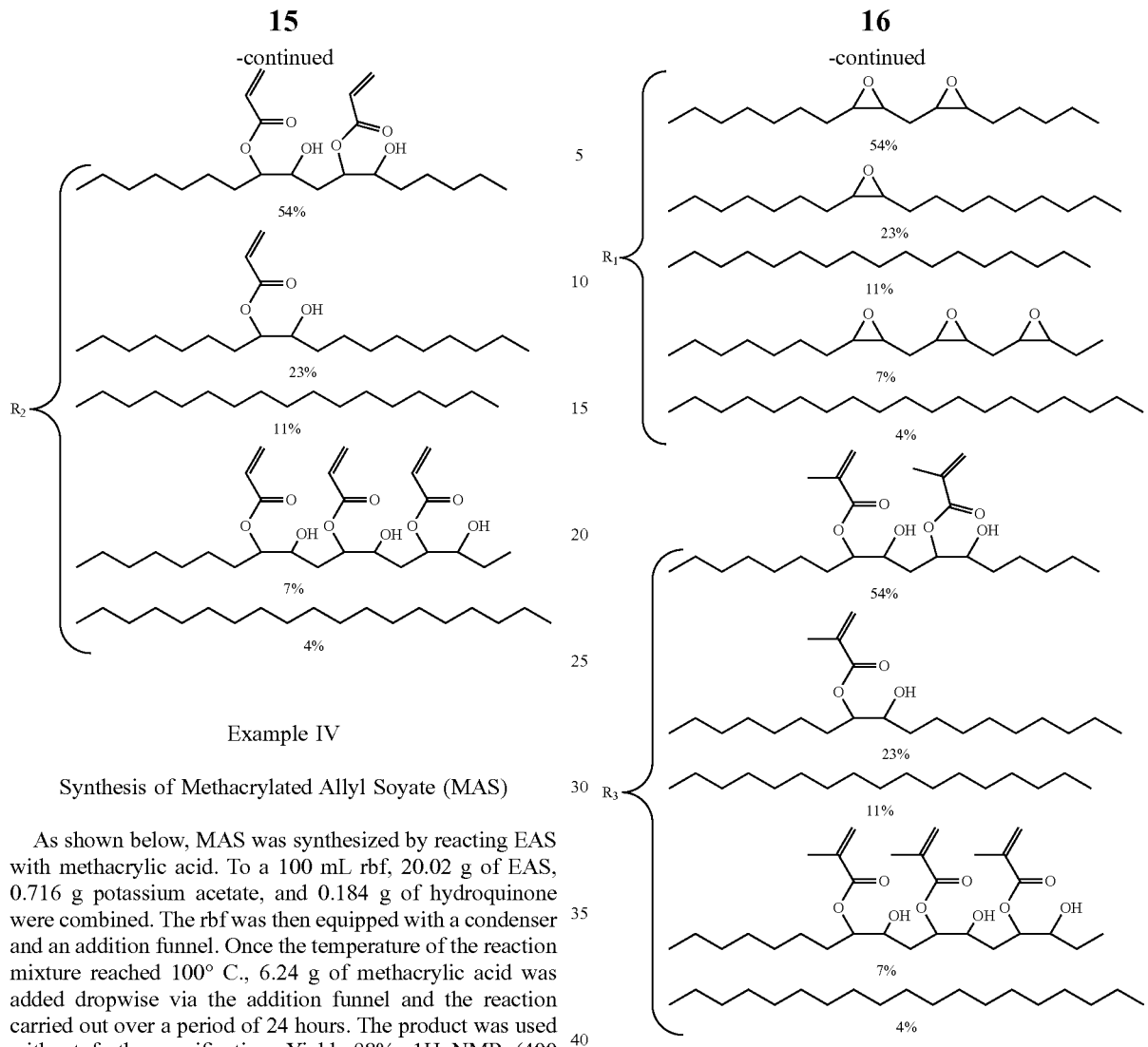

Example IV

Synthesis of Methacrylated Allyl Soyate (MAS)

As shown below, MAS was synthesized by reacting EAS with methacrylic acid. To a 100 mL rbf, 20.02 g of EAS, 0.716 g potassium acetate, and 0.184 g of hydroquinone were combined. The rbf was then equipped with a condenser and an addition funnel. Once the temperature of the reaction mixture reached 100° C., 6.24 g of methacrylic acid was added dropwise via the addition funnel and the reaction carried out over a period of 24 hours. The product was used without further purification. Yield: 98%. 1H NMR (400 MHz, CDCl$_3$, TMS): δ (ppm) 6.1-6.2 (dd, 1.5H, —C═OCH═CH$_2$), 5.85-5.97 (m, 2H, —OCH$_2$CH═CH$_2$); 5.45-5.67 (dd, 1.5H, —C═OCH═CH$_2$), 5.15-5.45 (m, 2.5H, CH$_2$CH═CH—CH$_2$—; —OCH$_2$CH═CH$_2$), 4.85 (1.5H—CH$_2$CHOC═O—), 4.54-4.58 (dt, 1.5H, —OCH$_2$CH═CH—), 3.7-4.0 (1.5H, —CHOH), 3.4-3.6 (1.5H, —CHOH), 2.32 (t, 2H, —C═OCH$_2$—), 1.90 (4.5H, CH$_2$═C(CH$_3$)C═O—), 1.16-1.88 (m, 23H, —C═OCH$_2$CH$_2$—; —CH$_2$CH$_2$CH$_2$—; —CH(O)CH$_2$CH$_2$—: —CH(O)CH$_2$CH(O)—), 0.96-0.87 (m, 3H, —CHCH$_3$). The viscosity of the product was determined to be 34.1 cP at a shear rate of 10 sec$^{-1}$ and temperature of 25° C.

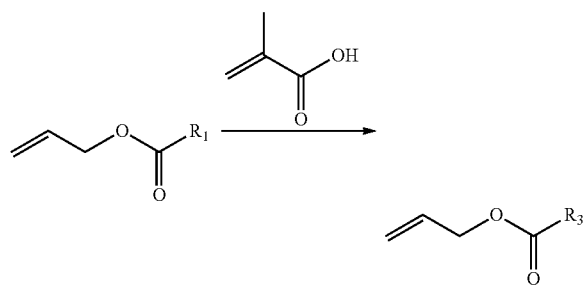

Example V

Synthesis of Highly Functionalized Methacrylated Allyl Soyate (HF-MAS)

As shown below, HF-MAS was synthesized by reacting epoxidized allyl soyate with methacrylic anhydride. To a 100 mL rbf, 10.08 g of EAS, 4.8 g of methacrylic anhydride, 0.15 g of ATC 3 catalyst (AMPAC™ Fine Chemicals), and 0.46 g of 2,6-di-t-butyl-4-methylphenol were combined. The reaction mixture was stirred at 100° C. for 48 hr. The product was used without further purification. Yield: 98%. 1H NMR (400 MHz, CDCl$_3$, TMS): δ (ppm) 6.1-6.2 (dd, 3H, —C═OCH═CH$_2$), 5.85-5.97 (m, 2H, —OCH$_2$CH═CH$_2$); 5.45-5.67 (dd, 3H, —C═OCH═CH$_2$), 5.15-5.45 (m, 2.5H, CH$_2$CH═CH—CH$_2$—; —OCH$_2$CH═CH$_2$), 4.85 (1.5H—CH$_2$CHOC═O—), 4.54-4.58 (dt, 3H, —OCH$_2$CH═CH—), 2.32 (t, 2H, —C═OCH$_2$—), 1.90 (9H, CH$_2$═C(CH$_3$)C═O—), 1.16-1.88 (m, 23H, ~C═OCH$_2$CH$_2$—; —CH$_2$CH$_2$CH$_2$—; —CH(O)CH$_2$CH$_2$—; —CH(O)CH$_2$CH(O)—), 0.96-0.87 (m, 3H, —CHCH$_3$). The viscosity of the product was determined to be 49.3 cP at a shear rate of 10 sec$^{-1}$ and temperature of 25° C.

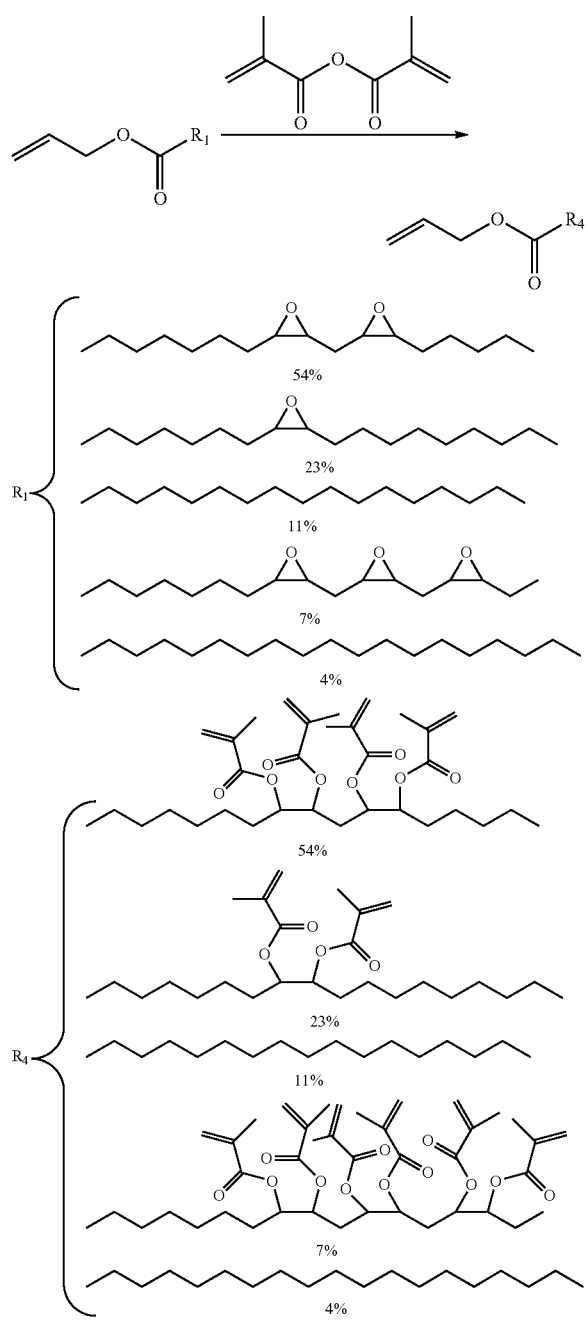

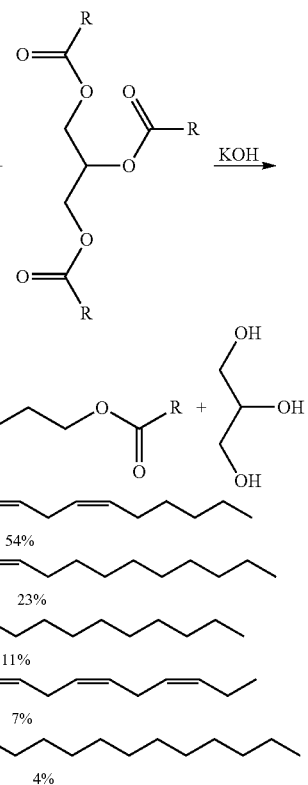

cooled to room temperature and then transferred to a 2 L separating funnel. To this mixture, 1 L of n-hexane was added and the resulting solution washed three times with 300 mL of acidic water (pH 3.5-4), once with deionized (DI) water (300 mL), and, finally, with brine solution (300 mL). The n-hexane layer was dried with $MgSO_4$ and solvent removed under vacuum at 35° C. and 100 bar pressure. The chemical composition of the product was confirmed using proton nuclear magnetic resonance spectroscopy (1H NMR). 1H NMR (400 MHz, $CDCl_3$, TMS): δ (ppm) 5.42-5.60 (q, 2H, $CH_3CH_2CH=CH-$), 5.20-5.42 (m, 3H, $-CH_2CH=CH-CH_2-$), 3.95-4.15 (t, 2H, $-OCH_2CH_2CH=CH-$), 2.68-2.84 (m, 1.3H, $=CHCH_2CH=$), 2.30-2.40 (q, 2H, $-OCH_2CH_2CH=CH-$), 2.20-2.30 (t, 2H, $-C=OCH_2-$). 1.93-2.22 (m, 5.3H, $-CH_2CH_2CH=$; $CH_3CH_2CH=CH-$), 1.57 (m, 2H, $-C=OCH_2CH_2-$), 1.29 (m, 17H, $-CH_2CH_2CH_2-$), 0.96-0.87 (m, 6H, $-CH_2CH_3$).

Example VI

Synthesis of 3-Hexenyl Soyate (3HS)

As shown below, 3HS was synthesized by the transesterification of SBO with 3H using KOH as the catalyst. KOH (7 g) was first heated at 140° C. for 30 minutes to remove adsorbed moisture and then cooled down to room temp by purging with $N_2$. Prior to the reaction, SBO (250 g) was deaerated by bubbled with $N_2$ for 30 minutes. The dried KOH and deaerated SBO were charged to a 1 L round bottom flask (RBF) equipped with a condenser and then 3H (250 g) was added. The reaction was carried out at 70° C. in a $N_2$ atmosphere for 3 hours. The reaction mixture was Example VII Synthesis of Epoxidized 3-Hexenyl Soyate (E3HS)

As shown below, E3HS was produced using hydrogen peroxide as the oxidation reagent. The procedure used was a follows: To a 1 L, two-neck RBF equipped with a condenser and an additional funnel, 3HS (180 g), acetic acid (49 g), and Amberlite® IR-120H (39.6 g) were combined and mixed well. $H_2O_2$ (220 mL, 50%) was added dropwise via the addition funnel and the reaction temperature maintained at 60° C. for 5 hours. After this period, the reaction mixture was allowed to cool to room temperature, transferred to a 2 L separatory funnel, and the bottom layer discarded. Next, 800 mL of ethyl acetate was added to the separatory funnel and the resulting solution washed three times with saturated NaHCO₃ solution (250 mL), followed by a brine wash (300 mL), and a final wash with DI water (300 mL). The ethyl acetate layer was dried with MgSO₄ and then solvent removed using vacuum at 35° C. and 100 bar pressure. Yield: 92%. 1H NMR (400 MHz, CDCl₃, TMS): δ (ppm) 3.95-4.15 (t, 2H, —OCH₂CH₂CH(O)CH—), 2.76-3.22 (m, 3H, —CH(O)CH—), 2.20-2.40 (t, 2H, —C=OCH₂—), 1.16-2.00 (m, 30H, —C=OCH₂CH₂—; —CH₂CH₂CH₂—; —CH(O)CH₂CH₂—; —CH(O)CH₂CH(O)—; CH₃CH₂CH(O)—), 0.96-0.87 (m, 6H, —CH₂CH₃).

solvent removed by vacuum stripping at 30° C. and 1 mbar. Yield: 94%. 1H NMR (400 MHz, CDCl₃, TMS): δ (ppm) 6.3-6.5 (m, 2.5H, C=OCH=CH₂); 6.1-6.2 (dd, 2.5H, —C=OCH=CH₂), 5.85-5.97 (m, 2.5 H, —C=OCH=CH₂); 4.85-4.95 (m, 2.5H, —C=OOCH—), 4.10-4.25 (m, 2H, —OCH₂CH₂—), 3.65-3.90 (2.5H, —CHOH), 3.4-3.6 (2.5H, —CHOH), 2.15-2.35 (t, 2H, —C=0CH₂—), 1.90-2.0 (m, 2H, —O—CH₂CH₂), 1.16-1.88 (m, 30H, —C=0CH₂CH₂—; —CH₂CH₂CH₂—; —CH₂CH₂—), 0.96-0.87 (m, 6H, —CH₂CH₃).

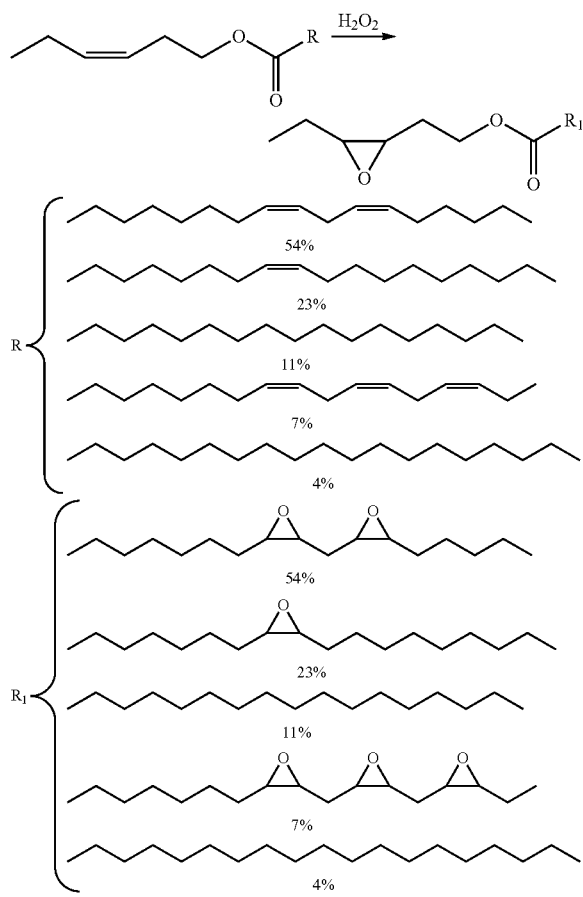

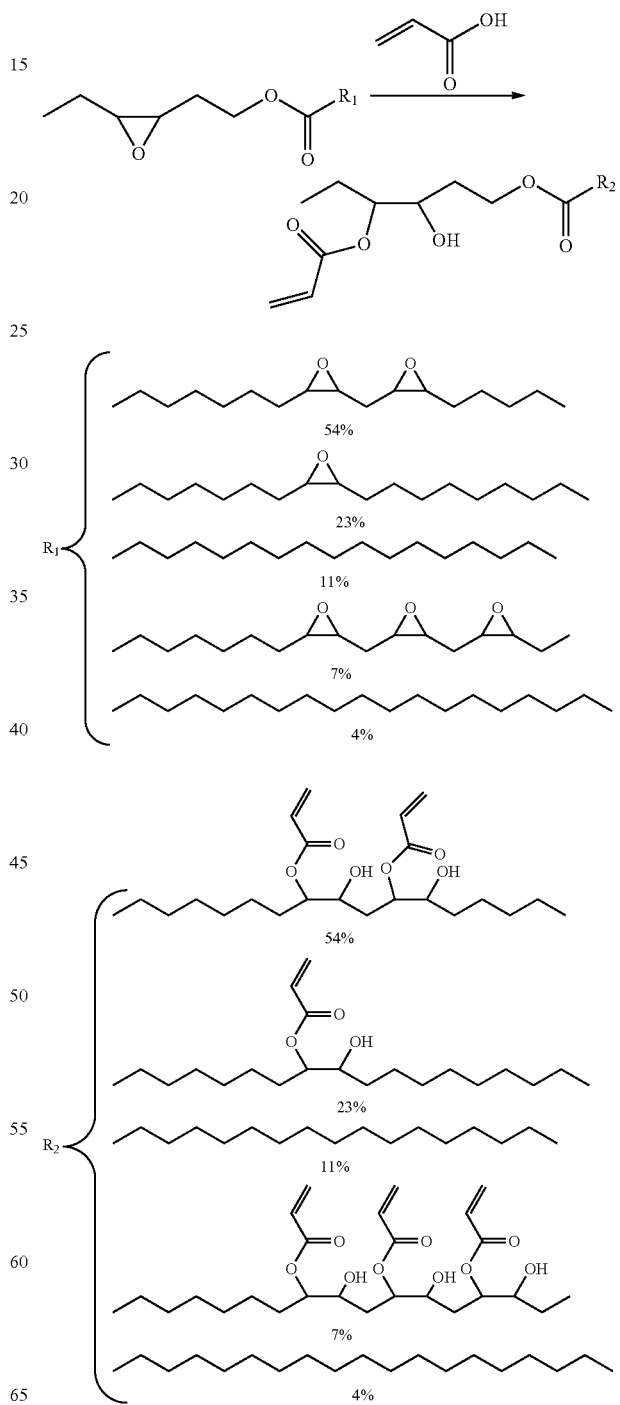

Example VIII

Synthesis of Acrylated 3-Hexenyl Soyate (A3HS)

As shown below, an acrylated derivative of 3HS was produced by reacting E3HS with AA. To a 1 L RBF equipped with a condenser and an addition funnel, 45.27 g of EPS, 1.36 g potassium acetate, 0.44 g of hydroquinone, and 200 ml of toluene were combined and the mixture heated to 90° C. Next, 17.16 g of AA was added dropwise via the addition funnel and the reaction carried out over a 24 hour period. After this period, the reaction mixture was allowed to cool to room temperature before transferring to a 2 L separating funnel and adding 500 mL of CH₂Cl₂. The solution was then washed three times with DI water (150 mL), twice with brine (200 mL), and finally with DI water (150 mL). The CH₂Cl₂ layer was dried with MgSO₄ and

Example IX

Comparative Example—Synthesis of n-Propyl Soyate (PS)

As shown below, PS was synthesized by transesterification of soybean oil with n-propanol. KOH (7 g) was first heated at 140° C. for 30 minutes to remove adsorbed moisture and then cooled down to room temp by purging with $N_2$. Prior to the reaction, SBO (250 g) was deaerated by bubbled with $N_2$ for 30 minutes. The dried KOH and deaerated SBO were charged to a 1 L round bottom flask (RBF) equipped with a condenser and then n-propyl soyate (250 g) was added. The reaction was carried out at 70° C. in a $N_2$ atmosphere for 3 hours. The reaction mixture was cooled to room temperature and then transferred to a 2 L separating funnel. To this mixture, 1 L of n-hexane was added and the resulting solution washed three times with 300 mL of acidic water (pH 3.5-4), once with deionized (DI) water (300 mL), and, finally, with brine solution (300 mL). The n-hexane layer was dried with $MgSO_4$ and solvent removed under vacuum at 35° C. and 100 mbar pressure. The chemical composition of the product was confirmed using proton nuclear magnetic resonance spectroscopy (1H NMR). Yield: 89%. 1H NMR (400 MHz, $CDCl_3$, TMS): δ (ppm) 5.25-5.45 (m, 3H, —$CH_2CH$=$CH$—$CH_2$—), 4.0 (dt, 2H, —$OCH_2CH_2CH_3$), 2.76 (m, 1.3H, =$CHCH_2CH$=), 2.32 (t, 2H, —C=$OCH_2$—). 2.03 (m, 3.4H, —$CH_2CH_2CH$=), 1.57 (m, 4H, —C=$OCH_2CH_2$—; —$OCH_2CH_2CH_3$), 1.29 (m, 17H, —$CH_2CH_2CH_2$—), 0.96-0.87 (m, 6H, —$CH_2CH_3$; —$OCH_2CH_2CH_3$).

Example X

Synthesis of Epoxidized n-Propyl Soyate (EPS)

Comparative Example

As shown below, EPS was produced using hydrogen peroxide as the oxidation reagent. The procedure used was a follows: To a 1 L, two-neck RBF equipped with a condenser and an additional funnel, PS (200 g), acetic acid (35.3 g), and Amberlite® IR-120H (28.5 g) were combined and mixed well. $H_2O_2$ (160 mL, 50%) was added dropwise via the addition funnel and the reaction temperature maintained at 60° C. for 5 hours. After this period, the reaction mixture was allowed to cool to room temperature, transferred to a 2 L separatory funnel, and the bottom layer discarded. Next, 800 mL of ethyl acetate was added to the separatory funnel and the resulting solution washed three times with saturated $NaHCO_3$ solution (250 mL), followed by a brine wash (300 mL), and a final wash with DI water (300 mL). The ethyl acetate layer was dried with $MgSO_4$ and then solvent removed using vacuum at 35° C. and 100 bar pressure. Yield: 94%. 1H NMR (400 MHz, $CDCl_3$, TMS): 4.0 (dt, 2H, —$OCH_2CH_2CH_3$), 2.76-3.22 (m, 3H, —CH(O) CH—), 2.20-2.40 (t, 2H, —C=$OCH_2$—), 1.16-1.95 (m, 25H, —C=$OCH_2CH_2$—; —$CH_2CH_2CH_2$—; —CH(O) $CH_2CH_2$—; —CH(O)$CH_2$CH(O)—; $CH_3CH_2CH_2$—), 0.96-0.87 (m, 6H, —$CH_2CH$; —$OCH_2CH_2CH_3$).

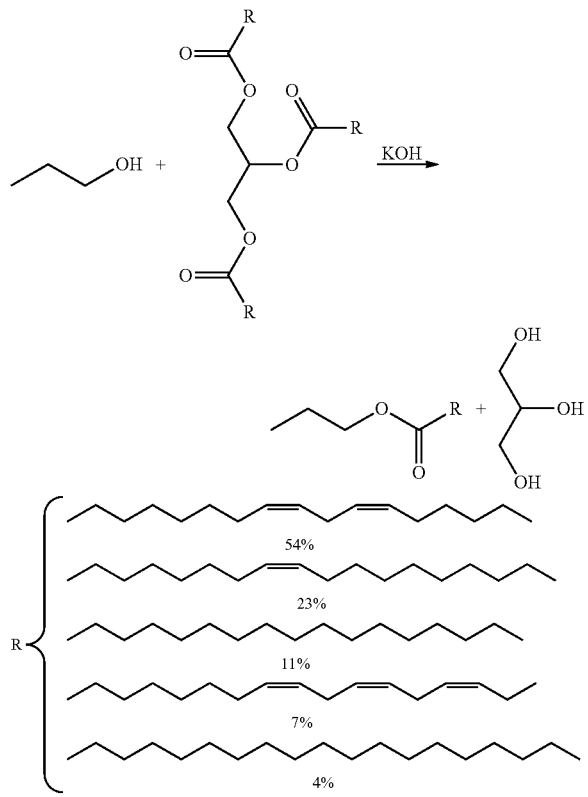

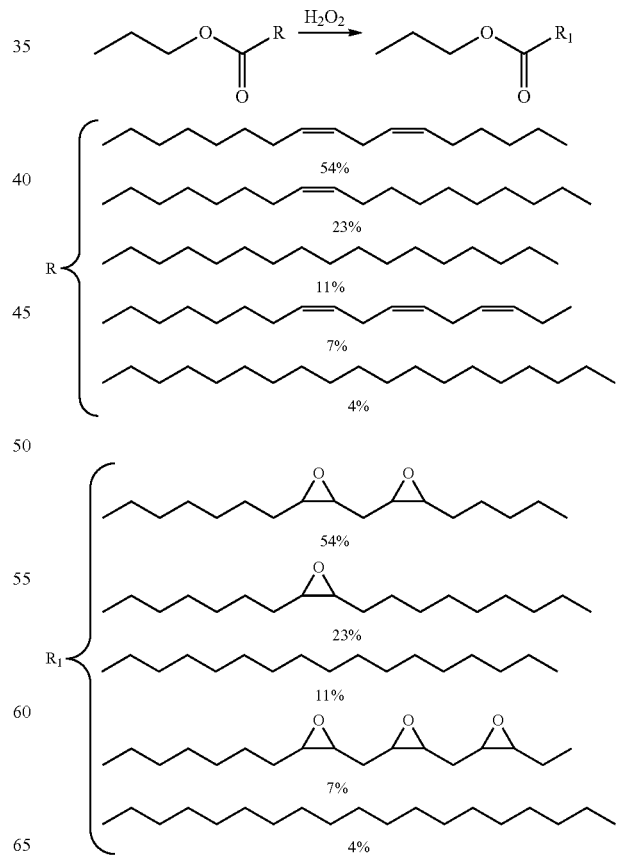

Example XI

Synthesis of Acrylated n-Propyl Soyate (APS)

Comparative Example

As shown below, APS was synthesized by reaction of EPS with acrylic acid. To a 1 L RBF equipped with a condenser and an additional funnel, 100 g of EPS, 3 g potassium acetate, and 0.65 g of hydroquinone were combined and the mixture heated to 100° C. Once the temperature of the reaction mixture reached 100° C., 25.7 g of AA was added dropwise via the addition funnel. The reaction was carried out over a 7 hour period. Once at room temperature, the reaction mixture was transferred to a 2 L separating funnel and 500 mL of n-hexane added. The reaction mixture was washed three times with DI water (150 mL), twice with brine (200 mL), and a finally with DI water (150 mL). The hexane layer was dried with $MgSO_4$ and solvent removed by vacuum stripping at 30° C. and 1 mbar. Yield: 97%. 1H NMR (400 MHz, $CDCl_3$, TMS): δ (ppm) 6.3-6.5 (m, 1.5H, C=OCH=$CH_2$); 6.1-6.2 (dd, 1.5H, —C=OCH=$CH_2$), 5.85-5.97 (m, 1.5 H, —C=OCH=$CH_2$); 4.85-4.95 (m, 1.5H, —C=OOCH—), 3.90-4.10 (dt, 2H, —$OCH_2CH_2CH_3$), 3.65-3.90 (1.5H, —CHOH), 3.4-3.6 (1.5H, —CHOH), 2.10-2.32 (t, 2H, —C=$0CH_2$—), 1.16-1.88 (m, 25H, —C=$0CH_2CH_2$—; —$CH_2CH_2CH_2$—; —$CH_2CH_2$—), 0.96-0.87 (m, 6H, —$CH_2CH_3$; —$OCH_2CH_2CH_3$).

Example XII

A Comparison of Ultraviolet Radiation Cured Coatings Based on AAS as Well as A3HS to Acrylated Soybean Oil (ASBO) and APS AAS, A3HS, ASBO, and APS were individually blended with the photoinitiator, Irgacure® 2022, at a concentration of 5 wt % with a FlackTek mixer using 3500 rpm for 5 minutes. Each sample solution were then coated on nine steel-Q panels, one glass panel, and one Teflon® coated glass panel using a drawdown bar with a 0.008 inch clearance. The films were passed under a F300 UVA lamp (Fusion UV systems) operating at a speed of 5 feet/min. The UVA light intensity was found to be 1410 $mW/cm^2$ as measured using a UV Power Puck® II (ETC Inc.). As indicated in Table 1, various measurements were carried out to characterize the coatings produced. The thickness of the cured coatings were determined using a PosiTest DFT® dry-thickness measurement gauge from DeFlesko Corporation. Chemical resistance was accessed using ASTM D 5402-93, which is typically referred to as the MEK (methyl ethyl ketone) double rub test. The hardness of the coatings were accessed using the König pendulum hardness test (ASTM D 4366-95). Impact resistance of coated panels was determined according to ASTM D 2794-93. Viscoelastic properties of cured free films were obtained using dynamic mechanical analysis (Q800 from TA Instruments). The free film specimens were obtained from the coatings cast over the Teflon coated glass panels. The measurements were carried out using the following parameters: temperature range −40° C. to 120° C., heating rate of 5° C./min., frequency 1 Hz, and strain amplitude of 0.02%. The glass transition temperature ($T_g$) was obtained from the peak maximum in the tan δ response. Mechanical properties were obtained from "dumb bell"-shaped free film specimens using an Instron tensile tester fitted with a 100 N load cell and the procedure outlined in ASTM D 638-5. The displacement rate of the movable clamp was set as 1 mm/minute. The data reported was the average of 5 replicate measurements. Table 1 lists the data obtained.

TABLE 1

Properties of coatings based on ASBO, APS, AAS, or A3HS with 5 weight percent Irgacure ® 2022.

| | ASBO | APS | AAS | A3HS |
|---|---|---|---|---|
| Viscosity* (cP) | 10,600 | 53 | 40 | 351 |
| Equivalent Weight (g/mole) | 284 | 270 | 181† | 233 |
| Average Thickness (μm) | 98 + 6 | 83 + 4 | 91 ± 4 | 89 ± 3 |
| Young's Modulus (MPa) | 453 + 9 | NA‡ | 33 ± 3 | 14 ± 1 |
| Elongation (%) | 7 + 1 | NA‡ | 12 ± 1 | 18 ± 1 |
| Storage modulus at 90° C. (MPa) | 46 | NA‡ | 5 | 6 |
| Tg from tan δ (° C.) | 45 | NA‡ | 6 | −1 |
| Pendulum Hardness (sec) | 50 ± 1 | 13 ± 0 | 23 ± 1 | 17 ± 0 |
| MEK Double Rubs | >1500 | 17 | 215 | 175 |

*Measured on the pure acrylate (no photoinitiator).
†Equivalent weight calculation included the allyl group.
‡Free film was too tacky to measure.

Example XIII

Coatings Based on ASBO as the Reactive Oligomeric Component and AAS or A3HS as the Reactive Diluent A description of the coatings compositions prepared is shown in Table 2. A detail procedure for the preparation APS/ASBO 25/75 is as follows: 3.56 g of APS, 10.69 g of ASBO, and 0.75 g of photoinitiator [Irgacure® 2022 (BASF, USA)] were mixed with a FlackTek mixer operating 3500 rpm for 5 minutes. This solution was then coated on nine steel-Q panels, one glass panel, and one Teflon coated glass panel using a drawdown bar with a 0.008 inch clearance. The films were passed under a F300 UVA lamp (Fusion UV systems) at 5 feet/min. The light intensity was found to be 1410 $mW/cm^2$ which was measured using UV Power Puck® II (ETC Inc.). For the other coatings, the procedure was the same with the exception that the quantity of the reagents was varied according to the information provided in Table 2.

TABLE 2

Composition of coatings based on ASBO as the reactive oligomeric component and AAS or A3HS as the reactive diluent. APS was included as a comparative example. All values are in grams.

| Coating Designation | APS | AAS | A3HS | ASBO | *PI |
|---|---|---|---|---|---|
| APS/ASBO 25/75 | 3.56 | — | — | 10.69 | 0.75 |
| AAS/ASBO 25/75 | — | 3.56 | — | 10.69 | 0.75 |
| A3HS/ASBO 25/75 | — | — | 3.56 | 10.69 | 0.75 |
| APS/ASBO 50/50 | 7.13 | — | — | 7.13 | 0.75 |
| AAS/ASBO 50/50 | — | 7.13 | — | 7.13 | 0.75 |
| A3HS/ASBO 50/50 | — | — | 7.13 | 7.13 | 0.75 |

*PI is the photoinitiator (Irgacure ® 2022).

As indicated in Table 3, various measurements were carried out to characterize the coatings produced. The thickness of the cured coatings was determined using a PosiTest DFT® dry-thickness measurement gauge from DeFlesko Corporation. Chemical resistance was accessed using ASTM D 5402-93, which is typically referred to as the MEK (methyl ethyl ketone) double rub test. The hardness of the coatings were accessed using the König pendulum hardness test (ASTM D 4366-95). Impact resistance of coated panels was determined according to ASTM D 2794-93. Viscoelastic properties of cured free films were obtained using dynamic mechanical analysis (Q800 from TA Instruments). The free film specimens were obtained from the coatings cast over the Teflon coated glass panels. The measurements were carried out using the following parameters: temperature range −40° C. to 120° C., heating rate of 5° C./min., frequency 1 Hz, and strain amplitude of 0.02%. The glass transition temperature ($T_g$) was obtained from the peak maximum in the tan δ response. Mechanical properties were obtained from "dumb bell"-shaped free film specimens using an Instron tensile tester fitted with a 100 N load cell and the procedure outlined in ASTM D 638-5. The displacement rate of the movable clamp was set as 1 mm/minute. The data reported was the average of 5 replicate measurements. Table 3 lists the data obtained.

TABLE 3

Data obtained for UV cured coatings of ASBO as the reactive oligomeric component and AAS or A3HS as the reactive diluents. APS was included as a comparative example.

|  | APS/ASBO 25/75 | AAS/ASBO 25/75 | A3HS/ASBO 25/75 | APS/ASBO 50/50 | AAS/ASBO 50/50 | A3HS/ASBO 50/50 |
| --- | --- | --- | --- | --- | --- | --- |
| Viscosity (cP) | 1,970 | 1,944 | 4,412 | 548 | 477 | 1,655 |
| Thickness (μm) | 81 ± 3 | 80 ± 2 | 93 ± 5 | 78 ± 3 | 79 ± 2 | 80 ± 3 |
| Young's Mod. (MPa) | 82 ± 3 | 438 ± 10 | 155 ± 9 | 20 ± 1 | 199 ± 12 | 57 ± 3 |
| Elongation (%) | 15 ± 2 | 7 ± 2 | 13 ± 0.4 | 14 ± 1 | 10.5 ± 3 | 17 ± 2 |
| *E' @ 90° C. (MPa) | 19 | 51 | 17 | 8 | 43 | 16 |
| Tg (° C.) | 23 | 57 | 35 | 14 | 52 | 21 |
| Pend. Hardness (sec) | 25 ± 0 | 41 ± 0 | 35 ± 0 | 23 ± 0 | 32 ± 1 | 21 ± 0 |
| Rev. Impact (in-lb) | 28 | 44 | 32 | 16 | 40 | 56 |
| MEK Double Rubs | 389 | >2,000 | 932 | 157 | 1,350 | 553 |

*E' indicates storage modulus.

Example XIV

Coatings Based on an Epoxy Acrylate as the Reactive Oligomeric Component and AAS or A3HS as the Reactive Diluent The epoxy acrylate (EA) utilized was CN121 from Sartomer. A description of the coating compositions prepared is shown in Table 4. A detail procedure for the preparation APS/EA 25/75 is as follows: 3.56 g of APS, 10.69 g of EA, and 0.75 g of photoinitiator [Irgacure® 2022 (BASF, USA)] were mixed with a FlackTek mixer operating at 3500 rpm for 5 minutes. This solution was then coated on nine steel-Q panels, one glass panel, and one Teflon coated glass panel using a drawdown bar with a 0.008 inch clearance. The films were passed under a F300 UVA lamp (Fusion UV systems) using a speed of 5 feet/min. The light intensity was found to be 1410 mW/cm$^2$ as measured using a UV Power Puck® II (ETC Inc.).

TABLE 4

Composition of coatings based on EA as the reactive oligomeric component and AAS or A3HS as the reactive diluent. APS was included as a comparative example. All values are in grams.

| Coating Designation | APS | AAS | A3HS | EA | PI* |
| --- | --- | --- | --- | --- | --- |
| APS/EA 25/75 | 3.56 | — | — | 10.69 | 0.75 |
| AAS/EA 25/75 | — | 3.56 | — | 10.69 | 0.75 |
| A3HS/EA 25/75 | — | — | 3.56 | 10.69 | 0.75 |
| APS/EA 50/50 | 7.12 | — | — | 7.12 | 0.75 |
| AAS/EA 50/50 | — | 7.12 | — | 7.12 | 0.75 |
| A3HS/EA 50/50 | — | — | 7.12 | 7.12 | 0.75 |

*PI is the photoinitiator (Irgacure® 2022).

Various experiments were carried out to characterize and analyze the coating as shown in Table 5. First, average thickness of all the coatings were measured and then characterized by MEK double rubs (ASTM D 5402-93), impact resistance (ASTM D 2794-93), and König pendulum hardness (ASTM D 4366-95). Dynamic mechanical analysis (Q800 from TA Instruments) was carried out using the film specimen prepared from the cured coating on the Teflon coated glass panel. The experiment was carried out using the following parameter: temperature range −40° C. to 120° C., heating rate of 5° C./min., frequency 1 Hz, and strain amplitude of 0.02%. The glass transition temperature ($T_g$) was obtained from the peak maximum in the tan δ response. The $T_g$ was reported from the thermogram obtained from the $2^{nd}$ heat. From the same panel dumb bell-shaped specimens were prepared for tensile testing (ASTM D 638-5) and measured using Instron tensile tester fitted with a 100 N load cell. The displacement rate of the movable clamp was set as 1 mm/minute. Data reported was the average of 5 replicate measurements. Table 5 list the data obtained for the cured coating.

TABLE 5

Data obtained for UV cured coatings of EA as the reactive oligomeric component and AAS or A3HS as the reactive diluents. APS was included as a comparative example.

| | APS/EA 25/75 | AAS/EA 25/75 | A3HS/EA 25/75 | APS/EA 50/50 | AAS/EA 50/50 | A3HS/EA 50/50 |
|---|---|---|---|---|---|---|
| Viscosity (cP) | 2869 | 2,048 | 5,387 | 541 | 440 | 1,644 |
| Thickness (μm) | 87 ± 4 | 94 ± 4 | 92 ± 5 | 86 ± 3 | 91 + 2 | 90 ± 4 |
| Young's Mod. (MPa) | NA | 26 ± 1 | 68 ± 15 | 10 ± 0 | 207 ± 33 | 22 ± 2 |
| Elongation (%) | NA | 40 ± 1 | 47 ± 4 | 27 ± 1 | 17 ± 2 | 27 ± 5 |
| *E' @ 90° C. (MPa) | NA | 31 | 19 | 7 | 26 | 18 |
| Tg (° C.) | NA | 24 | 17 | 10 | 22 | 14 |
| Pend. Hardness (sec) | NA | 38 ± 1 | 28 ± 1 | 17 ± 0 | 28 ± 1 | 17 ± 0 |
| Rev. Impact (in-lb) | NA | 160 | 152 | 64 | 88 | 92 |
| MEK Double Rubs | NA | 940 | 735 | 118 | 808 | 556 |

*E' indicates storage modulus

Example XV

Coatings Based on ASBO as the Reactive Oligomeric Component and MAS or HF-MAS as the Reactive Diluent A description of the coatings compositions prepared are shown in Table 6. A detail procedure for the preparation MAS/ASBO 50/50 is as follows: 7.13 g of MAS, 7.13 g of ASBO and 0.75 g of photoinitiator [Irgacure® 2022 (BASF, USA)] were mixed with a FlackTek mixer using 3500 rpm for 5 minutes. This solution was then coated on nine steel-Q panels, one glass panel, and one Teflon coated glass panel using a drawdown bar with a 0.008 inch clearance. The films were passed through F300 UVA lamp (Fusion UV systems) UV light at 5 feet/min speed which is equipped with a conveyor belt set. The light intensity was found to be 1410 mW/cm$^2$ which was measured by UV Power Puck® II (ETC Inc.).

TABLE 6

Composition of coatings based on ASBO as the reactive oligomeric component and MAS or HF-MAS as the reactive diluents. APS was included as a comparative example. All values are in grams.

| Coating Designation | MAS | HF-MAS | ASBO | PI |
|---|---|---|---|---|
| MAS/ASBO 50/50 | 7.13 | — | 7.13 | 0.75 |
| HF-MAS/ASBO 50/50 | — | 7.13 | 7.13 | 0.75 |

Various experiments were carried out to characterize and analyze the coating as shown in Table 7. First, average thickness of all the coatings were measured and then characterized by MEK double rubs (ASTM D 5402-93), impact resistance (ASTM D 2794-93), and König pendulum hardness (ASTM D 4366-95). Dynamic mechanical analysis (Q800 from TA Instruments) was carried out using the film specimen prepared from the cured coating on the Teflon coated glass panel. The experiment was carried out using the following parameter: temperature range −40° C. to 120° C., heating rate of 5° C./min., frequency 1 Hz, and strain amplitude of 0.02%. The glass transition temperature ($T_g$) was obtained from the peak maximum in the tan δ response. The $T_g$ was reported from the thermogram obtained from the 2$^{nd}$ heat. From the same panel dumb bell-shaped specimens were prepared for tensile testing (ASTM D 638-5) and measured using Instron tensile tester fitted with a 100 N load cell. The displacement rate of the movable clamp was set as 1 mm/minute. Data reported was the average of 5 replicate measurements. Table 7 lists the data obtained for the cured coating.

TABLE 7

Data obtained for UV cured coatings of ASBO as the reactive oligomeric component and MAS or HF-MAS as the reactive diluents

| Property | MAS/ASBO 50/50 | HF-MAS/ASBO 50/50 |
|---|---|---|
| Average Thickness (μm) | 94 ± 5 | 98 + 6 |
| Viscosity (cP) | 439 | 595 |
| Young's Modulus (MPa) | 320 ± 10 | 721 ± 25 |
| Elongation (%) | 4.9 ± 0.3 | 2.6 ± 0.2 |
| Storage modulus at 90° C. (MPa) | 38 | 100 |
| Tg from tan δ (° C.) | 48 | 62 |
| Pendulum Hardness (sec) | 46 ± 1 | 72 ± 2 |
| MEK Double Rubs | 480 ± 15 | >1,200 |

Example XVI

Synthesis of Soyate-Functionalized Polysiloxane

As shown below, a soyate-functionalized polysiloxanes was produced by reacting allyl soyate (R represents alkyl chains derived from soybean oil fatty acid ester groups) with methylhydrosiloxane-dimethylsiloxane copolymers, polymethylhydrosiloxanes or hydride POSS via hydrosilation reaction. In a 40 mL vial, 1.51 g of allyl soyate, 15 mL of chloroform, and 80 μL of Karstedt catalyst (2% Pt) were mixed followed by addition of 5.56 g of HMS-064. The vial was sealed and solution was allowed to react at 60° C. for 6 hours. Then the product was precipitated into 60 mL of methanol and washed two times with methanol. The remaining solvent was removed by vacuum stripping at 40° C. $^1$H NMR (400 MHz, CDCl$_3$, TMS): δ (ppm) 5.2-5.4 (m, CH$_2$CH=CH—CH$_2$—), 4.0 (t, —OCH$_2$CH$_2$CH$_2$—) 2.7-2.8 (m, =CH$_2$CH$_2$CH=), 2.2-2.35 (m, —C=0CH$_2$—), 1.95-2.05 (m, —CH$_2$CH$_2$CH=), 1.5-1.7 (m, —C=0CH$_2$CH$_2$—, OCH$_2$CH$_2$CH$_2$Si), 1.15-1.4 (m, —CH$_2$CH$_2$CH$_2$—), 0.95-0.8 (m, —CHCH$_3$), 0.55 (t, —SiCH$_2$CH$_2$—), 0.35-0 (m, SiCH$_3$).

Analogously, a number of other available siloxane compounds containing hydride groups have been modified.

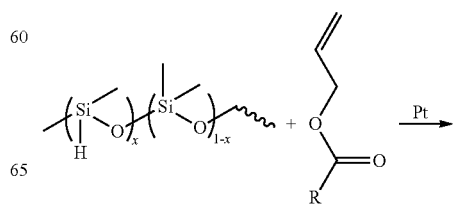

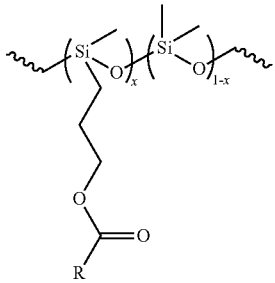

Example XVII

Coating Preparation

As prepared allyl-functionalized siloxane components, 25 wt. % in chloroform, were mixed in various ratios with auto-oxidation catalyst package (0.84 mg of cobalt octoate, 5.54 mg of zirconium octoate, and 50 mg of Nuxtra Zinc per gram of solids). The formulations allowed tough hydrophobic coatings upon drying at atmospheric conditions.

Example XVIII

Novel Soybean Oil-Derived Acrylates for UV-Curable Coatings

Abstract

Acrylate-functional soybean oil (ASBO) has been commercialized for applications such as photocurable coatings and thermoset composites. Since the viscosity ASBO is relatively high, a reactive diluent is required to produce photocurable compositions that are processable and essentially free of volatile organic compounds. Since most all reactive diluents are derived from petroleum and coatings with high renewable contents are desired, there is a need for new reactive diluents based on renewable resources. Five SBO-based acrylates/methacrylates were synthesized and investigated as reactive diluents for free radical photocurable coatings. The general synthetic procedure involved transesterification of SBO with either allyl alcohol or cis-3-hexen-1-ol to produce allyl soyate (AS) and cis-3-hexenyl soyate (3HS), respectively. AS and 3HS were then epoxidized using hydrogen peroxide as the oxidation reagent. For AS, epoxidization occurred exclusively at the disubstituted double bonds derived from SBO, leaving the terminal double bonds derived from allyl alcohol intact. The epoxy derivative of AS (EAS) was treated with acrylic acid to produce an acrylated derivative referred to as acrylated AS (AAS). EAS was also treated with methacrylic acid to produce a methacrylate derivative referred to as methacrylated AS (MAS) as well as with and excess methacrylic anhydride to produce a compound referred to as highly functionalized MAS (HF-MAS). The difference in chemical structure between MAS and HF-MAS is based on the number of methacrylate groups per molecule. For MAS, the average number of methacrylate groups per molecule was 1.5 while the average number of methacrylate groups per molecule for HF-MAS was 3. Epoxidized 3HS was treated with acrylic acid to produce an acrylate derivative referred to as acrylated 3HS (A3HS). For comparison purposes, acrylated n-propyl soyate (APS) was also produced by using an analogous process in which n-propanol was used for the transesterification of SBO. The only difference in chemical structure between AAS and APS is that AAS possesses and allyl group in place of the propyl group present in APS. It was thought that by comparing properties between coatings based on APS to analogs based on AAS, it would be possible to determine if the allyl group in AAS is reactive enough to contribute to the formation of the crosslinked network. Whereas the viscosity of ASBO was found to be 10,600 cP at 25° C., the viscosities of all five of the SBO-based reactive diluent candidates were found to be much lower. In fact, the viscosity of APS, AAS, MAS, HF-MAS, and A3HS were determined to be 53, 40, 34, 49, and 351 cP, respectively.

Photocurable coatings were prepared that involved blends of each of the SBO-based reactive diluent candidates with ASBO and coating rheological, physical, and mechanical properties determined. In addition, a series of coatings was also produced in which ASBO was replaced by an acrylated vinyl ether polymer based on SBO and coatings properties characterized. A comparison of properties of coatings based on AAS as the reactive diluent to analogous coatings based on APS clearly indicated that the allyl group present in AAS contributed to the development of the crosslinked network. The use of AAS provided coatings that possessed significantly higher chemical resistance, glass transition temperature (Tg), Young's modulus, hardness, and storage modulus above Tg as compared to those coatings based on APS. Of the five SBO-based reactive diluents produced for the study, HF-MAS enabled by far the hardest, highest modulus, highest Tg coating films. This result was attributed to the exceptionally low methacrylate equivalent weight of HF-MAS. Overall, AAS, A3HS, and HF-MAS were shown to possess significant potential as new reactive diluents based on renewable resources. Photo-curable compositions based on these SBO-based reactive diluents in conjunction with ASBO exhibited useful properties with renewable contents as high as 89 weight percent.

Introduction

Since fossil resources are limited and the vast majority of compounds produced by the chemical industry are derived from petroleum, there is a major need to develop new cost-effective chemicals based on renewable resources. In fact, the United States Department of Energy has a goal of producing at least 10% of basic chemical building blocks from plant-derived renewables by 2020 (www.nrel.gov/docsilegosti/fy98/24216.pdf). As of 1998, the volume of chemicals produced from renewable resources was just 2%. The primary feedstocks for renewable-based chemicals include wood, polysaccharides, sugars, and plant oils. Of these, plant oils are particularly useful since they can be easily isolated and derivatized to produce a variety of useful chemicals. Historically, plant oils have been used in paints since prehistoric times (Wicks et al., *Organic Coatings: Science and Technology*, 3rd ed., pp. 295. John Wiley & Sons, Hoboken, N.J., 2007). The utility of plant oils in coating applications is largely due to the unsaturation present in the plant oil triglycerides that enable crosslinking of the oil into an insoluble, solid film. Since the level of triglyceride unsaturation is dependent on source of the plant oil, not all plant oils are useful for coating applications. The most abundant cost effect plant oils are palm oil and soybean oil (SBO). Palm oil has a relatively low level of unsaturation, while SBO has a moderate degree of unsaturation. On average, palm oil triglycerides possess 1.8 double bonds per molecule, while SBO possesses approximately 4.5 doubles per molecule. Considering this fact, it can be easily understood that SBO is a prime feedstock for coating applications. The chemical structure of the SBO triglyceride is shown below:

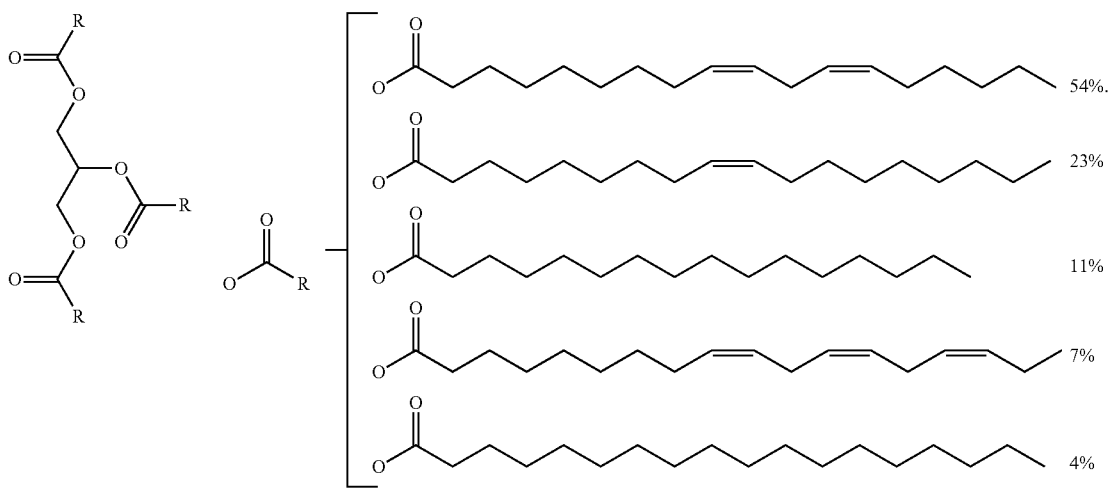

Initial coating applications for plant oils have involved crosslinking (i.e. curing) through an oxidative process typically referred to as autoxidation (nrel.gov/docs/legosti/fy98/24216.pdf; Wicks et al., Organic Coatings: Science and Technology, 3rd ed., pp. 295. John Wiley & Sons, Hoboken, N.J., 2007; Mallegol et al., 2000 Prog. Org. Coat., 39 107-113; Mallegol et al., 1999 J. Am. Oil Chem. Soc., 76 967-976). Over the past few decades, derivatization of the double bonds to other functional groups have been utilized to extend the utility of plant oils for material applications. Most of the derivatization methods involve epoxidation of the double bonds (Kouroosh et al., 2012 Ann. Biol. Res., 3 4254-4258). The epoxidized derivative, which is commercially available, can be crosslinked using anhydride-functional curing agents or by cationic polymerization of the epoxide groups (Tan et al., 2013 Ind. Crop. Prod., 43 378-385; Samper et al., 2012 J. Am. Oil Chem. Soc., 89 1521-1528; Thames et al., 1999 Surf Coat. Technol., 115 208-214). The epoxide groups can be further derivatized to hydroxyl functionality by hydrolysis or alcoholysis of the epoxide groups (Wang et al., 2009 J. Appl. Polvm. Sci., 114 125-131). Similar to epoxidized soybean oil, hydroxyl-functional soybean oil is commercially available. Soybean oil polyols have been extensively investigated for the production of polyurethanes (Petrovic, 2008 Polym. Rev., 48 109-155). From the epoxidized derivative, acrylate or methacrylate derivatives can be produced by epoxy ring-opening reactions using acrylic or methacrylic acid, respectively (Bajpai et al., 2004 Pigm. Resin Technol., 33 160-164). Acrylate and methacrylate-functional soybean oil have been used to produce crosslinked networks by a free radical polymerization mechanism (Kim et al., 2010 J. Polvm. Environ., 18 291-297; Fu et al., 2010 J. Appl. Polym. Sci., 117 2220-2225; Aakesson et al., 2009 J. Appl. Polym. Sci., 114 2502-2508). Acrylate-functional soybean oil is commercially available and marketed as a building block for photocurable coatings.

Due to their essentially negligible volatile organic compound (VOC) content, low energy consumption, and fast cure speed, photocurable coatings have become a very important class of materials. Photocurable materials are used to coat heat sensitive substrates such as plastics, paper, and wood. They are also used for the production of printing inks, optical fibers, adhesives, and dental composites. The three primary components of a photopolymerizable coating are the photoinitiator, reactive diluent, and a reactive oligomer. The reactive diluent is typically a relatively low molecular weight, low viscosity, liquid with at least one reactive group. The primary function of the reactive diluent is to provide low enough viscosity to the coating to enable effective processing without introducing VOCs. Since the reactive diluent becomes part of the cured coating, it contributes to the physical and mechanical properties of the coating. For protective coatings, the reactive diluent typically has at least two reactive groups per molecule. A higher number of functional groups per molecule provides higher crosslink densities which typically translates to higher coating modulus, hardness, abrasion resistance, and chemical resistance. For free radical photocurable coatings, acrylate reactive diluents are commercially available that possess as many as four acrylate groups per molecule. The reactive oligomer component of a photocurable coating is typically required to provide toughness and substrate adhesion. The higher molecular weight of the reactive oligomer minimizes shrinkage upon curing enabling better adhesion to the substrate and higher impact strength. Acrylate oligomers derived from urethanes, polyesters, and epoxy resins are commercially available. Commercially available acrylate oligomers possess at least two acrylate groups per molecule with some possessing as many as six acrylate groups per molecule.

As mentioned previously in this document, a SBO derivative with acrylate groups (ASBO) is commercially available. For photocurable coatings, ASBO would be expected to serve as the reactive oligomer since it is quite viscose and, as result, would need to be blended with a reactive diluent to meet viscosity requirements. Blending ASBO with a reactive diluent reduces the overall renewable content of the coating since most all commercially available reactive diluents are petroleum-based. As a result, there is a need for reactive diluents that are based on renewable building blocks. To illustrate the market need for coatings with high renewable content, the USDA BioPreferred® program can be considered. This program requires that federal agencies give preferential consideration to products that meet or exceed a minimum renewable content. The minimum renewable content has been set by the USDA and varies with the end-use application. For example, the minimum renewable content for water tank coatings has been set at 59%, while that for roof coatings is 20% (www.biopreferred.gov/Default.aspx). This document describes a new approach for producing novel acrylates and methacrylates based on SBO that may be very useful as reactive diluents. The novel SBO-based reactive diluents were used to produce photocurable coatings that possess exceptionally high renewable content.

Experimental

Materials. Table 8 provides a description of all the starting materials used for the study.

TABLE 8

A description of all the starting materials used for the study.

| Chemical | Designation | Vendor |
|---|---|---|
| Soybean oil | SBO | Sam's Club |
| Acrylated soybean oil | ASBO | Cytec |
| Allyl alcohol | ALA | Sigma-Aldrich |
| cis-3-Hexen-1-ol | 3H | Sigma-Aldrich |
| Potassium hydroxide | KOH | Sigma-Aldrich |
| n-Hexane | n-Hexane | Sigma-Aldrich |
| n-Propanol | nP | Sigma-Aldrich |
| Magnesium sulfate | $MgSO_4$ | Sigma-Aldrich |
| Acetic acid | Acetic acid | Sigma-Aldrich |
| Acidic ion-exchange resin | Amberlite ® IR-120H | Sigma-Aldrich |
| Hydrogen peroxide (50 wt % in water) | $H_2O_2$ | Sigma-Aldrich |
| ethyl acetate | ethyl acetate | BDH Chemicals |
| Sodium bicarbonate, ACS grade | $NaHCO_3$ | Amresco Inc. |
| Acrylic acid | AA | Sigma-Aldrich |
| Potassium acetate | potassium acetate | Sigma-Aldrich |
| Methacrylic acid | MA | Sigma-Aldrich |
| Toluene | Toluene | BDH Chemicals |
| IRGACURE ® 2022 | PI | BASF |
| 1,2-Dichloromethane | $CH_2Cl_2$ | Alfa Aesar |
| Hydroquinone | hydroquinone | Sigma-Aldrich |
| Methacrylic anhydride | Methacrylic anhydride | Sigma-Aldrich |
| ATC 3 ®, AFC Accelerators | ATC 3 catalyst | AMPAC ™ Fine Chemicals |
| 2,6-di-t-butyl-4-methylphenol | 2,6-di-t-butyl-4-methylphenol | Sigma-Aldrich |

Synthesis of Allyl Soyate (AS). AS was synthesized by the transesterification of SBO with ALA using KOH as the catalyst. KOH (7 g) was first heated at 140° C. for 30 minutes to remove adsorbed moisture and then cooled down to room temp by purging with $N_2$. Prior to the reaction, SBO (250 g) was deaerated by bubbled with $N_2$ for 30 minutes. The dried KOH and deaerated SBO were charged to a 1 L round bottom flask (RBF) equipped with a condenser and then ALA (165 g) was added. The reaction was carried out at 70° C. in a $N_2$ atmosphere for 3 hours. The reaction mixture was cooled to room temperature and then transferred to a 2 L separating funnel. To this mixture, 1 L of n-hexane was added and the resulting solution washed three times with 300 mL of acidic water (pH 3.5-4), once with deionized (DI) water (300 mL), and, finally, with brine solution (300 mL). The n-hexane layer was dried with $MgSO_4$ and solvent removed under vacuum at 35° C. and 100 bar pressure. The chemical composition of the product was confirmed using proton nuclear magnetic resonance spectroscopy (1H NMR). 1H NMR (400 MHz, $CDCl_3$, TMS): δ (ppm) 5.85-5.97 (m, 1H, —$OCH_2CH$=$CH_2$), 5.15-5.45 (m, 2.5H, $CH_2CH$=$CH$—$CH_2$—; —$OCH_2CH$=$CH_2$), 4.54-4.58 (dt, 2H, —$OCH_2CH$=$CH$—) 2.76 (m, 1.3H, =$CHCH_2CH$=), 2.32 (t, 2H, —C=$0CH_2$—). 2.03 (m, 3.4H, —$CH_2CH_2CH$=), 1.57 (m, 2H, —C=$OCH_2CH_2$—), 1.29 (m, 16H, —$CH_2CH_2CH_2$—), 0.96-0.87 (m, 3H, —$CHCH_3$).

Synthesis of 3-Hexenyl Soyate (3HS). 3HS was synthesized by the transesterification of SBO with 3H using KOH as the catalyst. KOH (7 g) was first heated at 140° C. for 30 minutes to remove adsorbed moisture and then cooled down to room temp by purging with $N_2$. Prior to the reaction, SBO (250 g) was deaerated by bubbled with $N_2$ for 30 minutes. The dried KOH and deaerated SBO were charged to a 1 L round bottom flask (RBF) equipped with a condenser and then 3H (250 g) was added. The reaction was carried out at 70° C. in a $N_2$ atmosphere for 3 hours. The reaction mixture was cooled to room temperature and then transferred to a 2 L separating funnel. To this mixture, 1 L of n-hexane was added and the resulting solution washed three times with 300 mL of acidic water (pH 3.5-4), once with deionized (DI) water (300 mL), and, finally, with brine solution (300 mL). The n-hexane layer was dried with $MgSO_4$ and solvent removed under vacuum at 35° C. and 100 bar pressure. The chemical composition of the product was confirmed using proton nuclear magnetic resonance spectroscopy (1H NMR). 1H NMR (400 MHz, $CDCl_3$, TMS): δ (ppm) 5.42-5.60 (q, 2H, $CH_3CH_2CH$=$CH$—), 5.20-5.42 (m, 3H, —$CH_2CH$=$CH$—$CH_2$—), 3.95-4.15 (t, 2H, —$OCH_2CH_2CH$=$CH$—), 2.68-2.84 (m, 1.3H, =$CHCH_2CH$=), 2.30-2.40 (q, 2H, —$OCH_2CH_2CH$=$CH$—), 2.20-2.30 (t, 2H, —C=$OCH_2$—). 1.93-2.22 (m, 5.3H, —$CH_2CH_2CH$=; $CH_3CH_2CH$=$CH$—), 1.57 (m, 2H, —C=$OCH_2CH_2$—), 1.29 (m, 17H, —$CH_2CH_2CH_2$—), 0.96-0.87 (m, 6H, —$CH_2CH_3$).

Synthesis of n-Propyl Soyate (PS). PS was synthesized by the transesterification of SBO with nP using KOH as the catalyst. KOH (7 g) was first heated at 140° C. for 30 minutes to remove adsorbed moisture and then cooled down to room temp by purging with $N_2$. Prior to the reaction, SBO (250 g) was deaerated by bubbled with $N_2$ for 30 minutes. The dried KOH and deaerated SBO were charged to a 1 L round bottom flask (RBF) equipped with a condenser and then nP (250 g) was added. The reaction was carried out at 70° C. in a $N_2$ atmosphere for 3 hours. The reaction mixture was cooled to room temperature and then transferred to a 2 L separating funnel. To this mixture, 1 L of n-hexane was added and the resulting solution washed three times with 300 mL of acidic water (pH 3.5-4), once with deionized (DI) water (300 mL), and, finally, with brine solution (300 mL). The n-hexane layer was dried with $MgSO_4$ and solvent removed under vacuum at 35° C. and 100 mbar pressure. The chemical composition of the product was confirmed using proton nuclear magnetic resonance spectroscopy (1H NMR). Yield: 89%. 1H NMR (400 MHz, CDCl$_3$, TMS): δ (ppm) 5.25-5.45 (m, 3H, —CH$_2$CH=CH—CH$_2$—), 4.0 (dt, 2H, —OCH$_2$CH$_2$CH$_3$), 2.76 (m, 1.3H, =CHCH$_2$CH=), 2.32 (t, 2H, —C=OCH$_2$—), 2.03 (m, 3.4H, —CH$_2$CH$_2$CH=), 1.57 (m, 4H, —C=OCH$_2$CH$_2$—; —OCH$_2$CH$_2$CH$_3$), 1.29 (m, 17H, —CH$_2$CH$_2$CH$_2$—), 0.96-0.87 (m, 6H, —CH$_2$CH; —OCH$_2$CH$_2$CH$_3$).

Synthesis of Epoxidized AS (EAS). EAS was produced using hydrogen peroxide as the oxidation reagent. With the process utilized, only the internal double bonds derived from the SBO were epoxidized. The procedure used was a follows: To a 1 L, two-neck RBF equipped with a condenser and an additional funnel, AS (180 g), acetic acid (31.8 g), and AMBERLITEt IR-120H (25.6 g) were combined and mixed well. H$_2$O$_2$ (145 mL, 50%) was added dropwise via the addition funnel and the reaction temperature maintained at 60° C. for 5 hours. After this period, the reaction mixture was allowed to cool to room temperature, transferred to a 2 L separatory funnel, and the bottom layer discarded. Next, 800 mL of ethyl acetate was added to the separatory funnel and the resulting solution washed three times with saturated NaHCO$_3$ solution (250 mL), followed by a brine wash (300 mL), and a final wash with DI water (300 mL). The ethyl acetate layer was dried with MgSO$_4$ and then solvent removed using vacuum at 35° C. and 100 bar pressure. Yield: 95%. 1H NMR (400 MHz, CDCl$_3$, TMS): δ (ppm) 5.85-5.97 (m, 1H, —OCH$_2$CHCH=CH$_2$), 5.15-5.45 (m, 2.5H, CH$_2$CH=CH—CH$_2$—; —OCH$_2$CH=CH$_2$), 4.54-4.58 (dt, 2H, —OCH$_2$CH=CH—) 2.76-3.22 (m, 3H, —CH(O)CH—), 2.32 (t, 2H, —C=0CH$_2$—), 1.16-1.88 (m, 23H, —C=OCH$_2$CH$_2$—; —CH$_2$CH$_2$CH$_2$—; —CH(O)CH$_2$CH$_2$—; —CH(O)CH$_2$CH(O)—), 0.96-0.87 (m, 3H, —CHCH$_3$).

Synthesis of Epoxidized 3HS (E3HS). E3HS was produced using hydrogen peroxide as the oxidation reagent. The procedure used was a follows: To a 1 L, two-neck RBF equipped with a condenser and an additional funnel, 3HS (180 g), acetic acid (49 g), and AMBERLITE® IR-120H (39.6 g) were combined and mixed well. H$_2$O$_2$ (220 mL, 50%) was added dropwise via the addition funnel and the reaction temperature maintained at 60 OC for 5 hours. After this period, the reaction mixture was allowed to cool to room temperature, transferred to a 2 L separatory funnel, and the bottom layer discarded. Next, 800 mL of ethyl acetate was added to the separatory funnel and the resulting solution washed three times with saturated NaHCO$_3$ solution (250 mL), followed by a brine wash (300 mL), and a final wash with DI water (300 mL). The ethyl acetate layer was dried with MgSO$_4$ and then solvent removed using vacuum at 35° C. and 100 bar pressure. Yield: 92%. 1H NMR (400 MHz, CDCl$_3$, TMS): δ (ppm) 3.95-4.15 (t, 2H, —OCH$_2$CH$_2$CH(O)CH—), 2.76-3.22 (m, 3H, —CH(O)CH—), 2.20-2.40 (t, 2H, —C=OCH$_2$—), 1.16-2.00 (m, 30H, —C=OCH$_2$CH$_2$—; —CH$_2$CH$_2$CH$_2$—; —CH(O)CH$_2$CH$_2$—; —CH(O)CH$_2$CH(O)—; CH$_3$CH$_2$CH(O)—), 0.96-0.87 (m, 6H, —CH$_2$CH$_3$).

Synthesis of Epoxidized PS (EPS). EPS was produced using hydrogen peroxide as the oxidation reagent. The procedure used was a follows: To a 1 L, two-neck RBF equipped with a condenser and an additional funnel, PS (200 g), acetic acid (35.3 g), and AMBERLITE® IR-120H (28.5 g) were combined and mixed well. H$_2$O$_2$ (160 mL, 50%) was added dropwise via the addition funnel and the reaction temperature maintained at 60° C. for 5 hours. After this period, the reaction mixture was allowed to cool to room temperature, transferred to a 2 L separatory funnel, and the bottom layer discarded. Next, 800 mL of ethyl acetate was added to the separatory funnel and the resulting solution washed three times with saturated NaHCO$_3$ solution (250 mL), followed by a brine wash (300 mL), and a final wash with DI water (300 mL). The ethyl acetate layer was dried with MgSO$_4$ and then solvent removed using vacuum at 35° C. and 100 bar pressure. Yield: 94%. 1H NMR (400 MHz, CDCl$_3$, TMS): 4.0 (dt, 2H, —OCH$_2$CH$_2$CH$_3$), 2.76-3.22 (m, 3H, —CH(O)CH—), 2.20-2.40 (t, 2H, —C=OCH$_2$—), 1.16-1.95 (m, 25H, —C=OCH$_2$CH$_2$—; —CH$_2$CH$_2$CH$_2$—; —CH(O)CH$_2$CH$_2$—; —CH(O)CH$_2$CH(O)—; CH$_3$CH$_2$CH$_2$—), 0.96-0.87 (m, 6H, —CH$_2$CH$_3$; —OCH$_2$CH$_2$CH$_3$).

Synthesis of Acrylated EAS (AAS). An acrylated derivative of AS was produced by reacting EAS with AA. To a 1 L RBF equipped with a condenser and an addition funnel, 100 g of EAS, 3 g potassium acetate, and 0.65 g of hydroquinone were combined and the mixture heated to 100° C. Next, 25.7 g of AA was added dropwise via the addition funnel and the reaction carried out over a 7 hour period. After this period, the reaction mixture was allowed to cool to room temperature before transferring to a 2 L separating funnel and adding 500 mL of n-hexane. The solution was then washed three times with DI water (150 mL), twice with brine (200 mL), and finally with DI water. The hexane layer was dried with MgSO$_4$ and solvent removed by vacuum stripping at 30° C. and 1 mbar. 1H NMR (400 MHz, CDCl$_3$, TMS): δ (ppm) −6.3-6.5 (m, 1.5H, C=OCH=CH$_2$); 6.1-6.2 (dd, 1.5H, —C=OCH=CH$_2$), 5.85-5.97 (m, 2.5H, —OCH$_2$CH=CH$_2$; —C=OCH=CH$_2$); 5.15-5.45 (m, 2H, —OCH$_2$CH=CH$_2$), 4.85 (1.5H—CH$_2$CHOC=O—), 4.54-4.58 (dt, 1.5H, —OCH$_2$CH=CH—), 3.7-4.0 (1.5H, —CHOH), 3.4-3.6 (1.5H, —CHOH), 2.32 (t, 2H, —C=0CH$_2$—), 1.16-1.88 (m, 23H, —C=0CH$_2$CH$_2$—; —CH$_2$CH$_2$CH$_2$—; —CH(O)CH$_2$CH$_2$—; —CH(O)CH$_2$CH(O)—), 0.96-0.87 (m, 3H, —CHCH$_3$).

Synthesis of Methacrylated EAS (MAS). MAS was synthesized by reacting EAS with MA.

To a 100 mL RBF equipped with a condenser and additional funnel, 20.02 g of EAS, 0.716 g potassium acetate, and 0.184 g of hydroquinone were combined and the temperature of the reaction mixture heated to 100° C. Next, 6.24 g of MA was added dropwise via the addition funnel and the reaction carried out over a period of 24 hours. The product was used without further purification. Yield: 98%. 1H NMR (400 MHz, CDCl$_3$, TMS): δ (ppm) 6.1-6.2 (dd, 1.5H, —C=OCH=CH$_2$), 5.85-5.97 (m, 2H, —OCH$_2$CH=CH$_2$); 5.45-5.67 (dd, 1.5H, —C=OCH=CH$_2$), 5.15-5.45 (m, 2.5H, CH$_2$CH=CH=CH$_2$—; —OCH$_2$CH=CH$_2$), 4.85 (1.5H—CH$_2$CHOC=O—), 4.54-4.58 (dt, 1.5H, —OCH$_2$CH=CH—), 3.7-4.0 (1.5H, —CHOH), 3.4-3.6 (1.5H, —CHOH), 2.32 (t, 2H, —C=0CH$_2$—), 1.90 (4.5H, CH$_2$=C(CH$_3$)C=O—), 1.16-1.88 (m, 23H, —C=0CH$_2$CH$_2$—; —CH$_2$CH$_2$CH$_2$—; —CH(O)CH$_2$CH$_2$—; —CH(O)CH$_2$CH(O)—), 0.96-0.87 (m, 3H, —CHCH$_3$).

Synthesis of Highly Functionalized Methacrylated EAS (HF-MAS). HF-MAS was synthesized by reacting EAS with methacrylic anhydride. To a 100 mL RBF, 10.08 g of EAS, 4.8 g of methacrylic anhydride, 0.15 g of ATC 3 catalyst (AMPAC™ Fine Chemicals), and 0.46 g of 2,6-di-t-butyl-4-methylphenol were combined. The reaction mixture was stirred at 100 OC for 48 hr. The product was used without further purification. Yield: 98%. 1H NMR (400 MHz, CDCl$_3$, TMS): δ (ppm) 6.1-6.2 (dd, 3H, —C=OCH=CH$_2$), 5.85-5.97 (m, 2H, —OCH$_2$CH=CH$_2$); 5.45-5.67 (dd, 3H, —C=OCH=CH$_2$), 5.15-5.45 (m, 2.5H, CH$_2$CH=CH—CH$_2$—; —OCH$_2$CH=CH$_2$), 4.85 (1.5H—CH$_2$CHOC=O—), 4.54-4.58 (dt, 3H, —OCH$_2$CH=CH—), 2.32 (t, 2H, —C=0CH$_2$—), 1.90 (9H, CH$_2$—=C(CH)C=O—), 1.16-1.88 (m, 23H, —C=0CH$_2$CH$_2$—; —CH$_2$CH$_2$CH$_2$—; —CH(O)CH$_2$CH$_2$—; —CH(O)CH$_2$CH(O)—), 0.96-0.87 (m, 3H, —CHCH$_3$).

Synthesis of Acrylated E3HS (A3HS). An acrylated derivative of 3HS was produced by reacting E3HS with AA. To a 1 L RBF equipped with a condenser and an addition funnel, 45.27 g of EPS, 1.36 g potassium acetate, 0.44 g of hydroquinone, and 200 ml of toluene were combined and the mixture heated to 90° C. Next, 17.16 g of AA was added dropwise via the addition funnel and the reaction carried out over a 24 hour period. After this period, the reaction mixture was allowed to cool to room temperature before transferring to a 2 L separating funnel and adding 500 mL of CH$_2$Cl$_2$. The solution was then washed three times with DI water (150 mL), twice with brine (200 mL), and finally with DI water (150 mL). The CH$_2$Cl$_2$ layer was dried with MgSO$_4$ and solvent removed by vacuum stripping at 30° C. and 1 mbar. Yield: 94%. 1H NMR (400 MHz, CDCl$_3$, TMS): δ (ppm) 6.3-6.5 (m, 2.5H, C=OCH=CH$_2$); 6.1-6.2 (dd, 2.5H, —C=OCH=CH$_2$), 5.85-5.97 (m, 2.5 H, —C=OCH=CH$_2$); 4.85-4.95 (m, 2.5H, —C=OOCH—), 4.104.25 (m, 2H, —OCH$_2$CH$_2$—), 3.65-3.90 (2.5H, —CHOH), 3.4-3.6 (2.5H, —CHOH), 2.15-2.35 (t, 2H, —C=OCH$_2$—), 1.90-2.0 (m, 2H, —O—CH$_2$CH$_2$), 1.16-1.88 (m, 30H, —C=OCH$_2$CH$_2$—; —CH$_2$CH$_2$CH$_2$—; —CH$_2$CH$_2$—), 0.96-0.87 (m, 6H, —CH$_2$CH$_3$).

Synthesis of Acrylated EPS (APS). An acrylated derivative of PS was produced by reacting EPS with AA. To a 1 L RBF equipped with a condenser and an additional funnel, 100 g of EPS, 3 g potassium acetate, and 0.65 g of hydroquinone were combined and the mixture heated to 100° C. Once the temperature of the reaction mixture reached 100° C., 25.7 g of AA was added dropwise via the addition funnel. The reaction was carried out over a 7 hour period. Once at room temperature, the reaction mixture was transferred to a 2 L separating funnel and 500 mL of n-hexane added. The reaction mixture was washed three times with DI water (150 mL), twice with brine (200 mL), and a finally with DI water (150 mL). The hexane layer was dried with MgSO$_4$ and solvent removed by vacuum stripping at 30° C. and 1 mbar. Yield: 97%. 1H NMR (400 MHz, CDCl$_3$, TMS): δ (ppm) 6.3-6.5 (m, 1.5H, C=OCH=CH$_2$); 6.1-6.2 (dd, 1.5H, —C=OCH=CH$_2$), 5.85-5.97 (m, 1.5 H, —C=OCH=CH$_2$); 4.85-4.95 (m, 1.5H, —C=OOCH—), 3.90-4.10 (dt, 2H, —OCH$_2$CH$_2$CH$_3$), 3.65-3.90 (1.5H, —CHOH), 3.4-3.6 (1.5H, —CHOH), 2.10-2.32 (t, 2H, —C=0CH$_2$—), 1.16-1.88 (m, 25H, —C=0CH$_2$CH$_2$—; —CH$_2$CH$_2$CH$_2$—; —CH$_2$CH$_2$—), 0.96-0.87 (m, 6H, —CH$_2$CH$_3$; —OCH$_2$CH$_2$CH$_3$).

Synthesis of Poly[(2-vinyloxy)ethyl soyate][Poly(2-VOES)]. Poly(2-VOES) was synthesized from 2-(vinyloxy) ethyl soyate using cationic polymerization as described by Alam and Chisholm (Alam et al., 2011 *J. Coat. Technol. Res.*, 8 671-683).

Synthesis of Epoxidized Poly(2-VOES). Epoxidized poly (2-VOES) was synthesized from poly(2-VOES) as described by Alam and Chisholm (Alam et al., 2011 *J. Coat. Technol. Res.*, 8 671-683).

Synthesis of Acrylated Poly(2-VOES) A-Poly(2-VOES). A-poly(2-VOES) was synthesized from epoxidized poly(2-VOES) as described by Alam and Chisholm (Alam et al., 2011 *J. Coat. Technol. Res.*, 8 671-683).

Coating Compositions and Preparation. Three sets of coatings were prepared for the study. One set of coatings were simply blends of each acrylated or methacrylated SBO-based material used for the study with 5 weight percent of the PI (i.e. IRGACURE® 2022). The other two sets of coatings utilized either ASBO or A-poly(2-VOES) as the reactive oligomer. Table 9 describes the compositions based on ASBO, while Table 10 describes the compositions based on A-poly(2-VOES). The liquid coatings were mixed using a FlackTek mixer operating at 3500 rpm for 5 minutes. Each coating solution was coated on nine steel-Q panels, one glass panel, and one TEFLON®-laminated glass panel using a drawdown bar with a 0.008 inch clearance. The coated panels were passed under a F300 UVA lamp (Fusion UV systems) using a conveyor belt speed of 5 feet/min. The UVA light intensity was found to be 1410 mW/cm$^2$ as measured using a UV POWER PUCK® II (ETC Inc.).

TABLE 9

Composition of coatings based on ASBO as the reactive oligomeric component and APS, AAS, A3HS, MAS, or HF-MAS as the reactive diluent. All values are in weight percent.

| Coating Designation | APS | AAS | A3HS | MAS | HF-MAS | ASBO | PI |
|---|---|---|---|---|---|---|---|
| APS/ASBO 25/75 | 23.7 | — | — | — | — | 71.3 | 5 |
| AAS/ASBO 25/75 | — | 23.7 | — | — | — | 71.3 | 5 |
| A3HS/ASBO 25/75 | — | — | 23.7 | — | — | 71.3 | 5 |
| MAS/ASBO 25/75 | — | — | — | 23.7 | — | 71.3 | 5 |
| HF-MAS/ASBO 25/75 | — | — | — | — | 23.7 | 71.3 | 5 |
| APS/ASBO 50/50 | 47.5 | — | — | — | — | 47.5 | 5 |
| AAS/ASBO 50/50 | — | 47.5 | — | — | — | 47.5 | 5 |
| A3HS/ASBO 50/50 | — | — | 47.5 | — | — | 47.5 | 5 |
| MAS/ASBO 50/50 | — | — | — | 47.5 | — | 47.5 | 5 |
| HF-MAS/ASBO 50/50 | — | — | — | — | 47.5 | 47.5 | 5 |

TABLE 10

Composition of coatings based on A-poly(2-VOES) as the reactive oligomeric component and APS, AAS, and A3HS as the reactive diluent. All values are in weight percent.

| Coating Designation | APS | AAS | A3HS | A-Poly(2-VOES) | PI |
|---|---|---|---|---|---|
| APS/A-poly(2-VOES) 25/75 | 23.7 | — | — | 71.3 | 5 |
| AAS/A-poly(2-VOES) 25/75 | — | 23.7 | — | 71.3 | 5 |
| A3HS/A-poly(2-VOES) 25/75 | — | — | 23.7 | 71.3 | 5 |
| APS/A-poly(2-VOES) 50/50 | 47.5 | — | — | 47.5 | 5 |

TABLE 10-continued

Composition of coatings based on A-poly(2-VOES) as the reactive oligomeric component and APS, AAS, and A3HS as the reactive diluent. All values are in weight percent.

| Coating Designation | APS | AAS | A3HS | A-Poly(2-VOES) | PI |
|---|---|---|---|---|---|
| AAS/A-poly(2-VOES) 50/50 | — | 47.5 | — | 47.5 | 5 |
| A3HS/A-poly(2-VOES) 50/50 | — | — | 47.5 | 47.5 | 5 |

Coating Characterization Methods and Instrumentation. A JEOL-ECA 400 (400 MHz) nuclear magnetic resonance (NMR) spectrometer equipped with an autosampler was used to generate $^1$H NMR spectra. Data acquisition was completed using 16 scans in CDCl$_3$ as the solvent. Infrared spectra were obtained with a Nicolet 6700 FTIR spectrometer. Samples were prepared by coating a thin layer of liquid on a KBR plate. Spectra were recorded using 64 scans and 4 cm$^{-1}$ resolution with a data spacing of 0.964 cm$^{-1}$. The thickness of the cured coatings was determined using a PosiTest DFT® dry-thickness measurement gauge from DeFlesko Corporation. Chemical resistance was accessed using ASTM D 5402-93, which is typically referred to as the MEK (methyl ethyl ketone) double rub test. The hardness of the coatings was accessed using the König pendulum hardness test (ASTM D 4366-95), while the impact resistance of coated panels was accessed using ASTM D 2794-93. Viscoelastic properties of cured free films were obtained using dynamic mechanical analysis (Q800 from TA Instruments). The free film specimens were obtained from the coatings cast over the Teflon coated glass panels. The measurements were carried out using the following parameters: temperature range −40° C. to 120° C., heating rate of 5° C./min., frequency 1 Hz, and strain amplitude of 0.02%. The glass transition temperature ($T_g$) was obtained from the peak maximum in the tan δ response. Mechanical properties were obtained from "dumb bell"-shaped free film specimens using an Instron 5545 Tensile Tester fitted with a 100 N load cell and the procedure outlined in ASTM D 638-5. The displacement rate of the movable clamp was set as 1 mm/minute. The data reported was the average of 5 replicate measurements. Rheological properties were determined with an ARES Rheometer from TA Instruments. Liquid samples were placed in between a cone and plate and viscosity recorded at a temperature of 25° C. and shear rate of 10 s$^{-1}$.

Results and Discussion

Acrylate/Methacrylate Synthesis. The chemical structures of the five SBO-based acrylate or methacrylate compounds investigated for potential application as reactive diluents are shown below:

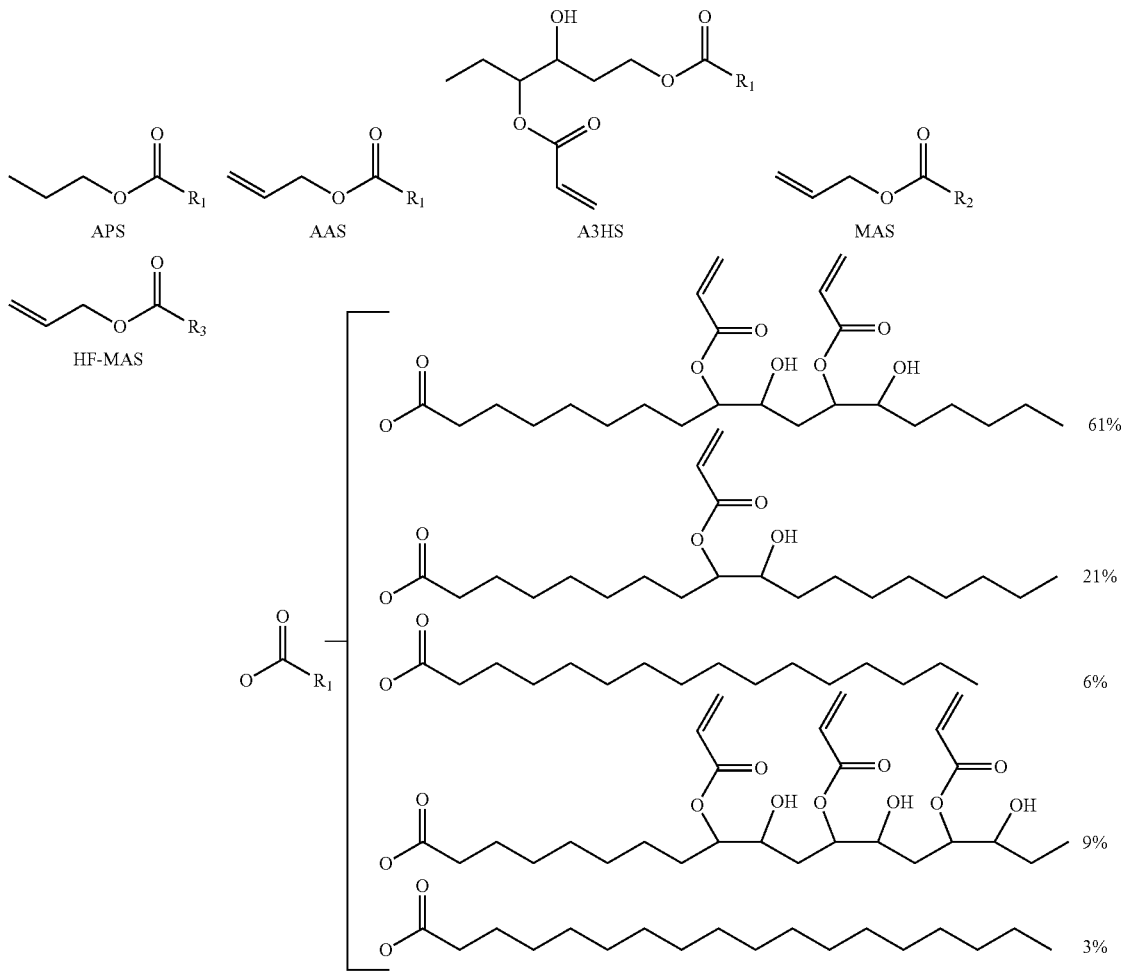

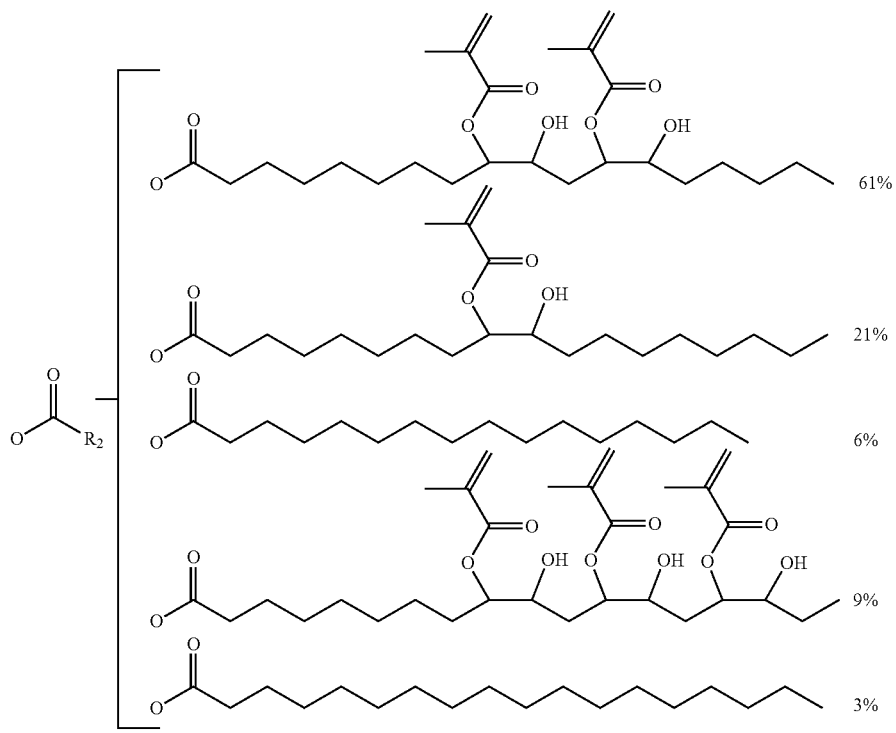
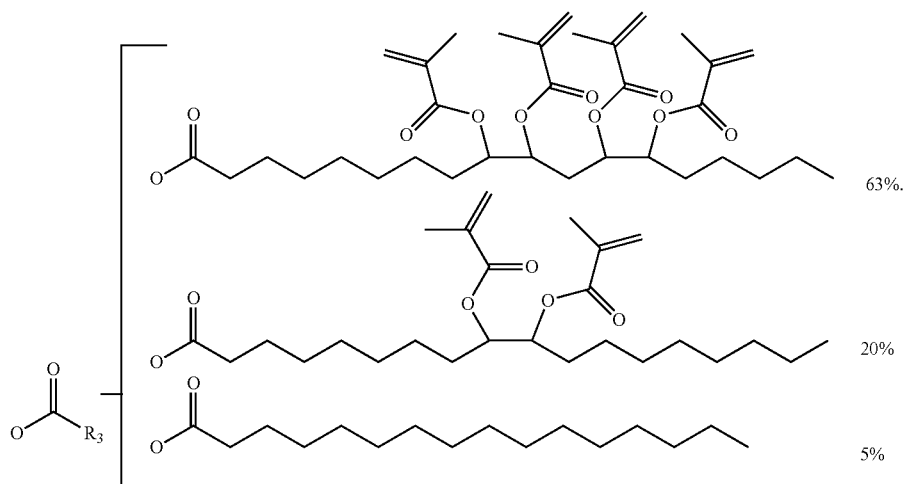
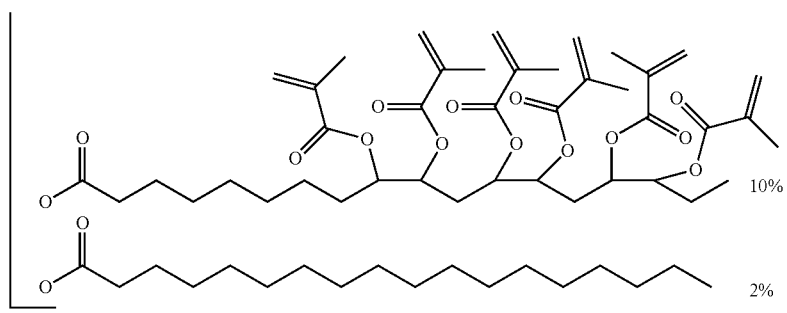

The generic synthetic method used to produce APS, AAS, and A3HS is shown below:
1) Transesterification
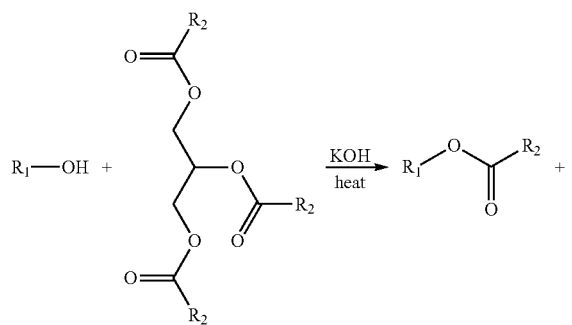
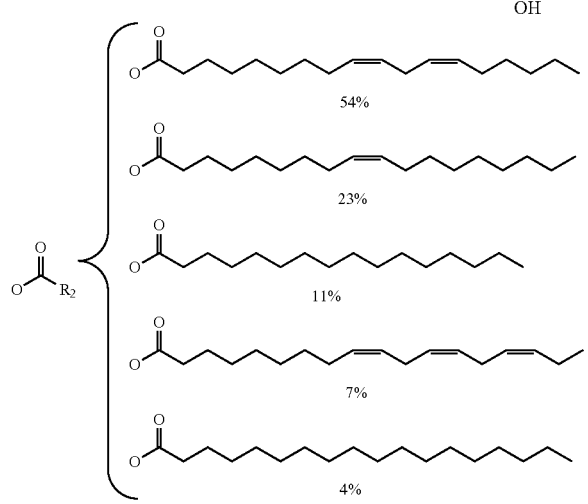
2) Epoxidation
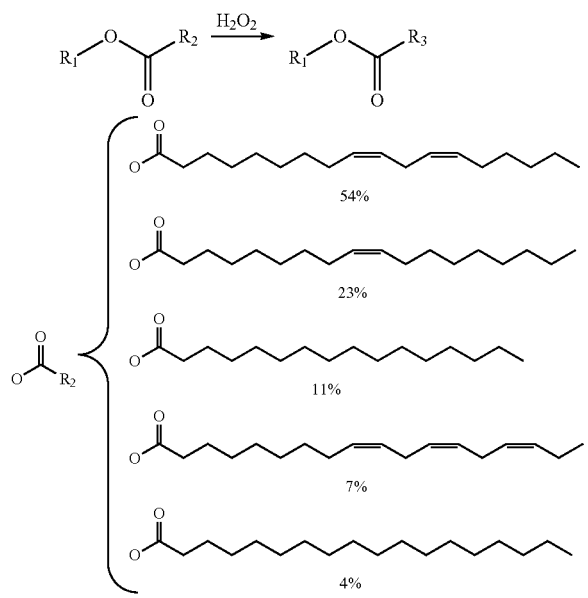
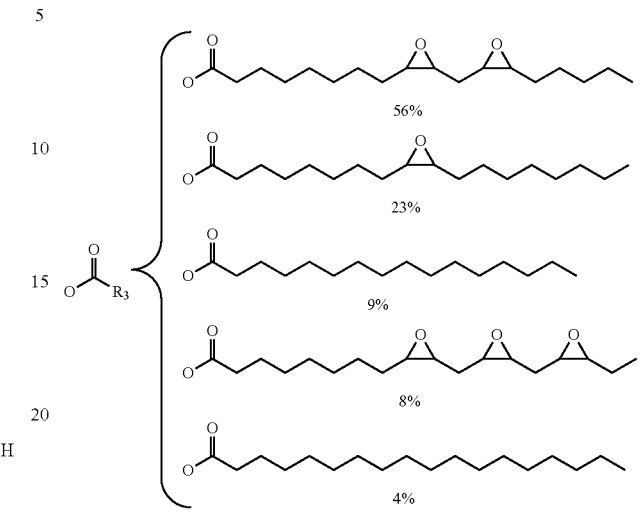
3) Acrylation
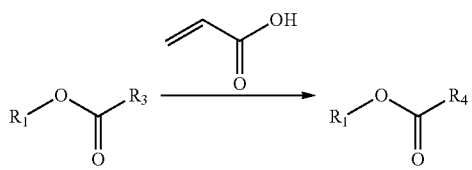
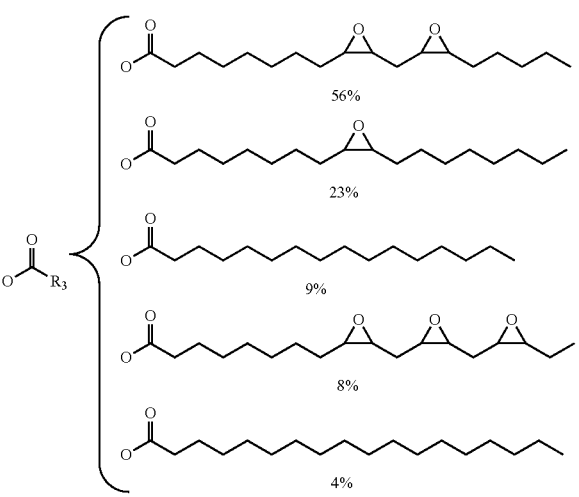

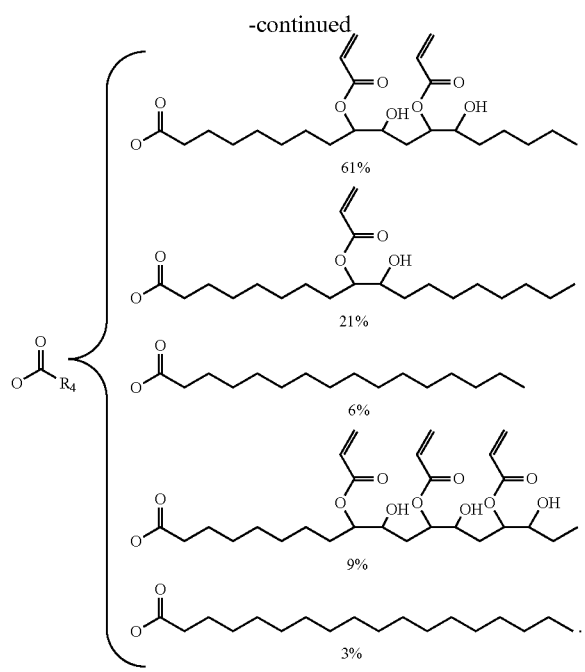

First, a base-catalyzed transesterification was conducted using a mono-functional alcohol and SBO to produce a monoester compound with a significantly lower molecular weight and viscosity than SBO. Next, an oxidation reaction was conducted using hydrogen peroxide to convert disubstituted double bonds to epoxy groups. Finally, the acrylate functionality was introduced by ring-opening the epoxy groups with AA. For MAS, MA was used in place of AA. For HF-MAS, methacrylic anhydride was used to generate methacrylate groups both by epoxy ring-opening reactions as well as esterification reactions involving the secondary hydroxyl groups derived from the epoxy ring-opening reactions. Successful synthesis of each of the five SBO-based acrylate or methacrylate compounds shown above as well as their intermediates was confirmed using $^1$H NMR.

Figure 1B:
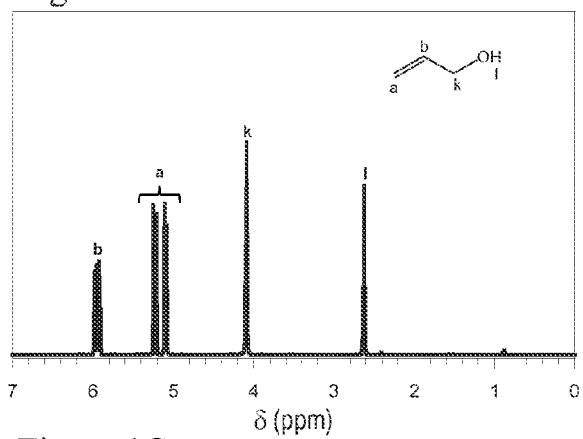
FIG. 1B shows $^1$H NMR spectra obtained for acrylic acid (AA).
Figure 1C:
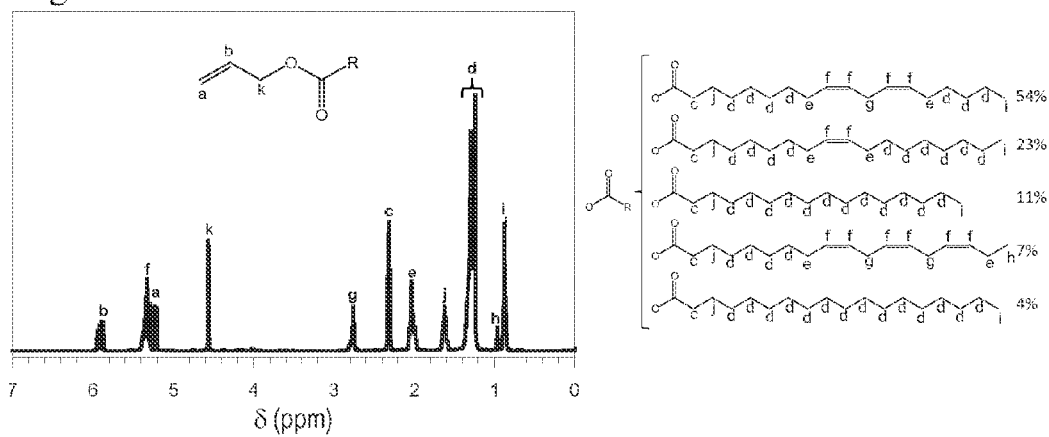
FIG. 1C shows $^1$H NMR spectra obtained for soybean oil allyl soyate (AS).

To illustrate, FIGS. 1 and 2 provide $^1$H NMR spectra with peak assignments that demonstrate the successful synthesis of AAS as well as the two intermediates, AS and EAS. FIG. 1 displays $^1$H NMR spectra obtained for AS (FIG. 1C) and, for reference purposes, the $^1$H NMR spectra for the starting materials, SBO (FIG. 1A) and AA (FIG. 1B). A comparison of the $^1$H NMR spectrum for SBO to that obtained for AS clearly shows that all of the protons present in the fatty acid portion of SBO (R in FIG. 1A) are present in AS, but the proton signals associated with the glycerol component of SBO are absent. A comparison of the $^1$H NMR spectrum for AS to the spectrum for AA shows that AS possesses the vinyl group derived from AA. Also, the signal associated with the methylene protons a to the vinyl group in AA ($\delta$=4.10 ppm) is shifted down-field by 0.48 ppm in the spectrum for AS ($\delta$=4.58). This down-field shift is consistent with expectations since conversion of the alcohol to an ester has a deshielding effect on the methylene protons a to the oxygen atom. Further, the signal for the hydroxyl proton present in the spectrum for AA is not present in the spectrum for AS, indicating successful esterification.

Figure 2A:
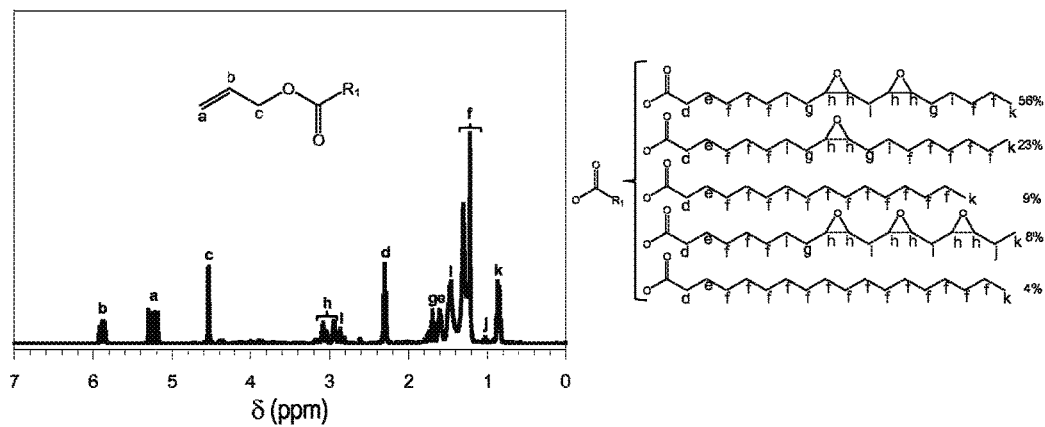
FIG. 2A shows $^1$H NMR spectra obtained for epoxidized AS (EAS).
Figure 2B:
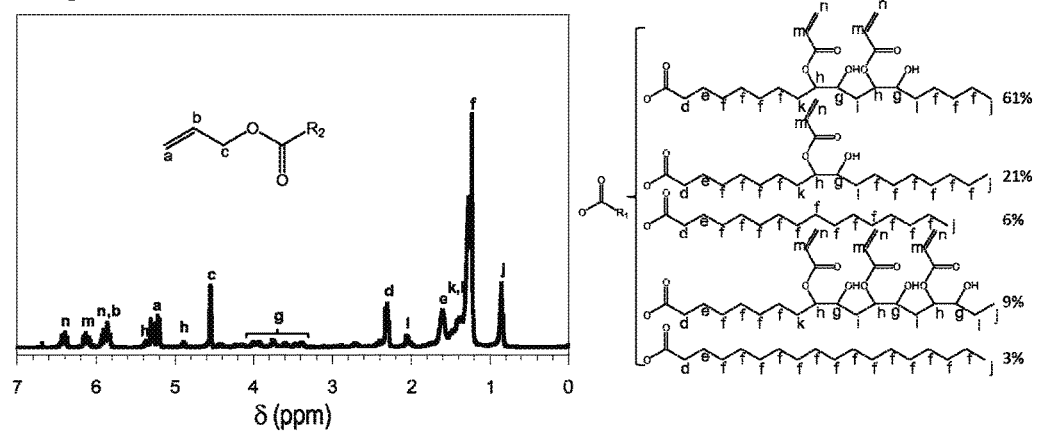
FIG. 2B shows $^1$H NMR spectra obtained for acrylated AS (AAS).

FIG. 2A displays the $^1$H NMR spectrum for EAS. A comparison of the $^1$H NMR spectrum for EAS to that of AS (FIG. 1C) shows that the double bonds present in the fatty acid ester portion of AS were epoxidized while the terminal double bond derived from AA was not. Considering the spectrum for EAS (FIG. 2A), this conclusion was based on the lack of the multiplet at 5.35 ppm, which corresponds to the fatty acid ester vinyl protons ("f" in FIG. 1C), the presence of the signals associated with the vinyl protons from the terminal double bonds derived from AA at 5.84-5.93 ppm ("b" in FIG. 2A) and 5.18-5.3 ppm ("a" in FIG. 2A), and the presence of new signals at 2.90-3.10 ppm ("h" in FIG. 2A) that correspond to the protons of the epoxide groups. The fact that the internal (i.e. disubstituted) doubles were completely epoxidized while the terminal (i.e. monosubstituted) doubles were not epoxidized can be explained by considering inductive effects associated with double bond substitution and the reactivity of the epoxidization reagent (Lane et al., 2003 Chem. Rev., 103, 2457-2473). With regard to inductive effects, alkyl substituents have an electron donating inductive effect. Thus, disubstitution increases electron density at the double more than monosubstitution resulting in higher reactivity of the former towards epoxidation. Also, compared to stronger oxidizing agents such as meta-chloroperoxybenzoic acid, hydrogen peroxide is a less reactive epoxidation reagent and, as a result, selectively epoxidized just the internal double bonds. This result was deemed potentially beneficial since the allyl group was expected to be reactive during photo-curing and minimizing the number of hydroxyl groups produced upon subsequent reaction with acrylic or methacrylic acid should minimize viscosity.

A comparison of the $^1$H NMR spectrum for AAS (FIG. 2B) to that of EAS (FIG. 2A) confirmed successful epoxy ring-opening using acrylic acid as the ring-opening reagent. As shown in the $^1$H NMR spectrum for AAS, signals resulting from the protons associated epoxide groups ("h" in FIG. 2A) are absent, while new signals associated with protons of the acrylate double bonds are observed ("m and n" in FIG. 2B). Since nucleophilic attack by the carboxylate anion of acrylic acid can occur at either of the two carbon atoms of the epoxy group and the fatty acid ester groups derived from linoleic and linolenic acid have multiple epoxy groups in close proximity to each other, a number of proton signals associated with the methine groups generated upon epoxy ring-opening were produced. Using HETCOR 2D NMR and estimates of chemical shifts using ChemDraw® Ultra, these methine protons were assigned generically as being associated with a hydroxy-substituted carbon atom ("g" in FIG. 2B) or acrylate-substituted carbon atom ("h" in FIG. 2B).

Figure 3:
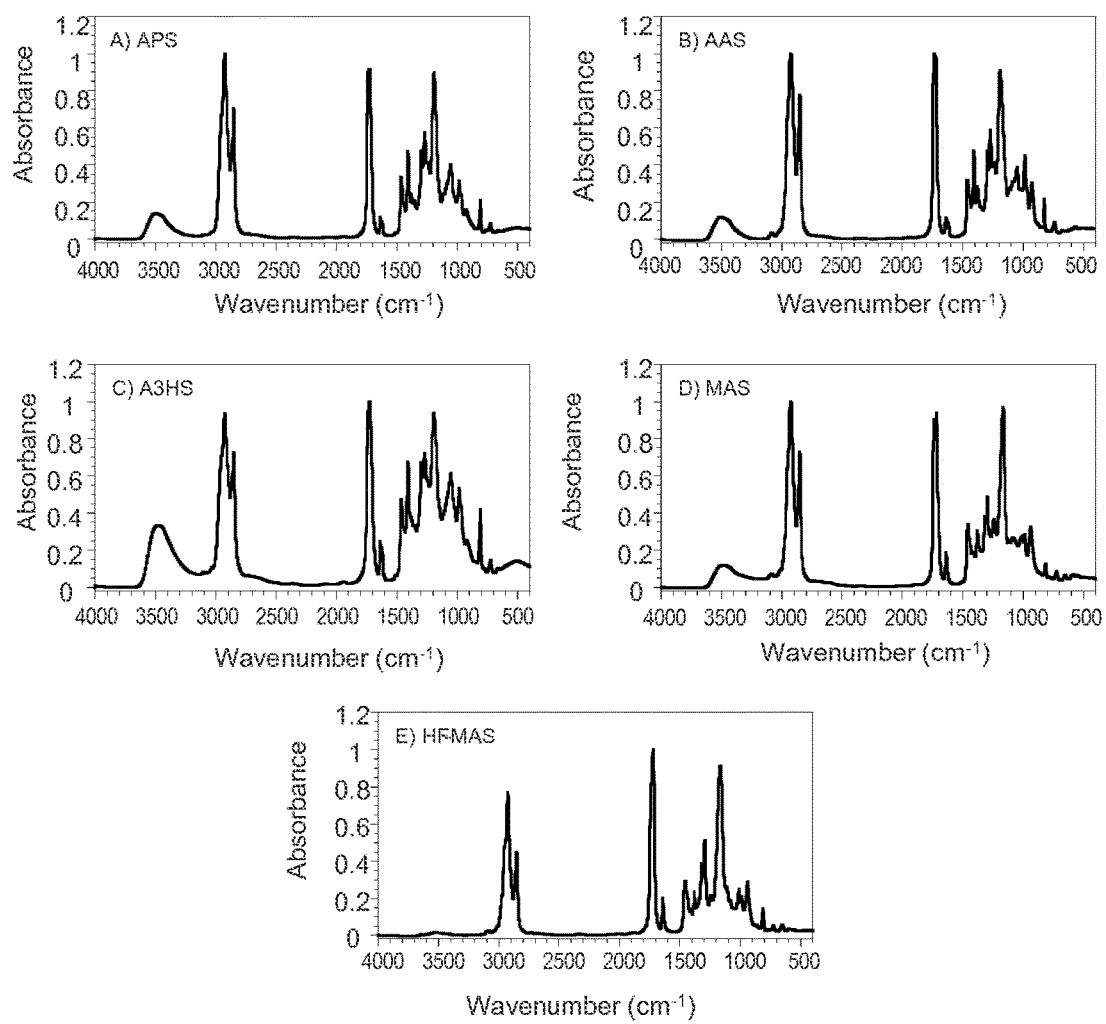
FIG. 3 shows FTIR spectra obtained for each of five SBO-based reactive diluents.

In addition to chemical characterization by $^1$H NMR, FTIR was also utilized. The FTIR spectra obtained for each of the five SBO-based reactive diluents are shown in FIG. 3. The spectra exhibit the absorption bands expected based on the anticipated chemical structure. For example, the intense band at 1730 cm$^{-1}$ is due to the presence of the carbonyl groups (i.e. C=O stretching), while the weak band at 1630 cm$^{-1}$ is a result of the double bonds (i.e. C=C stretching). The broad band in the region of 3500 cm$^{-1}$ readily observed in the spectra for all of the SBO-based reactive diluents except HF-MAS is the result of the hydroxy groups generated upon ring-opening of epoxy groups by the carboxylate groups from acrylic or methacrylic acid. For HF-MAS, the band at 3500 cm$^{-1}$ is very weak indicating that the hydroxyl groups created by epoxy-ring opening reactions were effectively esterified using the excess of methacrylic anhydride. The strong bands in the region between 2780-3050 cm$^{-1}$ in all five spectra are due to vibrations related to C—H bonds associated with the methyl, methylene, methine, and alkene groups.

In addition to ASBO, A-poly(2-VOES) was used as an acrylated oligomer in the study. To produce A-poly(2-VOES), SBO was first reacted with 2-(vinyloxy)ethanol using base-catalyzed transesterification to produce the vinyl ether monomer, 2-(vinyloxy)ethyl soyate (2-VOES), as shown below in part A. From 2-VOES, poly(2-VOES) was produced by cationic polymerization, as shown below in part B.

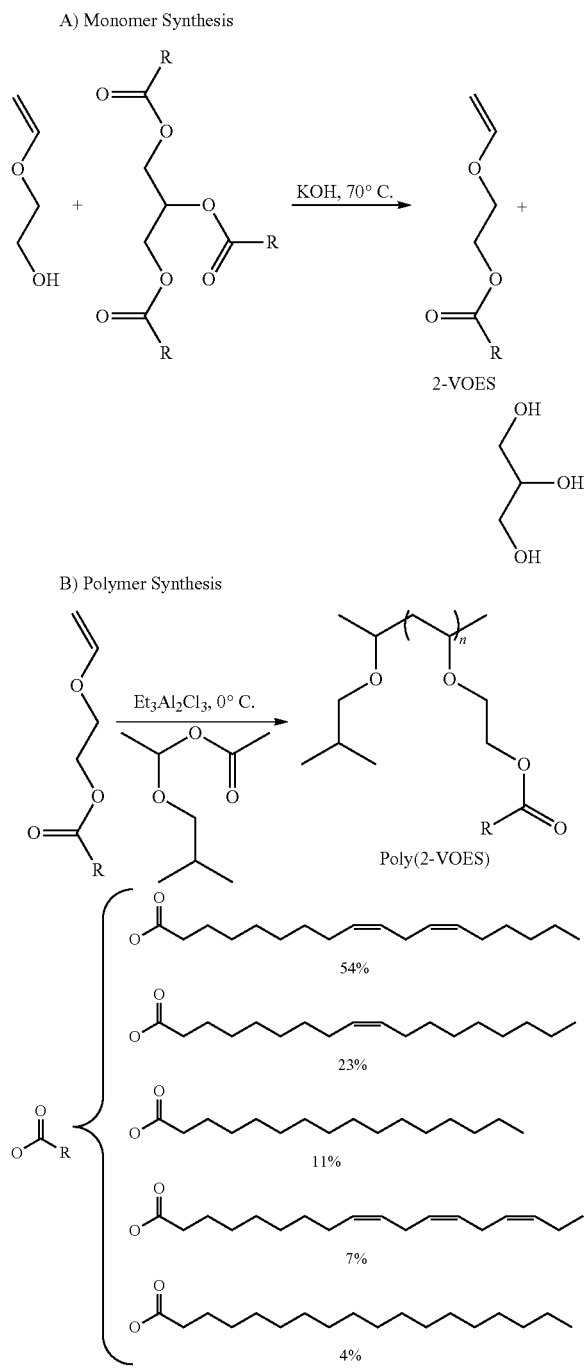

With the cationic polymerization system utilized, polymerization occurred exclusively through the vinyl ether groups, which allowed the double bonds derived from SBO fatty acid ester groups to be retained. These double bonds were converted to acrylate groups by conducting post-polymerization derivatization reactions as described by Alam and Chisholm (Alam et al., 2011 *J. Coat. Technol. Res.*, 8 671-683).

Properties of the Coating Precursors. For UV-curable coatings, the viscosity and acrylate/methacrylate equivalent weight (EW) of the precursors are very important parameters. For the reactive diluent, the viscosity must be relatively low to enable adequate processability without the use of solvent. The acrylate/methacrylate EW of the reactive diluent has a major impact on the crosslink density of the coating, which affects most all of the coating physical properties including hardness, chemical resistance, impact resistance, and abrasion and scratch resistance. Acrylate/methacrylate EW can also affect adhesion since it affects the extent of shrinkage upon cure. The viscosity of the acrylates used for the study was determined at 25° C. using a shear rate of 10 s$^{-1}$. As shown in Table 11, all five of the SBO-based reactive diluents possess much lower viscosity than ASBO. In fact, the viscosities of APS, AAS, MAS, and HF-MAS are all around 50 cP or less, which is more than two orders of magnitude lower than the viscosity for ASBO. The viscosities obtained for APS, AAS, MAS, and HF-MAS are comparable to viscosities of commercially available petrochemical-based reactive diluents such as ethoxylated trimethylolpropane triacrylate (SR-454 from Sartomer, viscosity at 25° C.=60 cP), alkoxylated hexanediol diacrylate (CD-560 from Sartomer, viscosity at 25° C.=24 cP), triethylene glycol diacrylate (SR-272 from Sartomer, viscosity at 25° C.=30 cP), and trimethylol propane triacrylate (SR-351 from Sartomer, viscosity at 25° C.=105 cP) (Sartomer product technical data sheets).

In calculating the EW of the five SBO-based reactive diluents, the allyl functionality present in AAS, MAS, and HF-MAS was included as a reactive group in addition to the acrylate or methacrylate groups. It was hypothesized that the allyl groups would participate in free radical polymerization/crosslinking reactions either by direct addition of a free radical species across the double bond or by chain transfer reactions involving the allylic hydrogen atoms or by a combination of the two reactions. Comparing the EW data shown in Table 11 for the five different SBO-based reactive diluents, it can be seen that EW is significantly reduced by using a vinyl-functional alcohol for the transesterification reaction. For example, the EW for AAS is 40% lower than that of APS, while the EW of HF-MAS is about 24% lower than APS. The significantly lower EW enabled by the use of a vinyl-functional alcohol was expected to provide higher crosslink densities, which translates to better chemical and abrasion resistance, higher hardness, and improved barrier properties. In addition to lowering the EW, the use of a vinyl-functional alcohol for the transesterification also ensures that every molecule has at least one reactive functional group. This feature minimizes the potential for unreacted material remaining in the cured coating. As illustrated above, about 15 weight percent of the fatty acid groups in SBO are saturated. Thus, the use of an alcohol for the transesterification reaction that does not provide a functional group capable of participating in free radical polymerization/crosslinking reactions, which is the case for APS, results in a cured coating that can possess a significant amount of "free/unreacted" material that can potentially plasticize the crosslinked network and, thus, reduce hardness, chemical and abrasion resistance, glass transition temperature (Tg), etc. Further, unreacted material can potentially bloom to the coating surface over time leading to an oily surface and changes in coating properties.

With regard to renewable content of the coating precursors, both the overall renewable content and weight percent of the compound derived from SBO (i.e. SBO content) were calculated. For the calculation of renewable content, AA, nP, 3H, and ALA were all considered to be derived from renewable resources. AA can be obtained from biomass by converting carbohydrates to lactic acid and then dehydrating lactic acid to AA (Xu et al., 2006 Chin. J. Chem. Eng., 14, 419-427). nP has been produced from lignocellulosic biomass using an actinobacterium, Thermobifida fusca (Deng et al., 2011 Metabolic Eng., 13, 570-577). ALA can be obtained from glycerol through a dehydration process (Hoelderich et al., DE 102008031828 A1). 3H, also referred to as leaf alcohol, is produced in small amounts by most plants (Ohta, 1984 Geochem. J., 18, 135-141). From Table 11, it can be seen that all of the coating precursors possess a relatively high renewable content. HF-MAS has the lowest renewable content due to the relatively high number of methacrylate groups present in the structure.

only difference in chemical composition between APS and AAS is that the n-propyl ester group in APS is replaced with an allyl ester group in AAS. As indicated by the data in Table 12, the allyl ester group provided tack-free coatings with increased hardness and chemical resistance as compared to the n-propyl ester-based analog (i.e. APS). This result provides evidence that the allylic group participates in free radical polymerization/crosslinking.

The only difference in chemical composition between MAS and AAS is that MAS possesses methacrylate groups in place of the acrylate groups present in AAS. Both materials possess the ally ester group. The higher Tg obtained for MAS as compared to AAS is consistent with expectations considering the restrictions to molecular mobility the methyl group places on the polymer backbone. However, the lower modulus, lower chemical resistance, lower storage modulus above Tg, and higher elongation at break observed for MAS as compared to AAS suggests that the extent of cure, and thus the crosslink density, was lower

TABLE 11

Viscosity, molecular weight (MW), functional group concentration per molecule, theoretical EW, renewable content, and SBO content for the coating precursors used for the study.

| Acrylate | Viscosity (cP) | Theoretical MW (g/mole) | Functional Groups/molecule | Theoretical EW (g/mole) | Renewable Content (wt. %) | SBO Content (wt. %) |
|---|---|---|---|---|---|---|
| APS | 53 | 471 | 1.5 | 314 | 94 | 58 |
| AAS | 40 | 469 | 2.5 | 188 | 94 | 58 |
| A3HS | 351 | 599 | 2.5 | 240 | 93 | 45 |
| MAS | 34 | 492 | 2.5 | 197 | 77 | 55 |
| HF-MAS | 49 | 618 | 4.0 | 155 | 54 | 44 |
| ASBO | 10,600 | 1324 | 4.5 | 294 | 94† | 69 |
| A-Poly(2-VOES) | 41,700 | NA* | NA* | 327 | 76 | 55 |

*Exact polymer molecular weight could not be measured; however, the molecular weight of the poly(2-VOES) sample used to produce A-poly(2-VOES) possessed a number-average molecular weight of 15,400 g/mole expressed relative to polystyrene standards.

Prior to preparing coatings based on the five SBO-based reactive diluents and the two oligomeric acrylates [i.e. ASBO and A-poly(2-VOES)], it was of interest to characterize the properties of the cured precursors. Thus, each of the five SBO-based reactive diluents and the two SBO oligomeric acrylates were individually blended with 5 weight percent of the PI and the mixtures coated onto panels and subsequently UV-cured. The coatings derived from APS were tacky and, as a result, free films for conducting tensile testing and DMA were not able to be generated. In contrast, coatings derived from HF-MAS were very brittle and exhibited micro-cracking upon cure, which prevented coating property data from begin obtained. Table 12 provides the data obtained from the coatings produced.

With regard to the coatings derived from the five SBO-based reactive diluents, a comparison of the properties obtained for APC to AAS clearly indicate that the allyl group present in AAS contributes to the production of the cross-linked network upon UV exposure. As illustrated above, the for MAS. A lower extent of crosslinking upon UV exposure for MAS is very likely since methacrylate-based free radicals are significantly less reactive that acrylate-based free radicals due to the added stabilization provided by the methyl group through hyperconjugation (O'Hara, "Resins and Monomers for Today's Radiation Curable Coatings," in Radiation Curing of Polymers, Randel (Ed.), The Royal Society of Chemistry, London, 1987, pg. 116-127).

Compared to AAS, A3HS provided a coating with lower Tg, hardness, chemical resistance, and modulus, which is consistent with the lower EW of this SBO-based acrylate. With regard to the two SBO-based oligomeric acrylates, the Young's modulus, hardness, and storage modulus above Tg were higher for A-poly(2-VOES), which was expected based on the much higher number of acrylate groups per molecule for A-poly(2-VOES) as compared to ASBO (Alam et al., 2011 J. Coat. Technol. Res., 8 671-683).

TABLE 12

Properties of coatings based on ASBO, A-poly(2-VOES), APS, AAS, or A3HS with 5 weight percent PI.

|  | ASBO | A-Poly(2-VOES) | APS | AAS | A3HS | MAS |
|---|---|---|---|---|---|---|
| Average Thickness (μm) | 98 + 6 | 78 ± 2 | 83 + 4 | 91 ± 4 | 89 ± 3 | 77 ± 3 |
| Young's Modulus (MPa) | 453 + 9 | 489 ± 25 | NA‡ | 33 ± 3 | 14 ± 1 | 8 ± 2 |
| Elongation (%) | 7 + 1 | 6 ± 1 | NA‡ | 12 ± 1 | 18 ± 1 | 29 ± 4 |

TABLE 12-continued

Properties of coatings based on ASBO, A-poly(2-VOES),
APS, AAS, or A3HS with 5 weight percent PI.

|  | ASBO | A-Poly(2-VOES) | APS | AAS | A3HS | MAS |
|---|---|---|---|---|---|---|
| Storage mod. at 90° C. (MPa) | 45 | 53 | NA‡ | 5 | 6 | 2 |
| Tg from tan δ (° C.) | 45 | 38 | NA‡ | 6 | −1 | 15 |
| Pendulum Hardness (sec) | 50 ± 1 | 69 ± 0 | 13 ± 0 | 23 ± 1 | 17 ± 0 | 10 ± 0 |
| MEK Double Rubs | >1500 | >2000 | 17 | 215 | 175 | 38 |

†Equivalent weight calculation included the allyl group.
‡Free film was too tacky to measure.

Coatings Based on ASBO as the Reactive Oligomeric Component.

Table 13 lists the properties obtained for UV-curable coatings based on ASBO as the reactive oligomer and APS, AAS, or A3HS as the SBO-based reactive diluent. Two ratios of reactive diluent to ASBO were utilized, namely, 25/75 and 50/50 by weight. A comparison of the data obtained for coatings based on APS as the reactive diluent to their counterparts based on AAS, it is clear that the allyl functionality in AAS participates in polymerizationcrosslinking during UV exposure. The coatings based on AAS possessed significantly higher chemical resistance (MEK double rubs), Tg, Young's modulus, hardness, and storage modulus above Tg as compared to those coatings based on APS. With regard to crosslink density, the rubbery plateau modulus (i.e. storage modulus at temperatures above Tg) can be used to directly compare differences in crosslink density between materials since, based on the theory of rubber elasticity (Flory, 1953. *Principles of Polymer Chemistry*. Ithaca, N.Y.: Cornell University Press; Murayama, 1978. *Dynamic Mechanical Analysis of Polymeric Materials*. Amsterdam: Elsevier), crosslink density is proportional to storage modulus in the rubbery plateau region, as follows:

$$v = E'/(3RT)$$

where v is the crosslink density defined as the moles of crosslinks per unit volume of material, R is the gas constant, E' is storage modulus in the rubbery plateau region, and T is the temperature corresponding to the storage modulus value (Hill, 1992 *J. Coat. Technol.*, 64, 29-41).

Figure 4A:
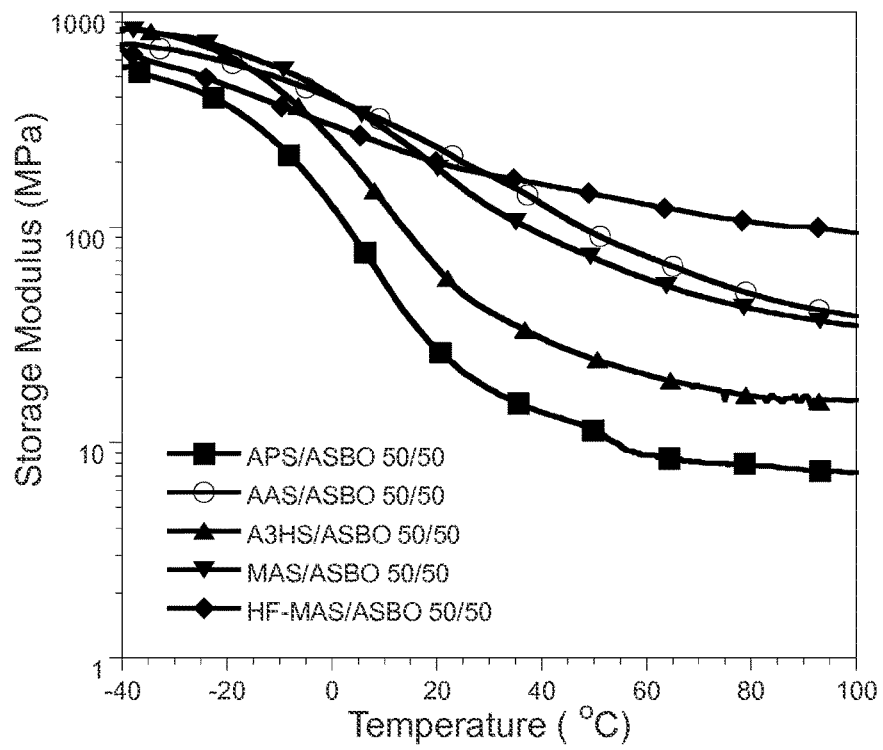
FIG. 4A shows storage modulus as a function of temperature for coatings containing 50 weight percent acrylate-functional soybean oil (ASBO).
Figure 4B:
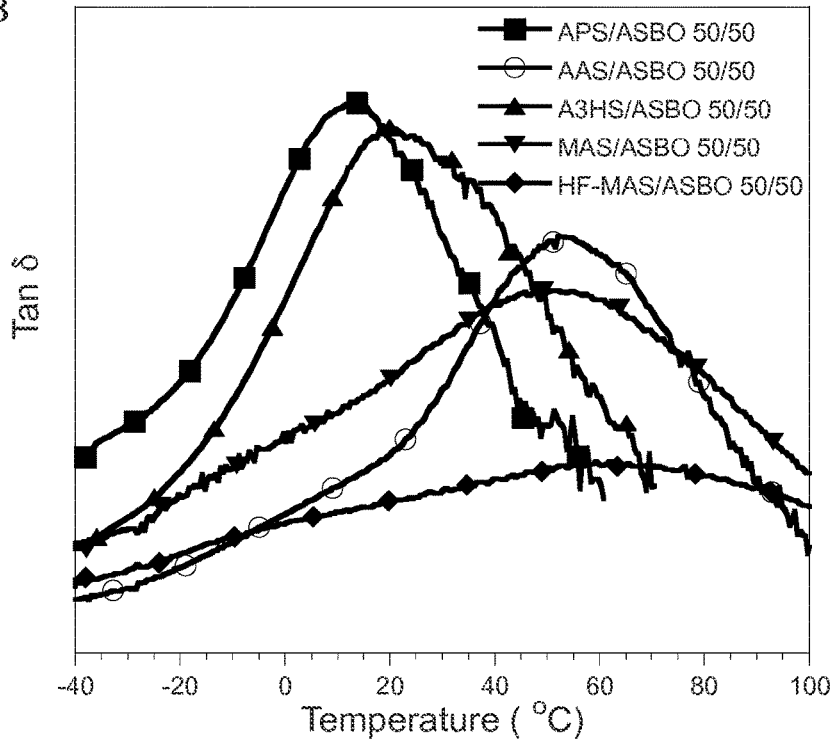
FIG. 4B shows tan δ data as a function of temperature for coatings containing 50 weight percent ASBO. The ratio of reactive oligomer to reactive diluent was 50/50.

FIG. 4 displays storage modulus (FIG. 4A) and tan delta data (FIG. 4B) as a function of temperature for all of the coatings containing 50 weight percent ASBO. Over the temperature range used for the measurements, all of the films exhibited a Tg that varied with the composition of the reactive diluent. The coating based on APS exhibited a much lower Tg and lower storage modulus in the rubbery plateau region as compared to the analogous coating based on AAS. Both the difference and Tg and the difference in rubbery plateau storage modulus can be explained by the obtainment of a significantly higher crosslink density with the use of AAS, which suggests that the allyl functional group in AAS contributes to polymerization/crosslinking during curing.

The physical property data obtained for the coatings based on A3HS indicate that the use of this SBO-based reactive diluent provides crosslink densities that are higher than analogous coatings based on APS, but lower than analogs based on AAS. This can be most easily seen from the DMA data shown in FIG. 4. For the A3HS/ASBO 50/50 coating, both Tg and E' in the rubbery plateau region were higher than those values for the APS/ASBO 50/50 coating but lower than the values obtained for AAS/ASBO 50/50. This result is consistent with expectations based on the differences in acrylate EW (Table 11) between the three SBO-based reactive diluents.

TABLE 13

Data obtained for UV cured coatings based on ASBO as the reactive oligomeric
component and APS, AAS, or A3HS as the reactive diluent.

|  | APS/ASBO 25/75 | AAS/ASBO 25/75 | A3HS/ASBO 25/75 | APS/ASBO 50/50 | AAS/ASBO 50/50 | A3HS/ASBO 50/50 |
|---|---|---|---|---|---|---|
| Viscosity (cP) | 1,970 | 1,944 | 4,412 | 548 | 477 | 1,655 |
| Thickness (μm) | 81 ± 3 | 80 ± 2 | 93 ± 5 | 78 ± 3 | 79 ± 2 | 80 ± 3 |
| Young's Mod. (MPa) | 82 ± 3 | 438 ± 10 | 155 ± 9 | 20 ± 1 | 199 ± 12 | 57 ± 3 |
| Elongation (%) | 15 ± 2 | 7 ± 2 | 13 ± 0.4 | 14 ± 1 | 10.5 ± 3 | 17 ± 2 |
| *E' @ 90° C. (MPa) | 19 | 51 | 17 | 8 | 43 | 16 |
| Tg (° C.) | 23 | 57 | 35 | 14 | 52 | 21 |
| Pend. Hardness (sec) | 25 ± 0 | 41 ± 0 | 35 ± 0 | 23 ± 0 | 32 ± 1 | 21 ± 0 |
| Rev. Impact (in-lb) | 28 | 44 | 32 | 16 | 40 | 56 |
| MEK Double Rubs | 389 | >2,000 | 932 | 157 | 1,350 | 553 |

*E' indicates storage modulus.

Table 14 displays data for films obtained using ASBO as the reactive oligomer component and MAS or HF-MAS as the reactive diluent. For comparison purposes, data for the analogous coating based on AAS as the reactive diluent was included in the table. The only difference in chemical structure between AAS and MAS is that MAS possesses methacrylate groups in place of the acrylate groups present in AAS. As shown in FIG. 4B, the temperature at the peak maximum of the tan delta response associated with the coating Tg for MAS/ASBO 50/50 was about 4° C. lower than that for AAS/ASBO 50/50, but the transition was much broader and extending to higher temperatures. This result indicates a much broader distribution of molecular weight between crosslinks for the MAS/ASBO 50/50 film. This broader distribution of molecular weight between crosslinks may be due to the fact that this coating possesses three different reactive groups that vary substantially with respect to reactivity during free radical photopolymerization. The three functional groups present in the MAS/ASBO 50/50 coating are the allyl group (derived from MAS), methyacrylate group (derived from MAS), and the acrylate group (derived from ASBO). As discussed by O'Hara (O'Hara, "Resins and Monomers for Today's Radiation Curable Coatings," in *Radiation Curing of Polymers*, Randel (Ed.), The Royal Society of Chemistry, London, 1987, pg. 116-127), the relative reactivity of these three functional groups in free radical photopolymerization is:

allyl<methacrylate<acrylate

It seems logical to expect that poor copolymerizability between these three different functional groups would lead to a broader distribution of molecular weight between crosslinks. For example, if the acrylate groups present in the ASBO are consumed faster than the allyl or methacrylate groups present in MAS, then the initial network would be mostly comprised of segments derived from ASBO and, as a result, would possess an initial distribution of molecular weights between crosslinks that is characteristic of ASBO polymerization. As the concentration of acrylate groups is depleted, consumption of methyacrylate groups and allyl groups would become kinetically competitive with acrylate group consumption resulting a different distribution of molecular weights between crosslinks that is more characteristic of MAS polymerization. This scenario has some features that are akin to the production of interpenetrating polymer networks in which an initial network is formed from one monomer or set of monomers and then that network swelled with another monomer or set of monomers used to produce a second network upon polymerization (Sperling et al., "Interpenetrating Polymer Networks," in *Polymer Blends Handbook*, Utracki (Ed.), Kluwer Academic Publishers, Dordrecht, The Netherlands, 417-447, 2002). A unique feature of interpenetrating polymer networks is the production of materials possessing a very broad Tg. This broad Tg is the result of both differences in the chemical composition of the two interpenetrating networks as well as differences in the molecular weight between crosslinks for the two different networks. Materials possessing a broad Tg have been shown to be useful for specialized applications such as vibration dampening.

Compared to the other for SBO-based reactive diluents, HF-MAS provided by far the hardest, highest modulus, highest Tg coating films. As indicated in FIG. 4A, the HF-MAS/ASBO 50/50 film possessed the highest crosslink density, as indicated by the very high storage moduli in the rubbery plateau region. This result can be attributed to the fact that HF-MAS possesses the lowest EW of all of the SBO-based reactive diluents. In addition, the tan delta response (FIG. 4B) associated with the Tg for HF-MAS/ASBO was very broad which, as just discussed, is most likely due to presence of allyl, methacrylate, and acrylate groups all in the same coating composition.

TABLE 14

Data obtained for UV cured coatings of ASBO as the reactive oligomer component and MAS or HF-MAS as the reactive diluent.

| Property | AAS/ASBO 50/50 | MAS/ASBO 50/50 | HF-MAS/ASBO 50/50 |
|---|---|---|---|
| Viscosity (cP) | 477 | 439 | 595 |
| Thickness (μm) | 79 ± 2 | 94 ± 5 | 98 + 6 |

TABLE 14-continued

Data obtained for UV cured coatings of ASBO as the reactive oligomer component and MAS or HF-MAS as the reactive diluent.

| Property | AAS/ASBO 50/50 | MAS/ASBO 50/50 | HF-MAS/ASBO 50/50 |
|---|---|---|---|
| Young's Mod. (MPa) | 199 ± 12 | 320 ± 10 | 721 ± 25 |
| Elongation (%) | 10.5 ± 3 | 4.9 ± 0.3 | 2.6 ± 0.2 |
| *E' @ 90° C. (MPa) | 43 | 38 | 100 |
| Tg (° C.) | 52 | 48 | 62 |
| Pend. Hardness (sec) | 32 ± 1 | 46 ± 1 | 72 ± 2 |
| Rev. Impact (in-lb) | 40 | <2 | <2 |
| MEK Double Rubs | 1,350 | 480 ± 15 | >1,200 |

*E' indicates storage modulus

Coatings Based on Poly(2-VOES) as the Reactive Oligomeric Component.

Recently, Alam and Chisholm (Alam et al., 2011 *J. Coat. Technol. Res.*, 8 671-683) developed a method for producing novel vinyl ether polymers from SBO that, as shown above, possess a fatty acid ester group from SBO in every repeat unit of the polymer. Compared to SBO triglycerides, which possess three fatty acid ester groups per molecule, these SBO-based vinyl ether polymers possesses 10 s to 100 s of fatty acid ester groups per polymer molecule depending on the polymer molecular weight. This feature has been shown to result in much short cure times for coatings derived from poly(2-VOES) than for analogous coatings derived from SBO. The shorter cure times obtained with the use of poly(2-VOES) are a result of the gel-point being reached at dramatically lower functional group conversion (Alam et al., 2011 *J. Coat. Technol. Res.*, 8 671-683). In addition to shorter cure times, coatings based on poly(2-VOES) or a derivatized version of poly(2-VOES) were found to possess higher crosslink densities than analogous coatings based on SBO or an SBO derivative. This feature is a result of the methine carbon atoms present in polymer backbone of poly(2-VOES) that serve as crosslinks in the network upon curing of functional groups present in the fatty acid ester pendent groups of the polymer.

Table 15 displays data obtained for coatings based on A-poly(2-VOES) as the reactive oligomeric component and APS, AAS, or A3HS as the reactive diluents. Consistent with the data obtained for analogous coatings based ASBO as the reactive diluents component, AAS provided the highest Tg, Young's modulus, hardness, chemical resistance, and crosslink density (i.e. E' in the rubbery plateau). Also consistent with the data obtained for ASBO-based coatings, A3HS provided properties that were higher than those obtained using APS as the reactive diluents, but lower than those obtained from coatings based on AAS as the reactive diluent. These results were consistent with expectations based on difference in the EW of the three different reactive diluents.

TABLE 15

Data obtained for UV cured coatings of A-poly(2-VOES) as the reactive
oligomeric component and APS, AAS, or A3HS as the reactive diluents.

|  | APS/A-Poly(2-VOES) 25/75 | AAS/A-Poly(2-VOES) 25/75 | A3HS/A-Poly(2-VOES) 25/75 | APS/A-Poly(2-VOES) 50/50 | AAS/A-Poly(2-VOES) 50/50 | A3HS/A-Poly(2-VOES) 50/50 |
|---|---|---|---|---|---|---|
| Viscosity (cP) | 9059 | 5946 | 15789 | 1699 | 957 | 5,404 |
| Thickness (μm) | 83 ± 5 | 83 ± 3 | 85 ± 4 | 78 ± 3 | 79 ± 2 | 84 ± 4 |
| Young's Mod. (MPa) | 91 ± 6 | 294 ± 21 | 205 ± 3 | 23 ± 1 | 125 ± 3 | 61 ± 1 |
| Elongation (%) | 10 ± 1 | 11 ± 1 | 8 ± 1 | 13 ± 1 | 7 ± 1 | 13 ± 1 |
| *E' @ 90° C. (MPa) | 31 | 40 | 39 | 3 | 30 | 18 |
| Tg (° C.) | 14 | 30 | 26 | −2 | 17 | 14 |
| Pend. Hardness (sec) | 32 ± 0 | 50 ± 1 | 42 ± 1 | 25 ± 0 | 35 ± 0 | 28 ± 1 |
| Rev. impact (in-lb) | 5 | 4 | 5 | 6 | 7 | 9 |
| MEK Double Rubs | 390 | 2350 | 1,400 | 135 | 1,200 | 785 |

*E' indicates storage modulus.

Figure 5A:
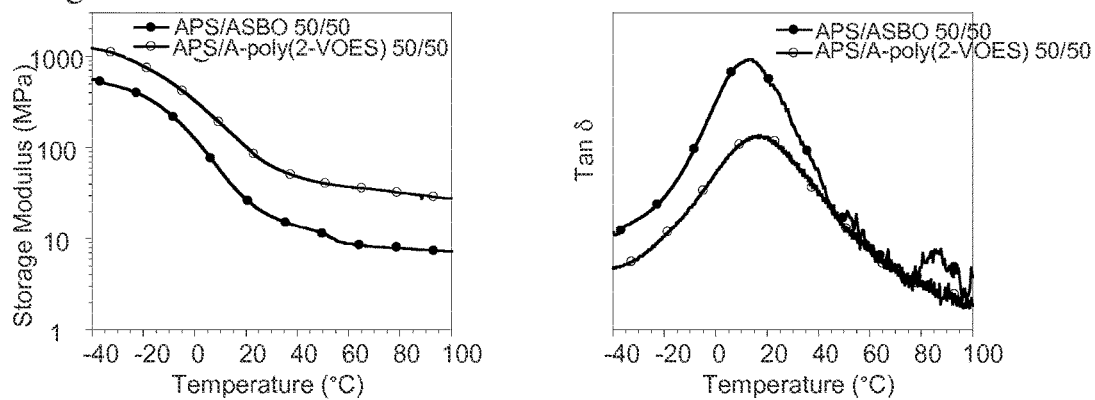
FIG. 5A shows viscoelastic properties of coating films based on A-poly(2-VOES) or ASBO as the reactive oligomer and acrylated n-propyl soyate (APS) as the reactive diluent.
Figure 5B:
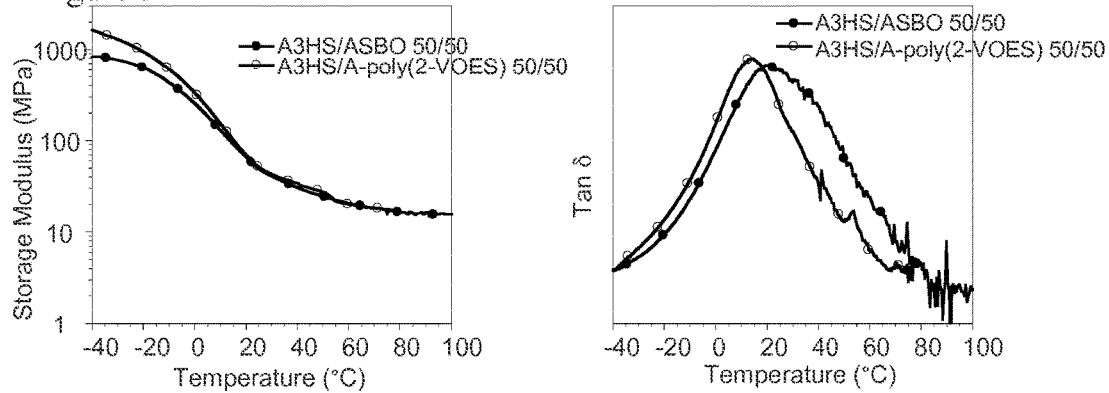
FIG. 5B shows viscoelastic properties of coating films based on A-poly(2-VOES) or ASBO as the reactive oligomer and acrylated cis-3-hexenyl soyate (A3HS) as the reactive diluent.
Figure 5C:
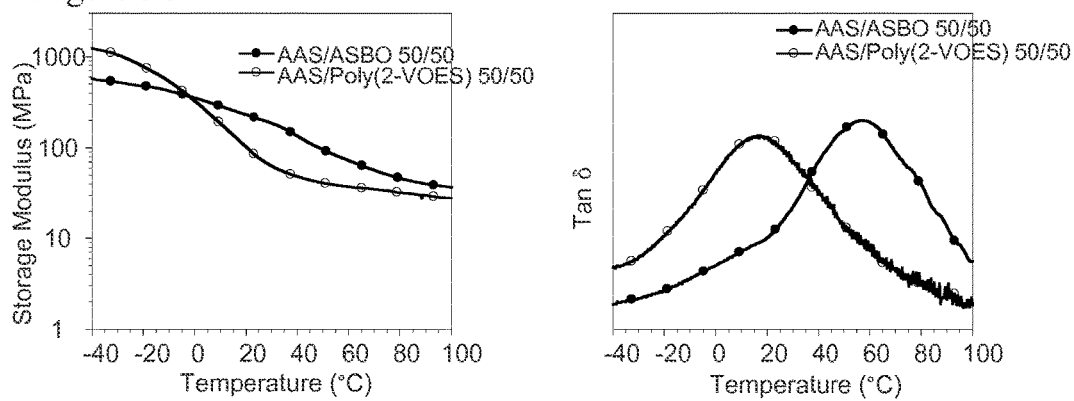
FIG. 5C shows viscoelastic properties of coating films based on A-poly(2-VOES) or ASBO as the reactive oligomer and AAS as the reactive diluent. The ratio of reactive oligomer to reactive diluent was 50/50.

FIG. 5 provides a comparison of the viscoelastic properties for coatings based on A-poly(2-VOES) to analogous coatings based on ASBO. FIGS. 5A, 5B, and 5C correspond to coating based on APS, A3HS, and AAS as the reactive diluent, respectively. An interesting trend was observed with respect to the EW of the reactive diluent and the viscoelastic response. Due to the much higher number of acrylate groups per molecule associated with A-poly(2-VOES) as compared to ASBO, it was expected that the Tg and rubbery plateau modulus for coatings based on A-poly(2-VOES) would be higher than for analogous coatings based on ASBO. This type of result has been consistently observed when the properties of coatings based on poly(2-VOES) are compared to analogous coatings based on SBO (Alam et al., 2011 *J. Coat. Technol. Res.*, 8 671-683). As shown in FIG. 5A, APS/A-poly(2-VOES) 50/50 yielded a higher Tg and higher rubbery plateau modulus compared to APS/ASBO 50/50, which is consistent with expectations. However, as shown in FIG. 5B, analogous compositions based on A3HS as the reactive diluent showed very little difference in Tg and rubbery plateau modulus between the coating based on A-poly(2-VOES) and that based on ASBO. As mentioned previously, the primary difference between APS and A3HS is that A3HS possesses a lower reactive group EW. As shown in FIG. 5C, coatings based on AAS as the reactive diluent, which has a lower reactive group EW than either A3HS and APS, showed the opposite result of what was expected; that is, the coating based on ASBO as the reactive oligomer provided a higher Tg and higher rubbery plateau modulus than the coating based on A-poly(2-VOES) as the reactive oligomer. These results may be due to diffusion limitations resulting from rapid vitrification during photo-cure.

The gel-point, defined as the extent of functional group conversion that results in the formation of an infinite polymer network (Paul et al., *Polymer Chemistry. Second ed.* Boca Raton: CRC P, 2007. 381-389), is a function of the number of functional groups per molecule for both the reactive oligomer component as well as for the diluent. For A-poly(2-VOES), the number of acrylate groups per molecular is equal to 1.5 DP where DP is the degree of polymerization (Alam et al., 2011 *J. Coat. Technol. Res.*, 8 671-683). So, if the DP of A-poly(2-VOES) was 100, than the number of acrylate groups per polymer molecule would be 150. In contrast, the number of acrylate per molecule for ASBO is dramatically lower at about 4.5. Thus, it can easily be understood that the gel-point will be reached at a much lower extent of acrylate group conversion for A-poly(2-VOES) as compared to ASBO (Pinner, 1956 *J. Polym. Sci.*, 21, 153-157). At the gel-point, segmental mobility and molecular diffusion are greatly reduced which can significantly reduce the rate of polymerization of remaining functional groups. With regard to the three reactive diluents, the functional group EW for APS, A3HS, and AAS are 314, 240, and 188 g/mole, respectively. Thus, for a given reactive oligomer, the use of AAS would result in the gel-point being reached at the lowest extent of functional group conversion, while the use of APS would necessitate the highest functional group conversion before reaching the gel point. Considering these differences, the combination of the relatively large number of functional groups per molecule for A-poly(2-VOES) with the relatively low functional group EW of AAS may result in such rapid vitrification upon UV exposure that overall functional group conversion and, as a result, crosslink density is limited due diffusion limitations. Thus, even though, the use of A-poly(2-VOES) in conjunction with AAS should provide the coating with the highest crosslink density, diffusion limitations resulting from rapid vitrification resulting from the gel-point being reached at a very low degree of functional group conversion may be limiting the overall extent of functional group conversion and, thus, the crosslink density. Further investigation involving direct measurements of functional group conversion during photo-curing will be conducted to unambiguously determine if this explanation is correct.

CONCLUSION

ASBO has been commercialized for applications such as photocurable coatings and thermoset composites. Since the viscosity ASBO is relatively high, a reactive diluent is required to produce photocurable compositions that are processable and essentially free of VOCs. Since most all reactive diluents are derived from petroleum and coatings with high renewable contents are desired, there is a need for new reactive diluents based on renewable resources. Five SBO-based acrylates/methacrylates were synthesized and investigated.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A functionalized polysiloxane comprising a compound having formula I:

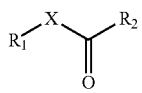

(I)

wherein $R_1$ is an organic group comprising at least one double or triple carbon-carbon bond; X is O, $NR_3$, N, or S; $R_2$ is a fatty acid residue; and $R_3$ is H or alkyl; provided that where $R_1$ comprises a double carbon-carbon bond, neither atom α to the double carbon-carbon bond is O.

2. The functionalized polysiloxane of claim 1, wherein the fatty acid residue is from a plant oil triglyceride.

3. The functionalized polysiloxane of claim 1, wherein $R_1$ is allyl.

4. The functionalized polysiloxane of claim 2, wherein the plant oil is selected from the group consisting of soybean oil, linseed oil, sunflower oil, safflower oil, canola oil, corn oil, cashew nut oil, olive oil, peanut oil, palm oil, sesame oil, cottonseed oil, rapeseed oil, walnut oil, almond oil and coconut oil.

5. The functionalized polysiloxane of claim 4, wherein the oil is soybean oil.

6. The functionalized polysiloxane of claim 1, wherein at least one of $R_1$ and $R_2$ contains at least one functionality selected from the group consisting of epoxide, acrylate, methacrylate, hydroxyl, and cyclic carbonate.

7. A composition comprising a plurality of functionalized polysiloxanes of claim 1.

8. The composition of claim 7, wherein the plant oil is soybean oil, and wherein for each of the plurality of compounds, $R_2$ is a fatty acid residue independently selected from a linolenic acid, a linoleic acid, an oleic acid, a stearic acid, and a palmitic acid.

9. A curable composition comprising at least one functionalized polysiloxane of claim 1.

10. The curable composition of claim 9 comprising a reactive diluent comprising the functionalized polysiloxane of claim 1.

11. A urethane or polyurethane comprising the functionalized polysiloxane of claim 1 or a derivative thereof.

12. A method for making a functionalized polysiloxane comprising contacting a compound having formula I:

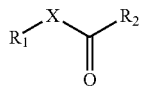

(I)

wherein $R_1$ is an organic group comprising at least one double or triple carbon-carbon bond; X is O, $NR_3$, N, or S; $R_2$ is a fatty acid residue; and $R_3$ is H or alkyl; provided that where $R_1$ comprises a double carbon-carbon bond, neither atom α to the double carbon-carbon bond is O, with a polysiloxane to yield a functionalized polysiloxane.

13. A coating, film, fiber, foam, adhesive, ink, plastic, elastomer, paint, molding compound, thermoplastic, resin, sealant, lubricant or composite comprising the functionalized polysiloxane of claim 1 or a derivative thereof.

* * * * *